US010112968B2

(12) United States Patent
Olhava et al.

(10) Patent No.: US 10,112,968 B2
(45) Date of Patent: Oct. 30, 2018

(54) INHIBITORS OF PROTEIN METHYLTRANSFERASE DOT1L AND METHODS OF USE THEREOF

(71) Applicant: Epizyme, Inc., Cambridge, MA (US)

(72) Inventors: Edward J. Olhava, Newton, MA (US); Richard Chesworth, Concord, MA (US); Roy M. Pollock, Medford, MA (US); Lei Jin, Wellesley, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 15/176,052

(22) Filed: Jun. 7, 2016

(65) Prior Publication Data

US 2017/0137455 A1  May 18, 2017

Related U.S. Application Data

(63) Continuation of application No. 14/420,877, filed as application No. PCT/US2013/054580 on Aug. 12, 2013, now abandoned.

(60) Provisional application No. 61/682,090, filed on Aug. 10, 2012.

(51) Int. Cl.
| *A01N 43/04* | (2006.01) |
| *A61K 31/70* | (2006.01) |
| *C07H 19/16* | (2006.01) |
| *C07H 19/14* | (2006.01) |
| *G06F 19/16* | (2011.01) |
| *C40B 30/02* | (2006.01) |
| *A61K 31/708* | (2006.01) |
| *A61K 31/7064* | (2006.01) |
| *A61K 31/7068* | (2006.01) |
| *A61K 31/7072* | (2006.01) |
| *A61K 31/7076* | (2006.01) |

(52) U.S. Cl.
CPC ............ *C07H 19/16* (2013.01); *C07H 19/14* (2013.01); *C40B 30/02* (2013.01); *G06F 19/16* (2013.01); *A61K 31/708* (2013.01); *A61K 31/7064* (2013.01); *A61K 31/7068* (2013.01); *A61K 31/7072* (2013.01); *A61K 31/7076* (2013.01)

(58) Field of Classification Search
None
See application file for complete search history.

(56) References Cited

U.S. PATENT DOCUMENTS

| 7,576,069 B2 | 8/2009 | Rieger et al. |
| 8,580,762 B2 | 11/2013 | Olhava et al. |
| 8,722,877 B2 | 5/2014 | Chesworth et al. |
| 9,012,166 B2 | 4/2015 | Nishino et al. |
| 9,029,343 B2 | 5/2015 | Chesworth et al. |
| 9,096,634 B2 | 8/2015 | Olhava et al. |
| 9,145,438 B2 | 9/2015 | Chesworth et al. |
| 9,446,064 B2 | 9/2016 | Klaus et al. |
| 9,597,348 B2 | 3/2017 | Olhava et al. |
| 2004/0147464 A1 | 7/2004 | Roberts et al. |
| 2006/0040889 A1 | 2/2006 | Rieger et al. |
| 2006/0189636 A1 | 8/2006 | Critchley et al. |
| 2006/0235037 A1 | 10/2006 | Purandare et al. |
| 2007/0191293 A1 | 8/2007 | Langston et al. |
| 2008/0064653 A1 | 3/2008 | Li et al. |
| 2008/0132525 A1 | 6/2008 | Wahhab et al. |
| 2009/0105476 A1 | 4/2009 | Fairhurst et al. |
| 2010/0144655 A1 | 6/2010 | Chen et al. |
| 2012/0122895 A1 | 5/2012 | Jiang et al. |
| 2012/0142625 A1 | 6/2012 | Olhava et al. |
| 2013/0029878 A1 | 1/2013 | Nishino et al. |
| 2013/0310334 A1 | 11/2013 | Chesworth et al. |
| 2013/0338173 A1 | 12/2013 | Olhava et al. |
| 2014/0051654 A1 | 2/2014 | Olhava et al. |
| 2014/0323421 A1 | 10/2014 | Klaus et al. |
| 2015/0011495 A1 | 1/2015 | Olhava et al. |
| 2015/0284422 A1 | 10/2015 | Olhava et al. |
| 2015/0342979 A1 | 12/2015 | Pollock et al. |
| 2015/0366893 A1 | 12/2015 | Olhava et al. |
| 2016/0045531 A1 | 2/2016 | Klaus et al. |
| 2017/0165288 A1 | 6/2017 | Olhava et al. |

FOREIGN PATENT DOCUMENTS

| CN | 102066372 A | 5/2011 |
| EP | 1 138 688 A1 | 10/2001 |
| EP | 2 208 721 A1 | 7/2010 |
| EP | 2 562 264 A1 | 2/2013 |
| JP | 2011-239775 A | 12/2011 |
| WO | WO 2001/072764 A1 | 10/2001 |
| WO | WO 2001/077075 A2 | 10/2001 |
| WO | WO 2002/100152 A2 | 12/2002 |
| WO | WO 2003/074083 A1 | 9/2003 |
| WO | WO 2004/007512 A2 | 1/2004 |
| WO | WO 2004/022572 A1 | 3/2004 |
| WO | WO 2006/015357 A2 | 2/2006 |

(Continued)

OTHER PUBLICATIONS

Daigle et al. "Selective Killing of Mixed Lineage Leukemia Cells by a Potent Small-Molecule DOT1L Inhibitor", *Cancer Cell*, 2011, vol. 20, pp. 53-65.

(Continued)

*Primary Examiner* — Patrick T Lewis
(74) *Attorney, Agent, or Firm* — Cooley LLP; Heidi A. Erlacher; Xixi Sun

(57) ABSTRACT

The present invention relates to DOT1L inhibitors and methods of identifying, designing, or optimizing them. The present invention also relates to crystals of DOT1L-inhibitor complexes, the crystal structures thereof, and the use of the crystal structures. Also disclosed are pharmaceutical compositions containing these DOT1L inhibitors and methods of treating disorders in which DOT1-mediated protein methylation plays a part, such as cancer and neurological disorders, by administering these compounds and pharmaceutical compositions to subjects in need thereof.

14 Claims, 13 Drawing Sheets
Specification includes a Sequence Listing.

(56) References Cited

FOREIGN PATENT DOCUMENTS

| | | |
|---|---|---|
| WO | WO 2006/028618 A1 | 3/2006 |
| WO | WO 2006/063058 A2 | 6/2006 |
| WO | WO 2006/078752 A2 | 7/2006 |
| WO | WO 2006/113615 A2 | 10/2006 |
| WO | WO 2007/100304 A1 | 9/2007 |
| WO | WO 2008/124150 A1 | 10/2008 |
| WO | WO 2009/089425 A1 | 7/2009 |
| WO | WO 2010/027005 A1 | 3/2010 |
| WO | WO 2010/048149 A2 | 4/2010 |
| WO | WO 2011/023081 A1 | 3/2011 |
| WO | WO 2012/075381 A1 | 6/2012 |
| WO | WO 2012/075492 A2 | 6/2012 |
| WO | WO 2012/075500 A2 | 6/2012 |
| WO | WO 2012/082436 A2 | 6/2012 |

OTHER PUBLICATIONS

Marrone et al. "Structure-Based Drug Design: Computational Advances", Annu. Rev. Pharmacol. Toxicol, 1997, vol. 37, pp. 71-90.

Min, Jinrong, et al., "Structure of the Catalytic Domain of Human DOT1L, a Non-SET Domain Nucleosomal Histone Methyltransferase.", Cell, 2013, vol. 112 No. 5, pp. 711-723.

Yao, Yun, et al., "Selective Inhibitors of Histone Methyltransferase DOT1L; Design, Synthesis, and Crystallographic Studies.", Journal of the American Chemical Society, 2011, vol. 133 No. 42, pp. 16746-16749.

Basavapathruni, A. et al. "Conformational Adaptation Drives Potent, Selective and Durable Inhibition of the Human Protein Methyltransferase DOT1l", Chem. Biol. Drug Des., vol. 80, No. 6, (Oct. 9, 2012), pp. 971-980.

Bernt, K.M. et al., "Demonstration of a Role for Dot11 in MLL-Rearranged Leukemia Using a Conditional Loss of Function Model" Blood, vol. 116, No. 21, (Nov. 2010), p. 62.

Chen L. et al., "Abrogation of MLL-AF10 and CALM-AF10 Mediated Transformation Through Genetic Inactivation or Pharmacological Inhibition of the H3K79 Methyltransferase DOT1l", Blood, vol. 120, No. 21, (Nov. 2012), p. 2384.

Chen, L. et al. (Apr. 2013) "Abrogation of MLL-AF10 and CALM-AF10 Mediated Transformation Through Genetic Inactivation or Pharmacological Inhibition of the H3K79 Methyltransferase DOT1l", Leukemia, vol. 27, No. 4, pp. 813-822.

Copeland, R.A. (Oct. 2012) "Protein methyltransferase inhibitors as personalized cancer therapeutics", Drug Discov. Today Ther. Strateg., vol. 9, No. 2-3, pp. e83-e90.

Gao, W-L and H-L. Liu (2007) "DOT1: A distinct class of histone lysine methyltransferase", Hereditas, 29(12):1449-1454.

Jiang X. et al., "Blockade of miR-150 Maturation by MLL-Fusion/MYC/Lin-28 Is Required for MLL-Associated Leukemia", Abstract presented at the 54th ASH Annual Meeting and Exposition, Atlanta, Georgia, Dec. 8-11, 2012 [online]. Retrieved from: https://ash.confex.com/ash/2012/webprogram/Paper48644.html, on Jul. 15, 2015, 2 pages. Also published in: Blood, vol. 120, No. 21, (Nov. 2012), p. 3499.

Jiang, X. et al., "Blockade of miR-150 Maturation by MLL-Fusion/MYC/Lin-28 Is Required for MLL-Associated Leukemia", Cancer Cell, vol. 22, No. 4, (Oct. 2012), p. 524-535.

Olver, I. "Chemotherapy for elderly patients with advanced cancer: is it worth it?", Australian Prescriber (2000), vol. 23, pp. 80-82 [online]. Retrieved from: http://www.australianprescriber.com/magazine/23/4/80/2, on Oct. 6, 2015, 4 pages.

Seifert, M. et al. (2007) "Essential Factors for Successful Virtual Screening" Mini-Reviews in Medicinal Chemistry, 7:63-72.

Yu, W. et al. (Dec. 18, 2012) "Catalytic site remodelling of the D0T1L methyltransferase by selective inhibitors" Nature Commun, 3:1288; DOI: 10.1038/ncomms2304, including Corrigendum, 12 pages.

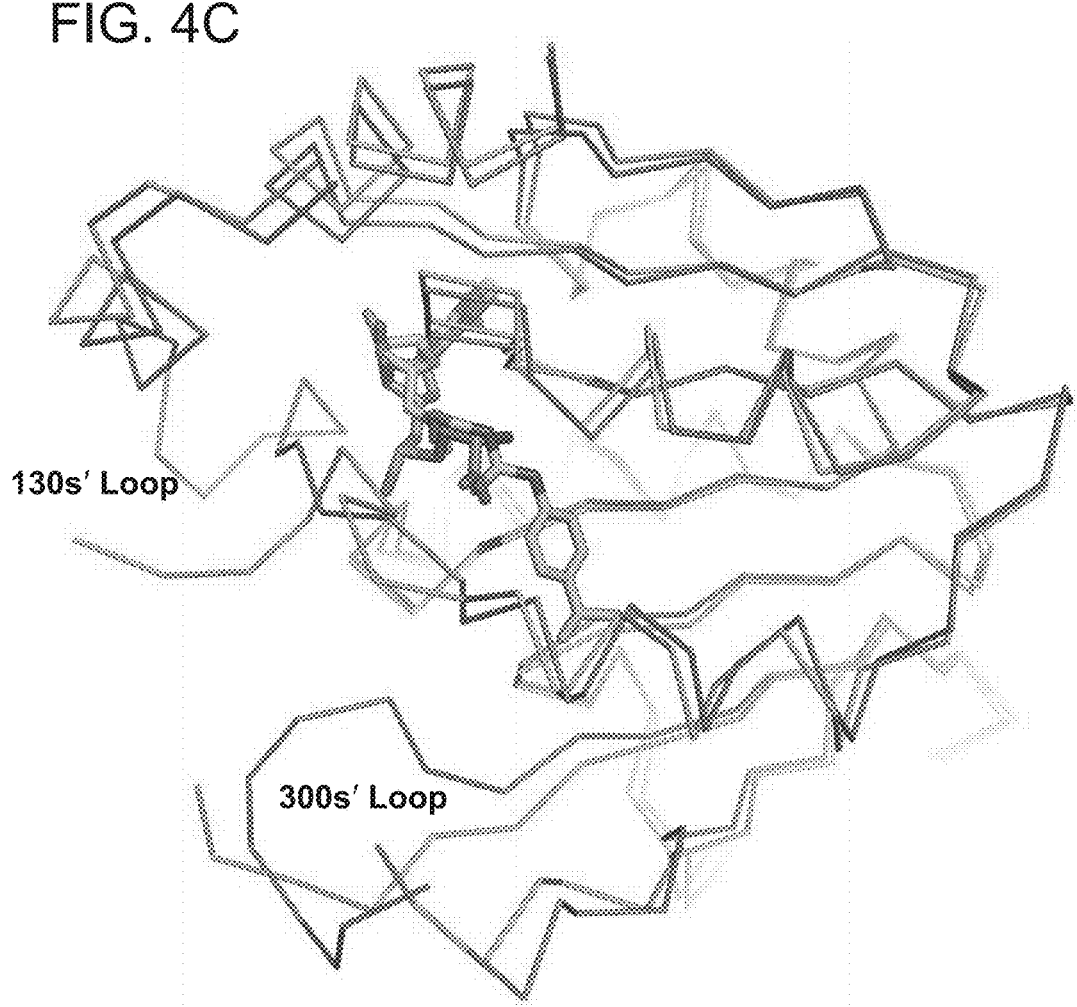

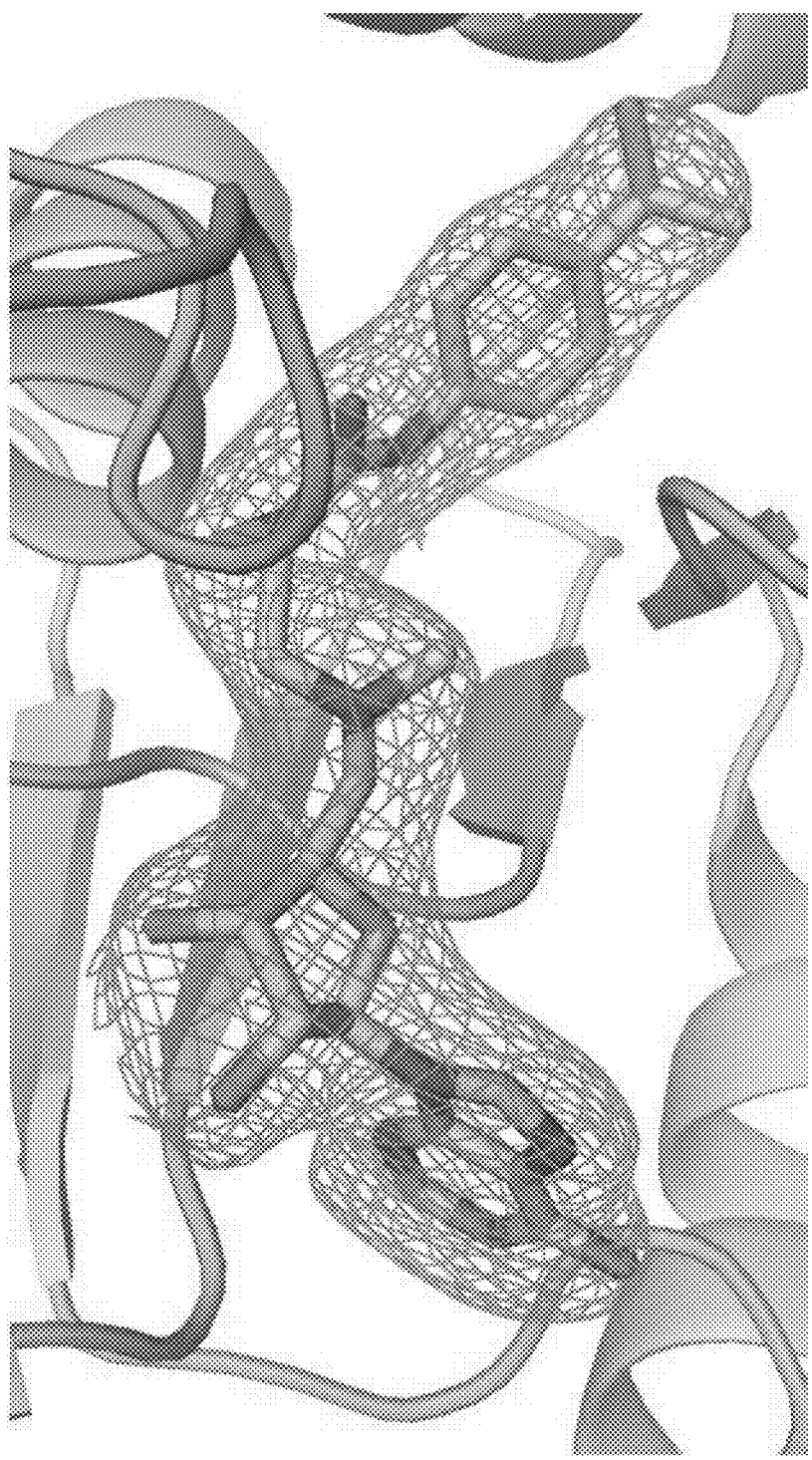

INHIBITORS OF PROTEIN METHYLTRANSFERASE DOT1L AND METHODS OF USE THEREOF

RELATED APPLICATIONS

This application is a continuation of U.S. application Ser. No. 14/420,877, filed Feb. 10, 2015, which is a national stage application, filed under 35 U.S.C. § 371, of International Application No. PCT/US2013/054580, filed Aug. 12, 2013, claims priority to, and the benefit of, U.S. Provisional Application No. 61/682,090, filed Aug. 10, 2012, the entire contents of each of which are incorporated herein by reference in their entireties.

INCORPORATION-BY-REFERENCE OF SEQUENCE LISTING

The contents of the text file named "EPIZ-011N01US-ST25.txt", which was created on Jun. 9, 2015 and is 3.9 KB in size, are hereby incorporated by reference in their entireties.

SUMMARY OF THE INVENTION

The invention is based upon the discovery that a surprising conformational adaptation results in high-affinity inhibitor binding of aminonucleoside inhibitors of DOT1L to the enzyme and prolonged residence time.

The invention provides compounds useful for selectively inhibiting DOT1L. The present invention also provides pharmaceutically acceptable salts, esters, and/or N-oxides, of these compounds.

The invention further features a method for designing, identifying, and/or optimizing a candidate DOT1L inhibitor.

In one aspect, the invention features a compound of Formula (I) below or a pharmaceutically acceptable salt or ester thereof:

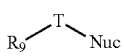

(I)

wherein,

Nuc is adenosine-like moiety or an analog or a derivative thereof,

T is a linker group of a 6-10 carbon atoms, in which one or more carbon atoms are optionally replaced with a heteroatom and T is optionally substituted;

Nuc-T is capable of binding within the SAM binding pocket of human DOT1L which comprises amino acid residues 135-241 of SEQ ID NO: 1; and $R_9$ is a group such that $R_9$ induces a conformational adaptation in human DOT1L, wherein the conformational adaptation is the formation of a hydrophobic pocket domain which comprises amino acid residues 139-312 of SEQ ID NO: 1; and further wherein Nuc-T is capable of binding within the SAM binding pocket of human DOT1L which comprises amino acid residues 135-241 of SEQ ID NO: 1.

In another aspect, the invention features a method for designing and/or identifying a potential binding compound for protein DOT1L. The method comprises:

(a) generating, on a computer, a three-dimensional structure of DOT1L having the structural coordinates of Table S1 or S2;

(b) identifying amino acid residues forming an hydrophobic pocket site in the three-dimensional structure of DOT1L from step (a), wherein the hydrophobic pocket domain of DOT1L is characterized by the crystallography coordinates of human DOT1L amino acids Leu143, Met147, Phe239, and Tyr 312 according to Table S1 or S2;

(c) generating a three-dimensional model of the active site;

(d) designing and/or selecting a compound that potentially binds to the active site using the three-dimensional model of the active site; and (e) synthesizing and/or choosing the potential binding compound.

In yet another aspect, the invention features a method for designing and/or identifying a potential binding compound for protein DOT1L, the method comprising computationally identifying a binding compound that binds to DOT1L using the atomic coordinates of Leu143, Met147, Phe239, and Tyr 312 according to Table S1 or S2.

In still another aspect, the invention features a method for designing and/or identifying a potential binding compound for protein DOT1L, the method comprising:

a) providing a set of atomic coordinates for human DOT1L as set forth in Table S1 or S2; and b) identifying in silico a binding compound that binds to DOT1L using the coordinates of step (a).

The invention also features a method of identifying a drug candidate for the treatment of a disease, the method comprising:

a) using the atomic coordinates set forth in Table S1 or S2 to form a three-dimensional structure of DOT1L;

b) selecting a test compound having the best fit with the structure of DOT1L; and c) assaying the ability of the test compound to modulate DOT1L activity, wherein a test compound that modulates DOT1L activity is considered a drug candidate for treating a disease.

In another aspect, the invention features a DOT1L inhibitor having molecular dimensions compatible with the shape of a hydrophobic pocket domain of DOT1L characterized by the crystallography coordinates of human DOT1L amino acids Leu143, Met147, Phe239, and Tyr 312, according to Table S1 or S2, wherein the compound has a biochemical $IC_{50}$ for DOT1L of less than 100 nM.

The invention also features a computer readable medium comprising the atomic coordinates of one or more DOT1L-Compound A2, DOT1L-Compound C1, DOT1L-Compound C118 and DOT1L-Compound D16.

The invention also features a method for designing, identifying, and/or optimizing a candidate DOT1L inhibitor compound or complex. The method comprises:

(a) generating a crystal structure, a three-dimensional model of DOT1L, or obtaining the structure coordinates of DOT1L in complex with the candidate DOT1L inhibitor compound or complex, and (b) determining if the candidate DOT1L inhibitor compound or complex induces a conformational adaptation and/or a hydrophobic binding site of the DOT1L from the three-dimensional model.

In yet another aspect, the invention features a method for designing, identifying, and/or optimizing a candidate DOT1L inhibitor compound or complex that interacts with all or a part of a hydrophobic pocket domain which comprises amino acid residues 139-312 of SEQ ID NO: 1 and the SAM binding pocket of human DOT1L which comprises amino acid residues 135-241 of SEQ ID NO: 1. The method includes (a) producing the structure coordinates of the hydrophobic binding pocket of DOT1L in silico comprising the means for generating three-dimensional structural information from the coordinates;

(b) designing, selecting and/or optimizing the candidate DOT1L inhibitor compound or complex by performing a fitting operation between the candidate DOT1L inhibitor compound or complex and the three-dimensional structural information of all or part of the hydrophobic binding pocket or DOT1L protein; and (c) optionally employing computerized and/or reiterative steps.

The invention also relates to a pharmaceutical composition of a compound of Formula (I) and a pharmaceutically acceptable carrier.

The invention also relates to a pharmaceutical composition comprising a DOT1L inhibitor designed, identified, and/or optimized by the method disclosed herein and a pharmaceutically acceptable carrier.

The invention also relates to a pharmaceutical composition of a salt of a compound of Formula (I) or a salt of a DOT1L inhibitor designed, identified, and/or optimized by the method disclosed herein and a pharmaceutically acceptable carrier.

The invention also relates to a pharmaceutical composition of a hydrate of a compound of Formula (I) or a hydrate of a DOT1L inhibitor designed, identified, and/or optimized by the method disclosed herein and a pharmaceutically acceptable carrier.

The present invention provides methods of treating or preventing cancer. The present invention provides methods of treating cancer. The present invention also provides methods of preventing cancer. The method includes administering to a subject in need thereof a therapeutically effective amount of the compound of Formula (I) or a therapeutically effective amount of a DOT1L inhibitor designed, identified, and/or optimized by the method disclosed herein. The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11q23. The present invention provides methods of treating a disease or disorder mediated by translocation of a gene on chromosome 11q23. The present invention also provides methods of preventing a disease or disorder mediated by translocation of a gene on chromosome 11q23. The method includes administering to a subject in need thereof a therapeutically effective amount of the compound of Formula (I) or a therapeutically effective amount of a DOT1L inhibitor designed, identified, and/or optimized by the method disclosed herein.

The present invention provides methods of treating or preventing a disease or disorder in which DOT1-mediated protein methylation plays a part or a disease or disorder mediated by DOT1-mediated protein methylation. The present invention provides methods of treating a disease or disorder in which DOT1-mediated protein methylation plays a part or a disease or disorder mediated by DOT1-mediated protein methylation. The present invention also provides methods of preventing a disease or disorder in which DOT1-mediated protein methylation plays a part or a disease or disorder mediated by DOT1-mediated protein methylation. The method includes administering to a subject in need thereof a therapeutically effective amount of the compound of Formula (I) or a therapeutically effective amount of a DOT1L inhibitor designed, identified, and/or optimized by the method disclosed herein.

The present invention provides methods of inhibiting DOT1L activity in a cell. The method includes contacting the cell with an effective amount of one or more of the compound of Formula (I) or one or more of the DOT1L inhibitor designed, identified, and/or optimized by the method disclosed herein.

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

The present invention relates to use of the compounds disclosed herein in preparation of a medicament for treating or preventing cancer. The use includes a compound of Formula (I) for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound of Formula (I) or a DOT1L inhibitor designed, identified, and/or optimized by the method disclosed herein for administration to a subject in need thereof in a therapeutically effective amount.

The present invention provides use of the compounds disclosed herein in preparation of a medicament for treating or preventing a disease or disorder in which DOT1-mediated protein methylation plays a part or a disease or disorder mediated by DOT1-mediated protein methylation. The use includes a compound of Formula (I) or a DOT1L inhibitor designed, identified, and/or optimized by the method disclosed herein for administration to a subject in need thereof in a therapeutically effective amount.

The present invention provides use of the compounds disclosed herein for inhibiting DOT1L activity in a cell. The use includes contacting the cell with an effective amount of one or more of the compound of Formula (I) and/or the DOT1L inhibitor designed, identified, and/or optimized by the method disclosed herein.

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1 through H3-K79 methylation.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DESCRIPTION OF THE FIGURES

FIG. 4C shows loop disorder induced by binding of Compound C118 to DOT1L. Superimposition of DOT1L-SAM and DOT1L-Compound C118 shows the disorder in 130s' and 300s' loops upon the binding of Compound C118. DOT1L protein: in line presentation (carbon atoms: green for the DOT1L-Compound C118 structure and light blue for the DOT1L-SAM structure). Compound C118: stick presentation (carbon atoms: green; oxygen: red; nitrogen: dark blue). SAM: stick presentation (carbon atoms: light blue; oxygen: red; nitrogen: dark blue; sulfur: yellow)

FIG. 10B shows a 2Fo-Fc map for Compound C118. This map was contoured at 1 σ.

DETAILED DESCRIPTION OF THE INVENTION

Figure 1:
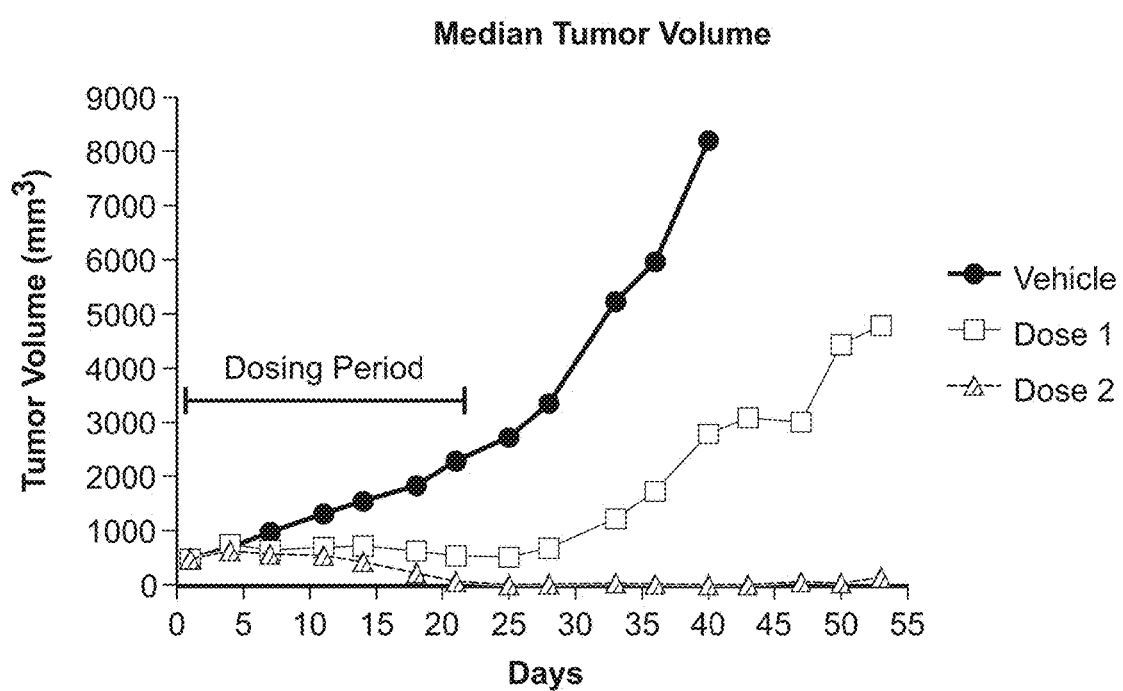
FIG. 1 is a plot showing that Compound A2 causes complete and sustained tumor regression in a MV4-11 nude rat xenograft model of MLL-rearranged leukemia.

Certain aspects of the present invention provide compounds that can be used to selectively modulate the aberrant action of an epigenetic enzyme. Further, the compounds can be used to treat or prevent a disease state in a mammal caused or mediated by aberrant action of an epigenetic enzyme. The present invention includes pharmaceutically acceptable salts, esters, tautomers, and N-oxides of these compounds. Certain aspects of the present invention also provide methods of designing, identifying, and/or optimizing novel compounds as DOT1L inhibitors, synthetic methods for making the compounds, pharmaceutical compositions containing them and various uses of the compounds.

One aspect of the present invention relates to compounds that selectively modulate the activity of the histone methyltransferase DOT1L, an enzyme known to methylate lysine 79 of histone H3 ("H3K79") in vivo (Feng et al. (2002) *Curr. Biol.* 12:1052-1058). Similar to other HMTases, DOT1L contains a S-adenosylmethionine (SAM) binding site and uses SAM as a methyl donor. However, unlike other reported HMTases, the DOT1 polypeptides do not contain a SET domain.

DOT1L nucleic acid and polypeptides have previously been described (see, e.g., U.S. Patent Application Publication No. 2005-0048634 A1 (hereby incorporated by reference); Feng et al. (2002) *Curr. Biol.* 12:1052-1058; and Okada et al. (2005) *Cell* 121:167-78). The sequences of the human nucleic acid and protein have been deposited under GenBank Accession No. AF509504, which is hereby incorporated by reference in its entirety. Only the approximately 360 N-terminal amino acids of hDOT1L share significant sequence similarity with the yeast DOT1. In addition, DOT1 homologs from *C. elegans* (GenBank Accession Nos. NP510056 and CAA90610), *Drosophila* (GenBank Accession Nos. CG10272 and AAF54122), mouse (GenBank Accession No. XP125730), *Anopheles gambiae* (GenBank Accession No. EAA03558), and *Neurospora crassa* (GenBank Accession No. EAA33634) are available in public databases (the disclosures of which are incorporated by reference herein in their entireties). The SAM binding domain among these homologs is conserved (approximately 30-100% amino acid sequence identity and 50-100% amino acid similarity). Various aspects of the present invention can be practiced with any DOT1L polypeptide or nucleic acid.

The 2.5 angstrom resolution structure of a fragment of the hDOT1L protein containing the catalytic domain (amino acids 1-416; SEQ ID NO: 1) has been solved, and the atomic coordinates for amino acids 1-416 of hDOT1L have been determined and deposited in the RCSB database under ID code 1NW3 and described in the scientific literature (Min et al. (2003) *Cell* 112:711-723), the disclosures of both of which are incorporated herein by reference in their entireties. As an example, human DOT1L includes the protein comprising SEQ ID NO:1 and variants thereof comprising at least about 70% amino acid sequence identity to SEQ ID NO:1, or preferably 80%, 85%, 90% and 95% sequence identity to SEQ ID NO:1, or more preferably, at least about 95% or more sequence identity to SEQ ID NO:1.

It has recently been demonstrated that hDOT1L plays an important role in MLL-AF10-mediated leukemogenesis (Okada et al. (2005) *Cell* 121:167-78). It was also shown that mistargeting of hDOT1L to the Hoxa9 gene by MLL-AF10 results in H3K79 methylation and Hoxa9 upregulation which contributes to leukemic transformation (Okada et al. (2005) *Cell* 121:167-78). It was further demonstrated that the hDOT1L and MLL-AF10 interaction involves the OM-LZ (octapeptide motif-leucine zipper) region of AF10, required for MLL-AF10-mediated leukemic transformation (DiMartino et al. (2002) *Blood* 99:3780-5). It has also been shown that CALM-AF10 fusion appears to be both necessary and sufficient to mediate leukemogenesis in vitro and in vivo; that hDOT1L and its H3K79 methyltransferase activity are implicated in CALM-AF10-mediated leukemic transformation; and that the Hoxa5 gene is involved in CALM-AF10-mediated transformation (U.S. Patent Application Publication No. 2009-0061443 A1, which is hereby incorporated by reference in its entirety). Aberrant recruitment of DOT1L leading to deregulated gene expression may be a common feature of many other oncogenic MLL-fusion proteins. For example, the MLL fusion partners ENL, AF4, and AF9 are normally found in nuclear complexes with DOT1L (Bitoun et al. (2007) *Hum. Mol. Genet.* 16:92-106, Mueller et al. (2007) *Blood* 110:4445-54, Zhang et al. (2006) *J. Biol. Chem.* 281:18059-68), and altered H3K79 methylation profiles are a feature of murine and human MLL-AF4 leukemias (Krivstov et al. (2008) *Cancer Cell* 14:355-368).

The present disclosure presents the design and optimization of a series of aminonucleoside inhibitors of the PKMT DOT1L. Using the crystal structures of various aminonucleoside inhibitors bound to human DOT1L, the key recognition elements of ligand binding to the enzymatic active site have been systematically defined. Conformational adaptation is a common feature of enzyme catalysis and of high-affinity ligand interactions with enzymes. This is clearly the case with the potent aminonucleoside inhibitors of DOT1L. A novel hydrophobic pocket, immediately adjacent to the SAM binding site of the enzyme has been discovered by the applicants. It was opened up to accommodate the extended aminonucleoside compounds that had been originally designed to engage the lysine binding channel of the contiguous enzyme active site. This structural adaptation results in very high-affinity binding of aminonucleosides to the enzyme and provided new directions for inhibitor optimization. The conformational adaptation mechanism of inhibitor binding demonstrated for the aminonucleosides also results in extended residence time for the optimized members of this inhibitor series. For example, D16 displays a DOT1L enzyme residence time of sixty minutes, as measured by surface plasmon resonance. A long residence time on PMT targets, such as DOT1L, may prove to be of value in demonstrating durable pharmacology in patients.

The invention features a method of designing, identifying, and/or optimizing an inhibitor of DOT1L, e.g., an aminonucleoside DOT1L inhibitor. The designing of inhibitors can be initiated using mechanism-guided design principles, based on the DOT1L enzymatic reaction mechanism, and optimized through structure-guided approaches using iterative enzyme-inhibitor complex crystal structures. In embodiments, conformational adaptation of the enzyme active site attends potent inhibitor binding and this observation can be taken into account to develop a cogent structure-activity relationship (SAR) for active site-directed DOT1L inhibition. In one embodiment, this optimization process results in Compound D16, which is a picomolar inhibitor of DOT1L with exquisite selectivity for its target enzyme. Compound D16 has been shown to demonstrate potent and selective killing of MLL-rearranged leukemic cells, both in cell culture and in a highly aggressive disseminated mouse model of this disease. Thus, the methods described herein provide ways to identify, design, or optimize potent, selective small molecule inhibitors of DOT1L to affect selective killing of MLL-rearranged leukemias.

The method of the invention includes:
 (a) generating, on a computer, a three-dimensional structure of DOT1L having the structural coordinates of Table S1 or S2;
 (b) identifying amino acid residues forming an hydrophobic pocket site in the three-dimensional structure of DOT1L from step (a), wherein the hydrophobic pocket domain of DOT1L is characterized by the crystallography coordinates of human DOT1L amino acids Leu143, Met147, Phe239, and Tyr 312 according to Table S1 or S2;
 (c) generating a three-dimensional model of the active site;

(d) designing and/or selecting a compound that potentially binds to the active site using the three-dimensional model of the active site; and (e) synthesizing and/or choosing the potential binding compound.

The method can further include contacting the identified candidate inhibitor with the DOT1L in order to determine the effect of the inhibitor on DOT1L enzymatic activity, e.g., by evaluating the residence time, $K_i$ value, or in an in vivo study.

The invention also features a method of identifying a drug candidate for the treatment of a disease, the method comprising:

a) using the atomic coordinates set forth in Table S1 or S2 to form a three-dimensional structure of DOT1L;

b) selecting a test compound having the best fit with the structure of DOT1L; and c) assaying the ability of the test compound to modulate DOT1L activity, wherein a test compound that modulates DOT1L activity is considered a drug candidate for treating a disease.

The invention also features a method for designing, identifying, and/or optimizing a candidate DOT1L inhibitor compound or complex. The method comprises:

(a) generating a crystal structure, a three-dimensional model of DOT1L, or obtaining the structure coordinates of DOT1L in complex with the candidate DOT1L inhibitor compound or complex, and (b) determining if the candidate DOT1L inhibitor compound or complex induces a conformational adaptation and/or a hydrophobic binding site of the DOT1L from the three-dimensional model.

In another aspect, the invention features a method of locating a binding site of a candidate DOT1L inhibitor compound or complex that modulates the activity of human DOT1L. The method comprises:

(a) obtaining X-ray diffraction data for a crystal of human DOT1L in complex with SAM or SAH or a compound of Formula (I);

(b) determining X-ray diffraction data for a crystal of human DOT1L in complex with candidate DOT1L inhibitor compound or complex or an analog or a derivative thereof;

(c) subtracting the X-ray diffraction data obtained in step (a) from the X-ray diffraction data obtained in step (b) to obtain the difference in the X-ray diffraction data;

(d) obtaining phases that correspond to X-ray diffraction data obtained in step (a);

(e) utilizing the phases obtained in step (d) and the difference in the X-ray diffraction data obtained in step (c) to compute a difference Fourier image of the candidate inhibitor; and (f) locating the binding site of the candidate inhibitor to human DOT1L based on the computations obtained in step (e).

In the above method of locating a binding site, the crystal in step (a) includes human DOT1L in complex with SAM or SAH, or Compound D16 or A2. In one embodiment, the DOT1L-inhibitor complex in step (b) comprises the hydrophobic pocket domain which comprises amino acid residues 139-312 of SEQ ID NO: 1 and the SAM binding pocket which comprises amino acid residues 135-241 of SEQ ID NO: 1.

In yet another aspect, the invention features a method for designing, identifying, and/or optimizing a candidate DOT1L inhibitor compound or complex that interacts with all or a part of a hydrophobic pocket domain which comprises amino acid residues 139-312 of SEQ ID NO: 1 and the SAM binding pocket of human DOT1L which comprises amino acid residues 135-241 of SEQ ID NO: 1. The method includes (a) producing the structure coordinates of the hydrophobic binding pocket of DOT1L in silico comprising the means for generating three-dimensional structural information from the coordinates;

(b) designing, selecting and/or optimizing the candidate DOT1L inhibitor compound or complex by performing a fitting operation between the candidate DOT1L inhibitor compound or complex and the three-dimensional structural information of all or part of the hydrophobic binding pocket or DOT1L protein; and (c) optionally employing computerized and/or reiterative steps.

The methods above include one or more of the following features:

For example, the SAM binding pocket of human DOT1L is characterized by the crystallography coordinates of human DOT1L amino acids Asp161, Gly163, Glu 186, Asp222, and Asn241. For example, the crystallography coordinates are within about a root mean square deviation of not more than about 3 Å (e.g., not more than about 2.5 Å, not more than about 2 Å, or not more than about 1.5 Å) from the backbone atoms of the amino acids according to Table S1 or S2.

For example, the SAM binding pocket of human DOT1L is characterized by the crystallography coordinates of human DOT1L amino acids Val135, Thr139, Asp161, Gly163, Gln168, Glu 186, Asp222, and Asn241. For example, the crystallography coordinates are within about a root mean square deviation of not more than about 3 Å (e.g., not more than about 2.5 Å, not more than about 2 Å, or not more than about 1.5 Å) from the backbone atoms of the amino acids according to Table S1 or S2. The SAM binding pocket of human DOT1L is further characterized by the crystallography coordinates of human DOT1L amino acid Phe223, for example, the crystallography coordinates are within about a root mean square deviation of not more than about 3 Å (e.g., not more than about 2.5 Å, not more than about 2 Å, or not more than about 1.5 Å) from the backbone atoms of the amino acid according to Table S1 or S2.

For example, the hydrophobic pocket domain of human DOT1L is characterized by the crystallography coordinates of human DOT1L amino acids Leu143, Met147, Phe239, and Tyr 312, for example, the crystallography coordinates are within about a root mean square deviation of not more than about 3 Å (e.g., not more than about 2.5 Å, not more than about 2 Å, or not more than about 1.5 Å) from the backbone atoms of the amino acids according to Table S1 or S2. The hydrophobic pocket domain of human DOT1L is further characterized by the crystallography coordinates of human DOT1L amino acid Thr139, Val144, Val169, Phe239, Val240, Asn241, Val267, Ser268, or Ser269, or combination thereof, for example, the crystallography coordinates are within about a root mean square deviation of not more than about 3 Å (e.g., not more than about 2.5 Å, not more than about 2 Å, or not more than about 1.5 Å) from the backbone atoms of the amino acid according to Table S1 or S2.

For example, the SAM binding pocket or the hydrophobic pocket domain of human DOT1L is characterized by the ligand plot as shown in any of FIGS. 6-9.

For example, the binding affinity ($K_i$) of the compound to human DOT1L is not greater than 50 μM, not greater than 10 μM, not greater than 5 μM, not greater than 2.5 μM, or not greater than 1 μM.

The term "associating with" refers to a condition of proximity between a chemical entity or compound, or portions thereof, and a binding pocket or binding site on a protein. The association may be non-covalent, wherein the juxtaposition is energetically favored by hydrogen bonding, hydrophobic, van der Waals or electrostatic interactions, or it may be covalent.

The term "binding pocket" or "binding site" of DOT1L refers to a region of DOT1L or a molecular complex comprising DOT1L that, as a result of the primary amino acid sequence of human DOT1L and/or its three-dimensional shape, favorably associates with another chemical entity. The term "pocket" includes, but is not limited to, a cleft, channel or site. The shape of a binding pocket may be largely pre-formed before binding of a chemical entity, may be formed simultaneously with binding of a chemical entity, or may be formed by the binding of another chemical entity to a different binding pocket of the molecule, which in turn induces a change in shape of the binding pocket.

The term "chemical entity" refers to chemical compounds, complexes of at least two chemical compounds, and fragments of such compounds or complexes. The chemical entity can be, for example, a ligand, substrate, nucleotide triphosphate, nucleotide diphosphate, phosphate, nucleotide, agonist, antagonist, inhibitor, antibody, peptide, protein or drug. In one embodiment, the chemical entity is an inhibitor or substrate for the active site.

The term "DOT1L complex" or the like refers to a molecular complex formed by associating the DOT1L protein with a chemical entity, for example, a ligand, a substrate, nucleotide triphosphate, nucleotide diphosphate, phosphate, an agonist or antagonist, inhibitor, antibody, drug or compound.

As used herein, the term "inhibitor complex" or the like refers to an association of two or more chemical compounds which can inhibit DOT1L activity. For example, an inhibitor complex is a complex of a compound having the adenosine-like moiety and another compound having a $R_9$ group and the complex does not have the linker group T.

The term "root mean square deviation" means the square root of the arithmetic mean of the squares of the deviations from the mean.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as carbon).

As used herein, the term "crystallography coordinates" or "structure coordinates" refers to mathematical coordinates that describe the positions of atoms in crystals of hDOT1L in Protein Data Bank (PDB) format, including X, Y, Z and B, for each atom. The diffraction data obtained from the crystals are used to calculate an electron density map of the repeating unit of the crystal. The electron density maps may be used to establish the positions (i.e. coordinates X, Y and Z) of the individual atoms within the crystal.

As used herein, the term "ligand" refers to any molecule, or chemical entity, which binds with or to DOT1L, a subunit of DOT1L, a domain of DOT1L, a target structural motif of DOT1L, or a fragment of DOT1L. Thus, ligands include, but are not limited to, modulators of DOT1L activity such as small molecule inhibitors, small molecule agonists, and small molecule inverse agonists, for example.

As used herein, the term "small molecule inhibitor" refers to ligands useful in the present invention having the ability to modulate a measurable amount of DOT1L activity. For example, a small molecule inhibitor has MW of less than 10,000 Daltons, and preferably less than 5,000 Daltons.

As used herein, the term "homolog" refers to the DOT1L protein molecule or the nucleic acid molecule which encodes the protein, or a functional domain from said protein from a first source having at least about 70% or 75% sequence identity, or at least about 80% sequence identity, or more preferably at least about 85% sequence identity, or even more preferably at least about 90% sequence identity, and most preferably at least about 95%, 97% or 99% sequence identity, with the amino acid sequence of the protein, the encoding nucleic acid molecule, or any functional domain thereof, from a second source. The second source may be a version of the molecule from the first source that has been genetically altered by any available means to change the primary amino acid or nucleotide sequence or may be from the same or a different species than that of the first source.

As used herein, the term "active site" refers to regions on DOT1L or a structural motif of DOT1L that are directly involved in the function or activity of human DOT1L.

The term "part of a binding pocket" refers to less than all of the amino acid residues that define the binding pocket. The structure coordinates of amino acid residues that constitute part of a binding pocket may be specific for defining the chemical environment of the binding pocket, or useful in designing fragments of an inhibitor that may interact with those residues. For example, the portion of amino acid residues may be key residues that play a role in ligand binding, or may be residues that are spatially related and define a three-dimensional compartment of the binding pocket. The amino acid residues may be contiguous or non-contiguous in primary sequence. In one embodiment, part of the binding pocket has at least two amino acid residues, preferably at least three, six, eight, ten, fourteen or fifteen amino acid residues.

In one aspect, a candidate which can be identified or optimized as a DOT1L inhibitor by the method of the invention is a compound of Formula (I) below or a pharmaceutically acceptable salt or ester thereof:

(I)

wherein,

Nuc is a nucleoside moiety (e.g., an adenosine-like moiety) or an analog or a derivative thereof, T is a linker group of a 6-10 carbon atoms, in which one or more carbon atoms are optionally replaced with a heteroatom and T is optionally substituted;

Nuc-T is capable of binding within the SAM binding pocket of human DOT1L which comprises amino acid residues 135-241 of SEQ ID NO: 1; and $R_9$ is a group such that $R_9$ induces a conformational adaptation in human DOT1L, wherein the conformational adaptation is the formation of a hydrophobic pocket domain which comprises amino acid residues 139-312 of SEQ ID NO: 1

The compound of Formula (I) may include one or more of the following features:

For example, $R_9$ is a group such that $R_9$ induces a residence time of the compound greater than 20 seconds in a complex formed of the compound and human DOT1L.

For example, $R_9$ is a group such that $R_9$ induces a conformational adaptation in human DOT1L, wherein the conformational adaptation is the formation of a hydrophobic pocket domain which is characterized by the crystallography coordinates of human DOT1L amino acids Leu143, Met147, Phe239, and Tyr 312, wherein the crystallography coordinates are within about a root mean square deviation of not more than about 2 Å from the backbone atoms of the amino acids according to Table S1 or S2;

For example, Nuc is an adenosine-like moiety.

For example, the adenosine-like moiety can be

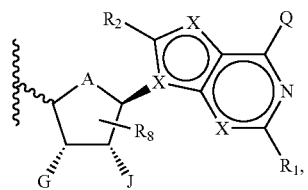

in which:

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl, C(O)—$C_1$-$C_6$ alkyl, or silyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

each X independently is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_1$ and $R_2$, independently is H, halo, hydroxyl, carboxyl, cyano, or $R_{S2}$, $R_{S2}$ being amino, $C_1$-$C_6$ alkoxyl, $C_1$-$C_6$ alkyl, $C_2$-$C_6$ alkenyl, $C_2$-$C_6$ alkynyl, or $C_3$-$C_8$ cycloalkyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl; and Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl.

For example, the adenosine-like moiety is

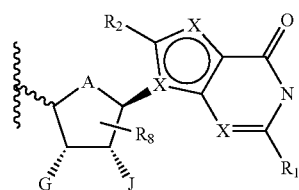

For example, the residence time of the compound in the DOT1L-compound complex is ≥50 seconds, ≥100 seconds, ≥2 minutes, ≥10 minutes, ≥30 minutes, ≥1 hr, ≥5 hr, ≥10 hr, ≥20 hr, or ≥30 hr.

For example, the compound has a residence time in the DOT1L-compound complex not shorter than that of Compound D16.

For example, the compound has a residence time in the DOT1L-compound complex not shorter than that of Compound A2.

For example, the SAM binding pocket of human DOT1L is characterized by the crystallography coordinates of human DOT1L amino acids Asp161, Gly163, Glu 186, Asp222, and Asn241. For example, the crystallography coordinates are within about a root mean square deviation of not more than about 3 Å (e.g., not more than about 2.5 Å, not more than about 2 Å, or not more than about 1.5 Å) from the backbone atoms of the amino acids according to Table S1 or S2.

For example, the SAM binding pocket of human DOT1L is characterized by the crystallography coordinates of human DOT1L amino acids Val135, Thr139, Asp161, Gly163, Gln168, Glu 186, Asp222, and Asn241. For example, the crystallography coordinates are within about a root mean square deviation of not more than about 3 Å (e.g., not more than about 2.5 Å, not more than about 2 Å, or not more than about 1.5 Å) from the backbone atoms of the amino acids according to Table S1 or S2. The SAM binding pocket of human DOT1L is further characterized by the crystallography coordinates of human DOT1L amino acid Phe223. For example, the crystallography coordinates are within about a root mean square deviation of not more than about 3 Å (e.g., not more than about 2.5 Å, not more than about 2 Å, or not more than about 1.5 Å) from the backbone atoms of the amino acid according to Table S1 or S2.

For example, the hydrophobic pocket domain of human DOT1L is characterized by the crystallography coordinates of human DOT1L amino acids Leu143, Met147, Phe239, and Tyr 312. For example, the crystallography coordinates are within about a root mean square deviation of not more than about 3 Å (e.g., not more than about 2.5 Å, not more than about 2 Å, or not more than about 1.5 Å) from the backbone atoms of the amino acids according to Table S1 or S2. The hydrophobic pocket domain of human DOT1L is further characterized by the crystallography coordinates of human DOT1L amino acid Thr139, Val144, Val169, Phe239, Val240, Asn241, Val267, Ser268, or Ser269, or combination thereof, for example, the crystallography coordinates are within about a root mean square deviation of not more than about 3 Å (e.g., not more than about 2.5 Å, not more than about 2 Å, or not more than about 1.5 Å) from the backbone atoms of the amino acid according to Table S1 or S2.

For example, the SAM binding pocket or the hydrophobic pocket domain of human DOT1L is characterized by the ligand plot as shown in any of FIGS. 6-9.

For example, the binding affinity ($K_i$) of the compound to human DOT1L is not greater than 50 µM, not greater than 10 µM, not greater than 5 µM, not greater than 2.5 µM, or not greater than 1 µM.

For example, in Formula (I), $R_9$ comprises $C_6$-$C_{10}$ aryl or 5 to 10-membered heteroaryl optionally substituted with one or more substituents selected from the group consisting of unsubstituted or substituted t-butyl, $CF_3$, cyclohexyl, $C_6$-$C_{10}$ aryl, and 5 to 10-membered heteroaryl.

For example, in Formula (I), $R_9$ is selected from the group consisting of

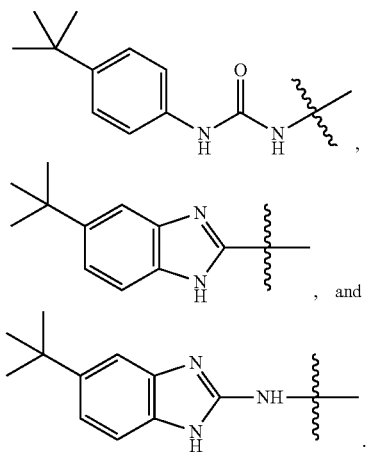 [SMILES: *NC(=O)Nc1ccc(C(C)(C)C)cc1 ; *c1nc2cc(C(C)(C)C)ccc2[nH]1 ; *Nc1nc2cc(C(C)(C)C)ccc2[nH]1]

For example, the compound is of Formula (II):

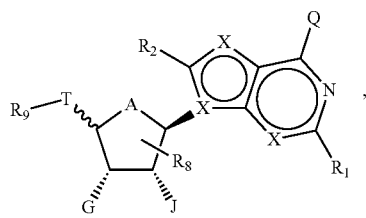

wherein,

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl, C(O)—$C_1$-$C_6$ alkyl, or silyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

each X independently is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_1$ and $R_2$, independently is H, halo, hydroxyl, carboxyl, cyano, or $R_{S2}$, $R_{S2}$ being amino, $C_1$-$C_6$ alkoxyl, $C_1$-$C_6$ alkyl, $C_2$-$C_6$ alkenyl, $C_2$-$C_6$ alkynyl, or $C_3$-$C_8$ cycloalkyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl; and Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl.

In Formula (I) or (II), T is —$CH_2$-$L_1$-$L_2$-$L_3$-, with $L_3$ connected to $R_9$, wherein:

$L_1$ is N(Y), S, SO, or $SO_2$;

$L_2$ is CO or absent when $L_1$ is N(Y), or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, carboxyl, cyano, $C_1$-$C_6$ alkoxyl, $C_1$-$C_6$ alkylsulfonyl, $C_3$-$C_8$ cycloalkyl, $C_6$-$C_{10}$ aryl, 4 to 8-membered heterocycloalkyl, 5 to 6-membered heteroaryl, $OR_{d'}$, $OCOR_{d'}$, and $N(R_{d'})_2$, and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl; each $R_{d'}$ independently being H, $C_1$-$C_6$ alkyl, silyl, $C_1$-$C_6$ alkyl-$C_3$-$C_8$ cycloalkyl, $C_6$-$C_{10}$ aryl, 5 to 6-membered heteroaryl, aralkyl, or heteroaralkyl;

$L_3$ is —$(CR_4R_5)_n(CR_6R_7)_m$— or —$(CR_4R_5)_n$-unsubstituted or substituted $C_3$-$C_8$ cycloalkyl-$(CR_6R_7)_m$—, with $(CR_6R_7)_m$ connected to $R_9$;

each of $R_4$, $R_5$, $R_6$, and $R_7$, independently, is H, halo, hydroxyl, carboxyl, cyano, or $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl; or two geminal $R_4$ and $R_5$ or two geminal $R_6$ and $R_7$ taken together are ethylene, propylene or butylene;

m is 0, 1, or 2; and n is 0, 1, or 2.

For example, in Formula (I) or (II), $R_9$ is

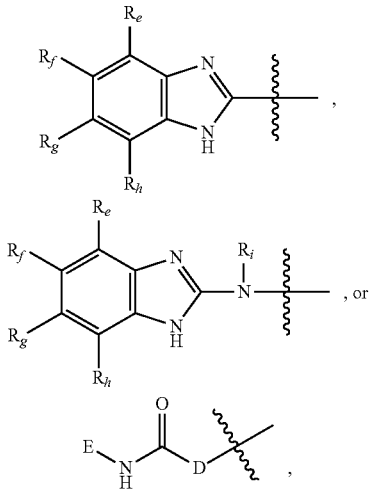

, or in which:
each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_1$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{14}$ carbocycle or 4 to 14-membered heterocycle, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl.

For example, the compound is of formula (IIIa) or (IIIb):

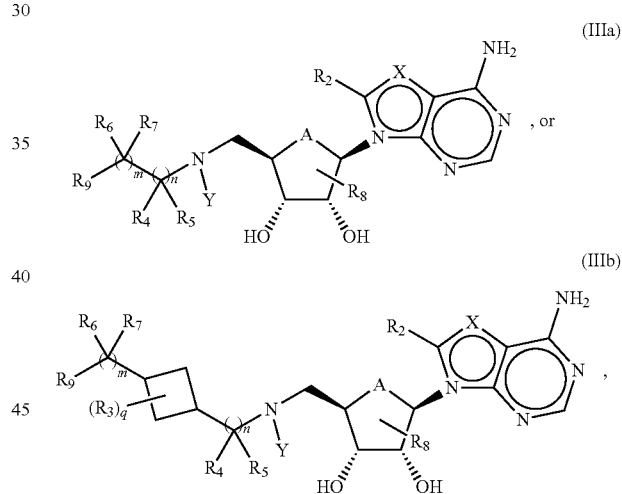

wherein $R_3$ is H, halo, hydroxyl, carboxyl, cyano, or $R_{S2}$, and q is 0, 1, 2, 3, or 4.

For example, the compound is of formula (IIIa) and $R_9$ is

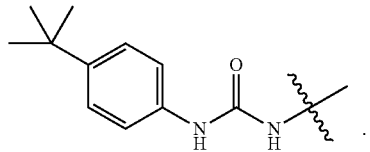 [SMILES: *NC(=O)Nc1ccc(C(C)(C)C)cc1]

.

For example, the compound is of formula (IIIb) and $R_9$ is

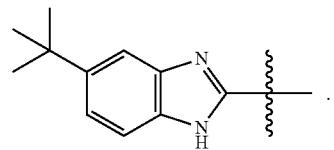

.

Compounds that are identified as DOT1L inhibitors by the method described herein can also include those of Formula (IIa) or (IIb)

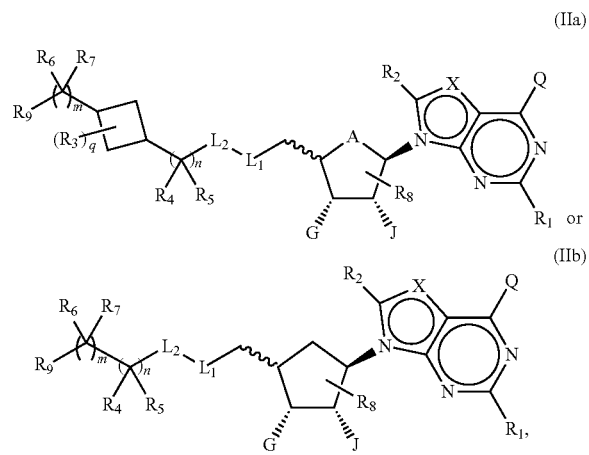

or a pharmaceutically acceptable salt or ester thereof, wherein:

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

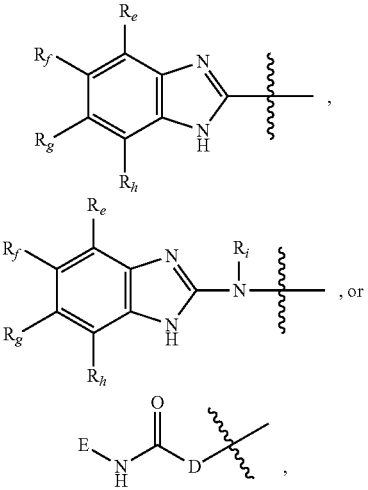

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_1$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;
m is 0, 1, or 2; and
n is 0, 1, or 2.

For example, the sum of m and n is at least 1.
For example, m is 1 or 2 and n is 0.
For example, m is 2 and n is 0
For example, A is $CH_2$.
For example, A is O.
For example, $L_1$ is N(Y).
For example, $L_1$ is SO or $SO_2$.
For example, Y is $R_d$.
For example, $R_d$ is $C_1$-$C_6$ alkyl.
For example, $L_2$ is absent.
For example, each of G and J independently is $OR_a$.
For example, $R_a$ is H.
For example, $R_9$ is

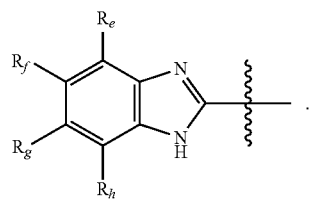

For example, $R_9$ is

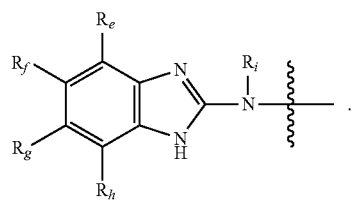

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, $R_i$ is H or $C_1$-$C_6$ alkyl (e.g., methyl, ethyl, n-propyl, i-propyl, n-butyl, s-butyl, t-butyl, n-pentyl, s-pentyl and n-hexyl).

For example,

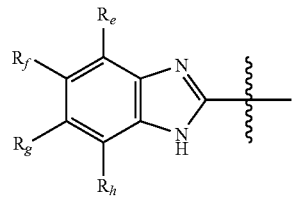

is unsubstituted benzimidazolyl or one of the following groups:

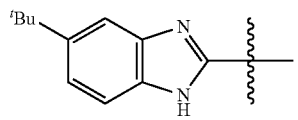

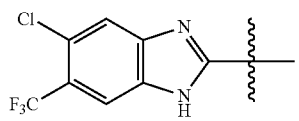

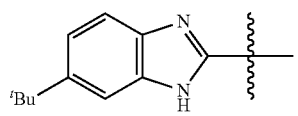

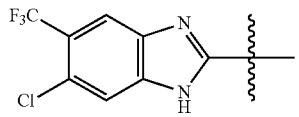

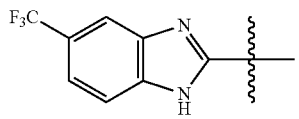

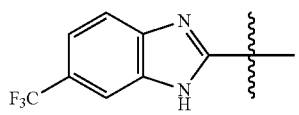

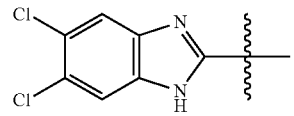

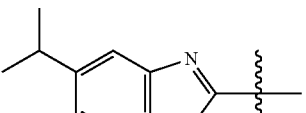

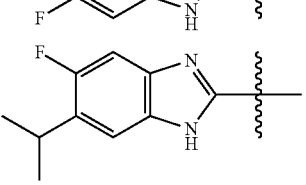

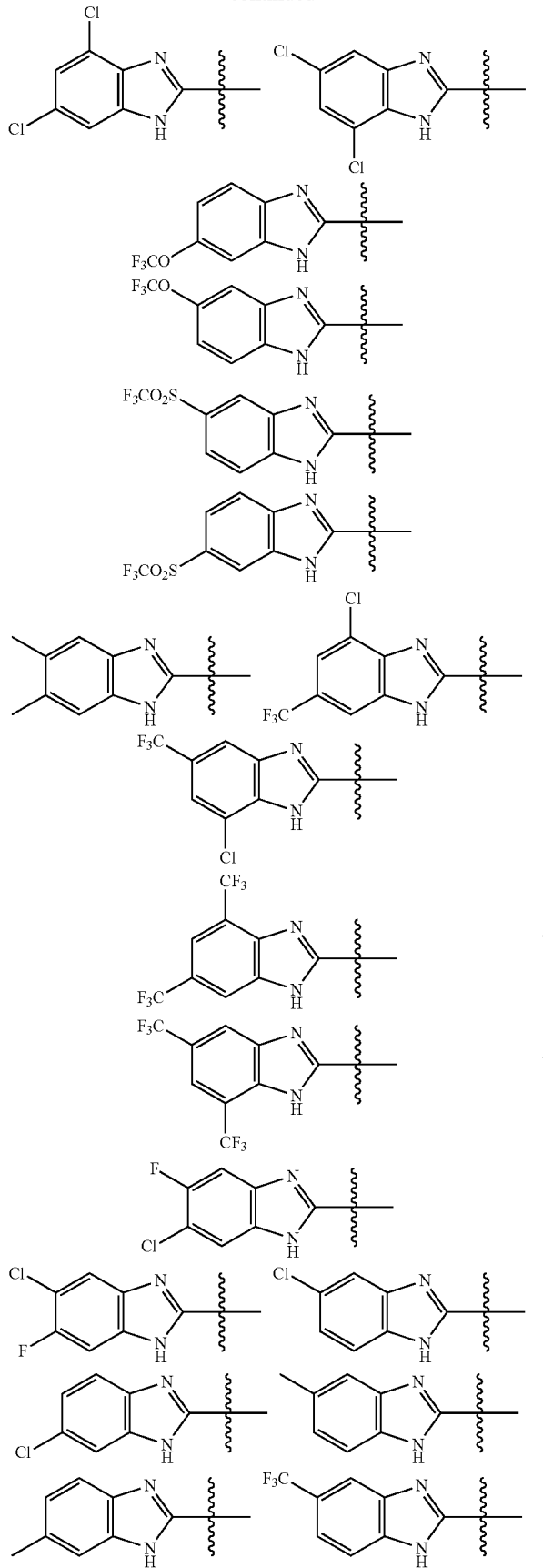
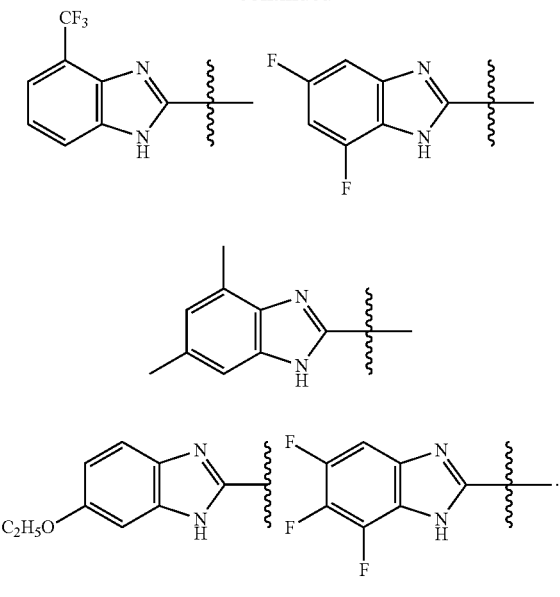

For example, $R_9$ is

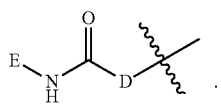

For example, D is O.

For example, D is $NR_j$.

For example, $R_j$ is H.

For example, D is $CR_jR_k$.

For example, each of $R_j$ and $R_k$ is H.

For example, E is $-M_3-T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is
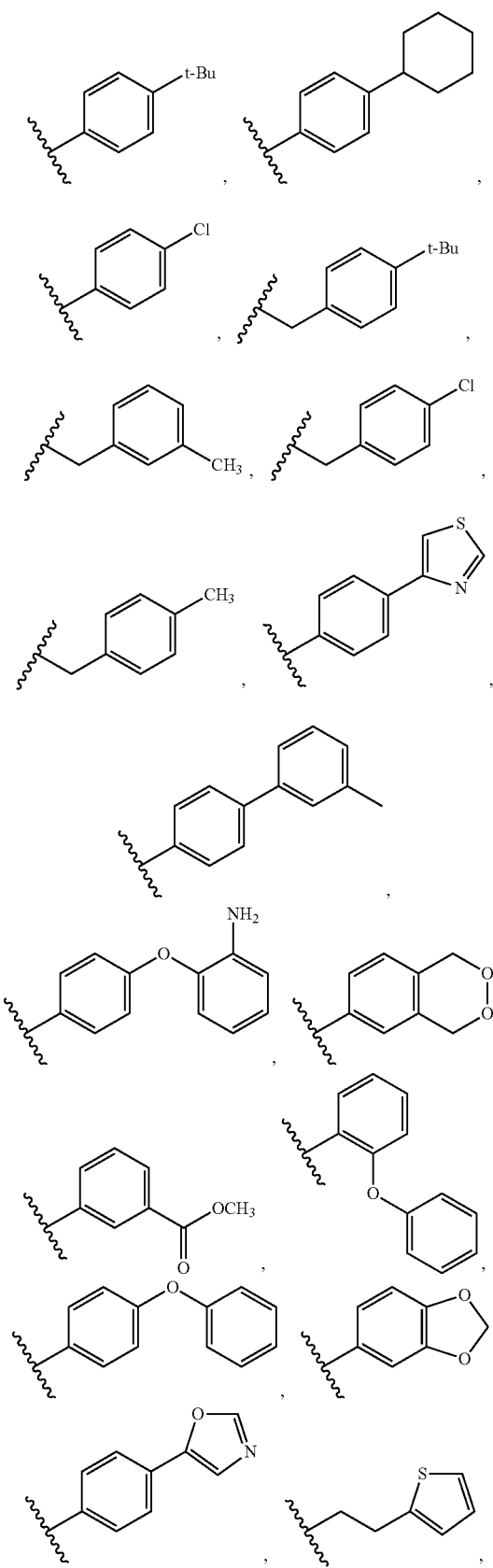
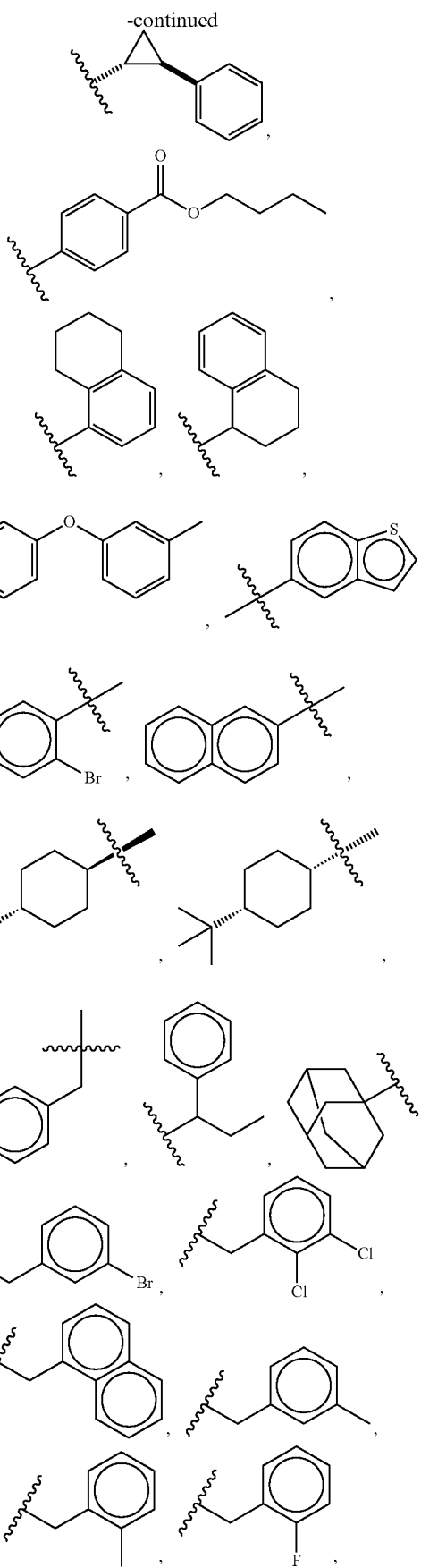

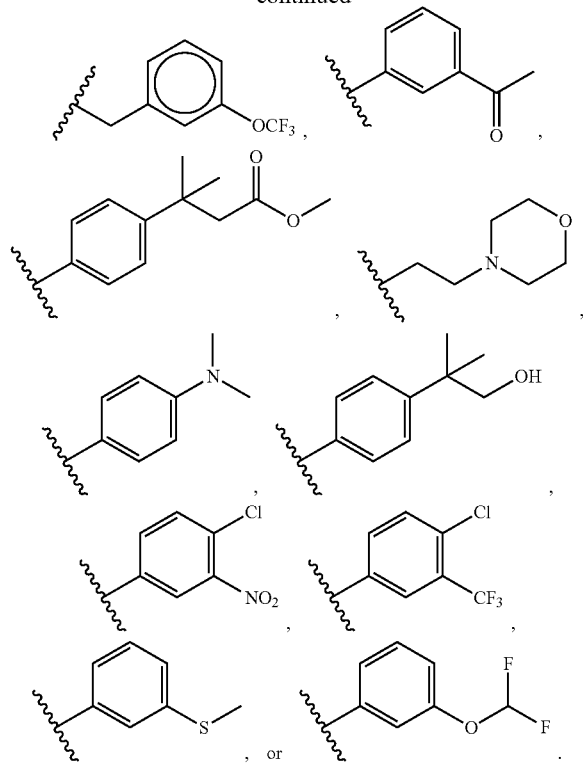

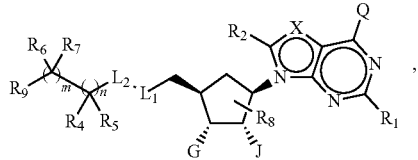

or a pharmaceutically acceptable salt or ester thereof, wherein the variables are defined herein as for Formula (IIa) or (IIb).

The compound of Formula (II) include those of Formula (IIIa), or (IIIb):

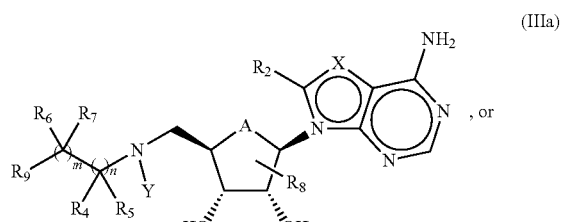

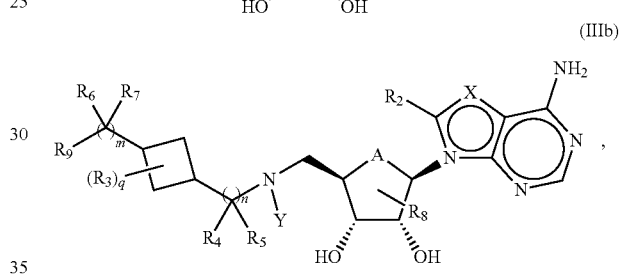

or a pharmaceutically acceptable salt or ester thereof, wherein:

A is O or $CH_2$;

Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl, or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, For example, X is N.
For example, X is $CR_x$.
For example, X is CH.
For example, Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl.
For example, Q is H.
For example, $R_1$, $R_2$, $R_3$, $R_4$, $R_5$, $R_6$, $R_7$, and $R_8$ are each H.
For example, when $R_8$ is halo and is attached to the same carbon atom as J, then J is not hydroxyl.
For example, when $R_8$ is halo and is attached to the same carbon atom as G, then G is not hydroxyl.
For example, $T_2$ is not halo when $M_2$ is $SO_2$, SO, S, CO or O.
For example, $T_2$ is a 4-8 membered heterocycloalkyl which is bound to $M_2$ via a heteroatom.
For example, $T_2$ is a 4-8 membered heterocycloalkyl which is bound to $M_2$ via a N atom.
For example, $T_2$ is a 4-8 membered heterocycloalkyl which is bound to $M_2$ via a C atom.

Compounds that are identified as DOT1L inhibitors by the method described herein can also include those of Formula (IIc) or (IId):

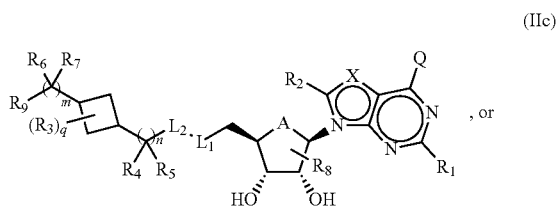

$C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

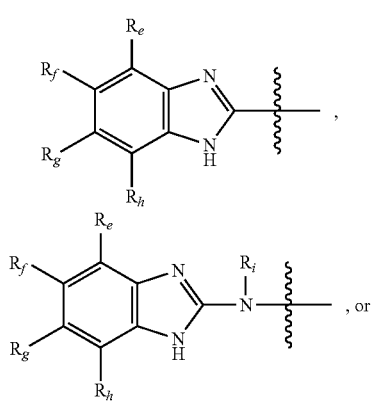

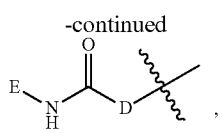

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;

m is 0, 1, or 2; and n is 0, 1, or 2.

For example, the sum of m and n is at least 1.

For example, m is 1 or 2 and n is 0.

For example, m is 2 and n is 0

For example, A is $CH_2$.

For example, A is O.

For example, $L_1$ is N(Y).

For example, $L_1$ is SO or $SO_2$.

For example, Y is $R_d$.

For example, $R_d$ is $C_1$-$C_6$ alkyl.

For example, $L_2$ is absent.

For example, R₉ is

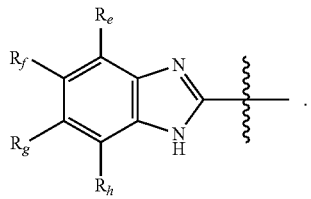

For example, R₉ is

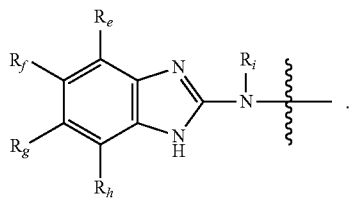

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, $R_1$ is H or $C_1$-$C_6$ alkyl (e.g., methyl, ethyl, n-propyl, i-propyl, n-butyl, s-butyl, t-butyl, n-pentyl, s-pentyl or n-hexyl).

For example,

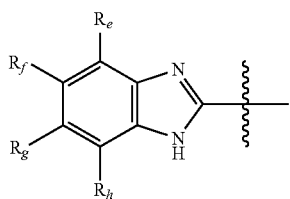

is unsubstituted benzimidazolyl or one of the following groups:

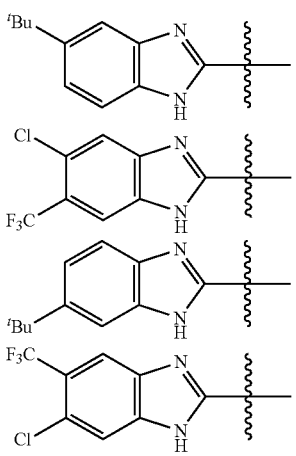

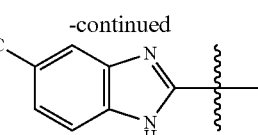
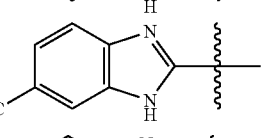
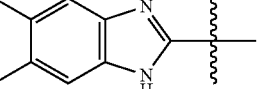
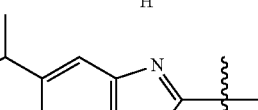
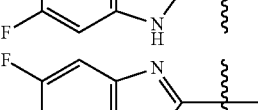
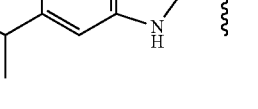
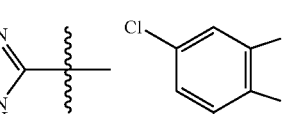
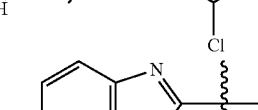
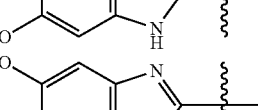
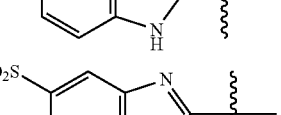
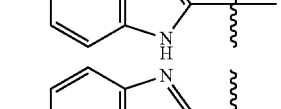
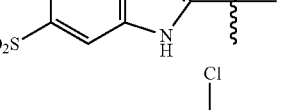
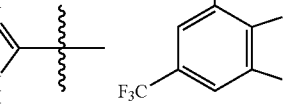
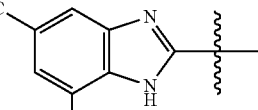
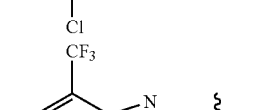
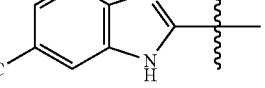

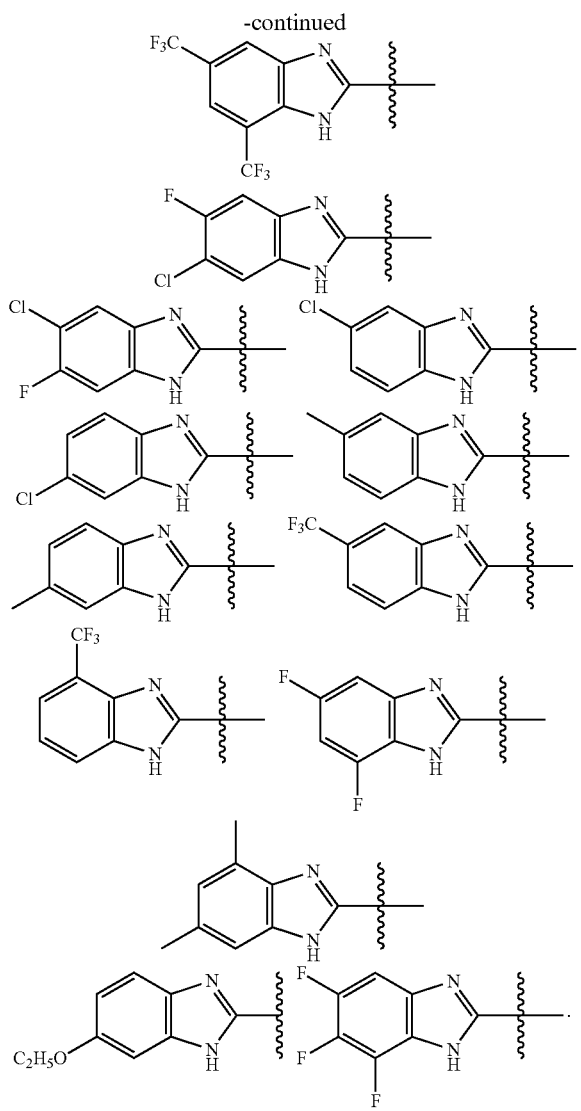

For example, R$_9$ is

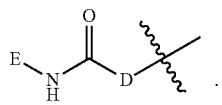

For example, D is O.
For example, D is NR$_j$.
For example, R$_j$ is H.
For example, D is CR$_j$R$_k$.
For example, each of R$_j$ and R$_k$ is H.
For example, E is -M$_3$-T$_3$, in which M$_3$ is a bond or C$_1$-C$_3$ alkyl linker, T$_3$ is phenyl, naphthyl, thienyl, cyclopropyl, or cyclohexyl, and T$_3$ is optionally substituted with one or more substituents selected from the group consisting of halo, hydroxyl, thiol, carboxyl, cyano, nitro, C$_1$-C$_6$ alkyl, C$_2$-C$_6$ alkenyl, C$_2$-C$_6$ alkynyl, C$_1$-C$_6$ alkoxyl, C$_1$-C$_6$ haloalkyl, C$_1$-C$_6$ haloalkoxyl, C$_1$-C$_6$ alkylthio, C$_1$-C$_6$ alkylsulfonyl, C$_1$-C$_6$ alkylcarbonyl, C$_1$-C$_6$ alkoxycarbonyl, oxo, amino, mono-C$_1$-C$_6$ alkylamino, di-C$_1$-C$_6$ alkylamino, C$_3$-C$_8$ cycloalkyl, C$_4$-C$_{12}$ alkylcycloalkyl, C$_6$-C$_{10}$ aryl, C$_6$-C$_{10}$ aryloxyl, C$_7$-C$_{14}$ alkylaryl, C$_6$-C$_{10}$ aminoaryloxyl, C$_6$-C$_{10}$ aryl-thio, 4 to 6-membered heterocycloalkyl optionally substituted with C$_1$-C$_4$ alkyl, 5 to 6-membered heteroaryl optionally substituted with C$_1$-C$_4$ alkyl, and C$_1$-C$_6$ alkyl that is substituted with hydroxy, C$_1$-C$_6$ alkoxycarbonyl, C$_3$-C$_8$ cycloalkyl, C$_6$-C$_{10}$ aryl, 4 to 6-membered heterocycloalkyl, or 5 to 6-membered heteroaryl.

For example, T$_3$ is phenyl optionally substituted with one or more substituents selected from the group consisting of halo, hydroxyl, carboxyl, cyano, nitro, C$_1$-C$_6$ alkyl (e.g., methyl, ethyl, n-propyl, i-propyl, n-butyl, s-butyl, t-butyl, n-pentyl, s-pentyl and n-hexyl), C$_1$-C$_6$ alkoxyl, C$_1$-C$_6$ haloalkyl, C$_1$-C$_6$ haloalkoxyl, C$_1$-C$_6$ alkylsulfonyl, C$_6$-C$_{10}$ aryl (e.g., phenyl or naphthyl), and C$_6$-C$_{10}$ aryloxyl, and C$_7$-C$_{14}$ alkylaryl.

For example, E is

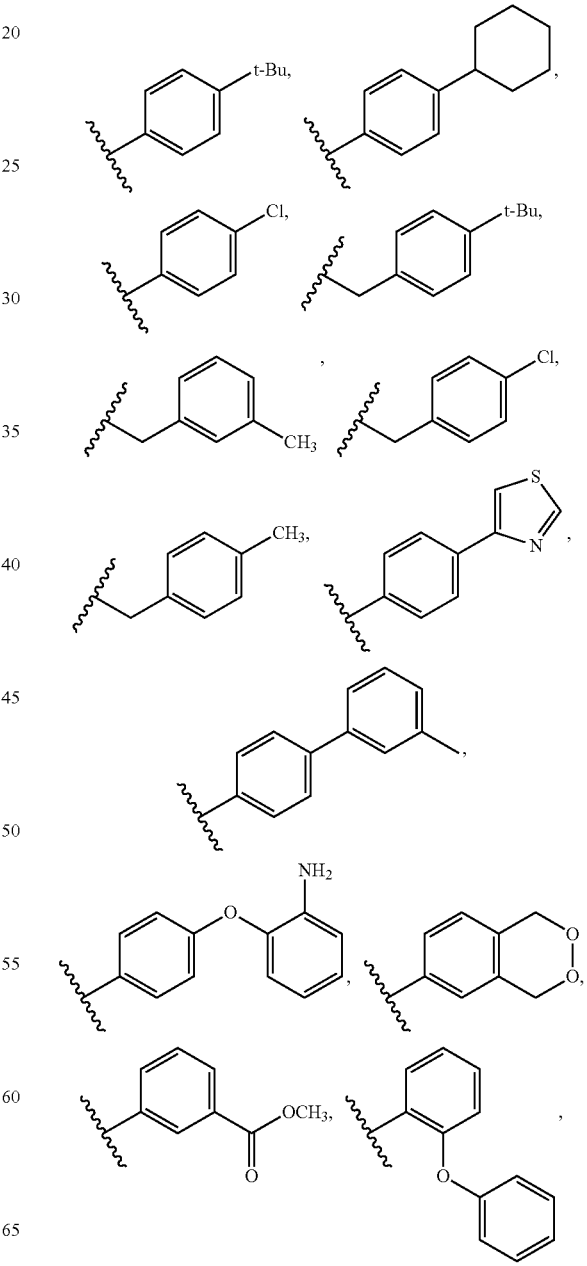

For example, X is N.
For example, X is CR$_x$.
For example, X is CH.
For example, Q is NH$_2$ or NHR$_b$, in which R$_b$ is -M$_1$-T$_1$, M$_1$ being a bond or C$_1$-C$_6$ alkyl linker and T$_1$ being C$_3$-C$_8$ cycloalkyl.
For example, Q is H.
For example, R$_1$, R$_2$, R$_3$, R$_4$, R$_5$, R$_6$, R$_7$, and R$_8$ are each H.
For example, when R$_8$ is halo and is attached to the same carbon atom as J, then J is not hydroxyl.
For example, when R$_8$ is halo and is attached to the same carbon atom as G, then G is not hydroxyl.
For example, T$_2$ is not halo when M$_2$ is SO$_2$, SO, S, CO or O.
For example, T$_2$ is a 4-8 membered heterocycloalkyl which is bound to M$_2$ via a heteroatom.

For example, $T_2$ is a 4-8 membered heterocycloalkyl which is bound to $M_2$ via a N atom.

For example, $T_2$ is a 4-8 membered heterocycloalkyl which is bound to $M_2$ via a C atom.

The present invention provides the compounds of Formula (IVa), (IVb), (IVd), or (IVe):

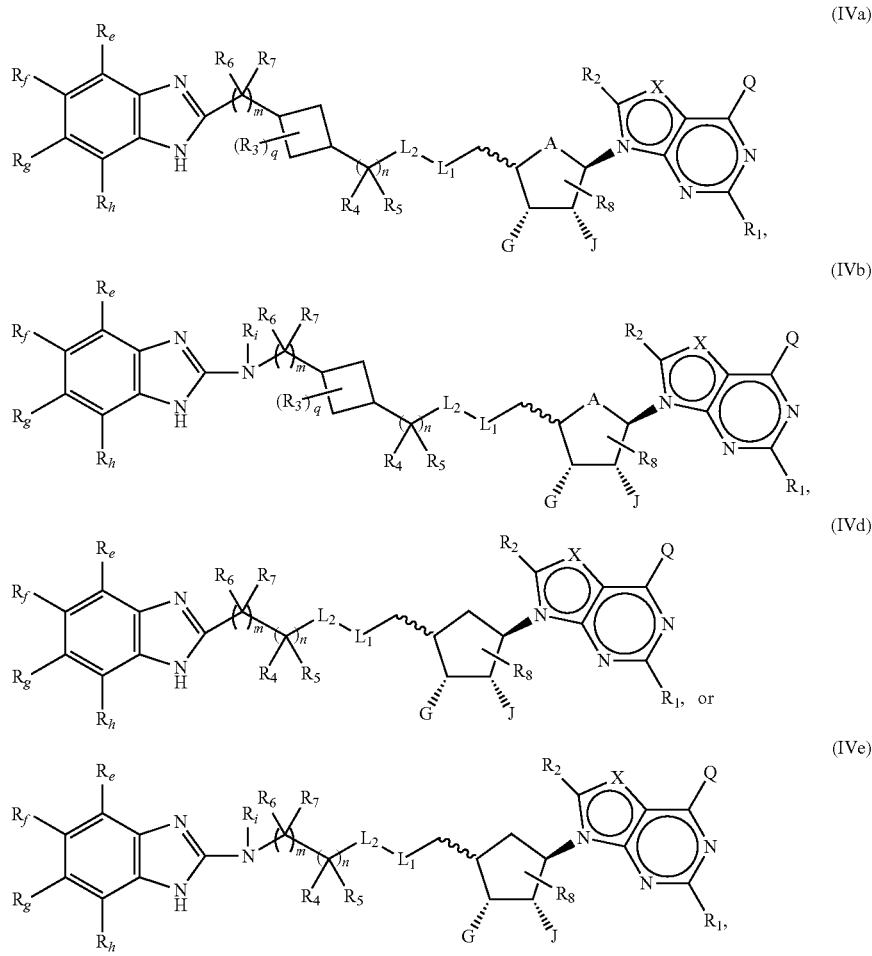

or a pharmaceutically acceptable salt or ester thereof, wherein:

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

L₁ is N(Y), S, SO, or SO₂;

L₂ is CO or absent when L₁ is N(Y) or L₂ is absent when L₁ is S, SO, or SO₂, in which Y is H, $R_d$, SO₂$R_d$, or COR$_d$ when L₂ is absent, or Y is H or $R_d$ when L₂ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

each of $R_e$, $R_f$, $R_g$, and $R_h$, independently is -$M_2$-$T_2$, in which $M_2$ is a bond, SO₂, SO, S, CO, CO₂, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_t$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

q is 0, 1, 2, 3, or 4;
m is 0, 1, or 2; and
n is 0, 1, or 2.

For example, the sum of m and n is at least 1.
For example, m is 1 or 2 and n is 0.
For example, m is 2 and n is 0
For example, A is CH₂.
For example, A is O.
For example, L₁ is N(Y).
For example, L₁ is SO or SO₂.
For example, Y is $R_d$.
For example, $R_d$ is $C_1$-$C_6$ alkyl.
For example, L₂ is absent.
For example, each of G and J independently is $OR_a$.
For example, $R_a$ is H.
For example, at least one of $R_e$, $R_f$, $R_g$, and $R_h$ is halo (such as F, Cl, and Br), $C_1$-$C_6$ alkoxyl optionally substituted with one or more halo (such as OCH₃, OCH₂CH₃, O-iPr, and OCF₃), $C_1$-$C_6$ alkylsulfonyl optionally substituted with one or more halo (such as SO₂CF₃), or $C_1$-$C_6$ alkyl optionally substituted with one or more halo (such as CH₃, i-propyl, n-butyl, and CF₃).

For example, $R_1$ is H or $C_1$-$C_6$ alkyl (e.g., methyl, ethyl, n-propyl, i-propyl, n-butyl, s-butyl, t-butyl, n-pentyl, s-pentyl and n-hexyl).

For example,

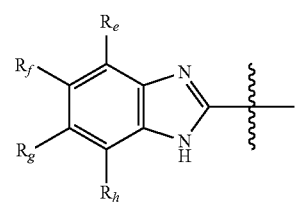

is unsubstituted benzimidazolyl or one of the following groups:

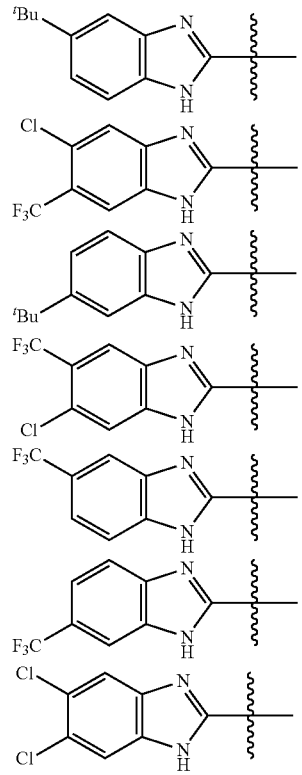

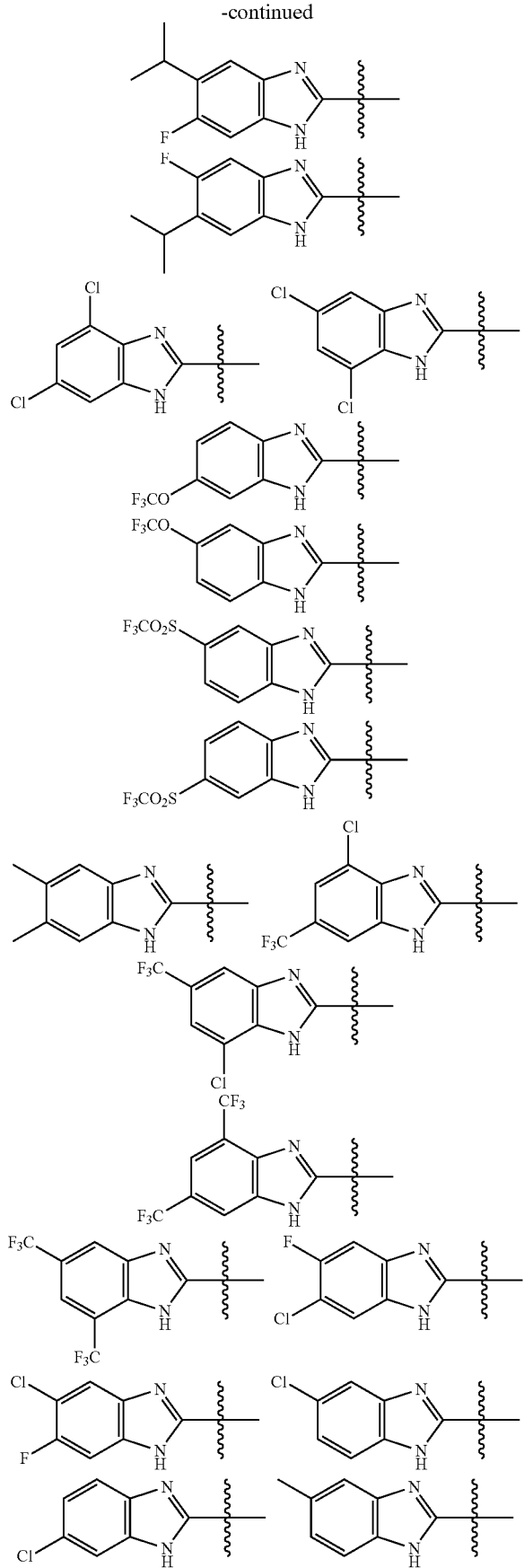

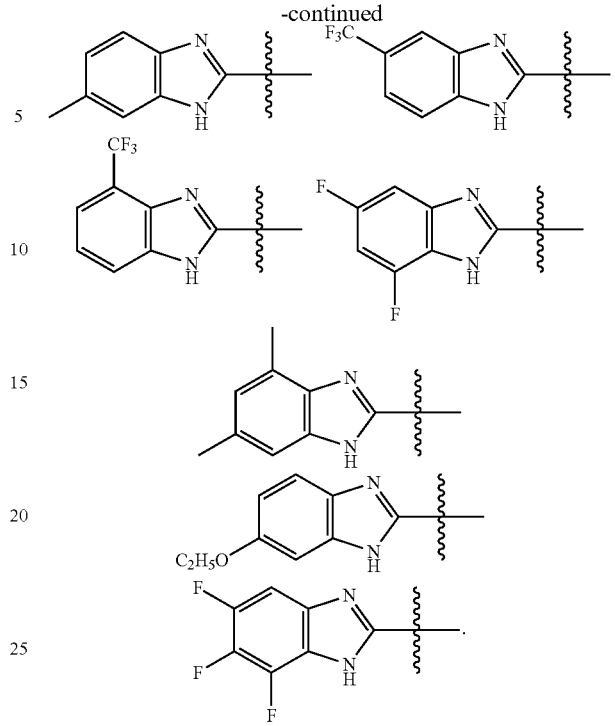

For example, X is N.

For example, X is $CR_x$.

For example, X is CH.

For example, Q is $NH_2$ or $NHR_b$, in which $R_b$ is $-M_1-T_1$, $M_1$ being a bond or $C_1$-$C_6$ alkyl linker and $T_1$ being $C_3$-$C_8$ cycloalkyl.

For example, Q is H.

For example, $R_1$, $R_2$, $R_3$, $R_4$, $R_5$, $R_6$, $R_7$, and $R_8$ are each H.

For example, when $R_8$ is halo and is attached to the same carbon atom as J, then J is not hydroxyl.

For example, when $R_8$ is halo and is attached to the same carbon atom as G, then G is not hydroxyl.

For example, $T_2$ is not halo when $M_2$ is $SO_2$, SO, S, CO or O.

For example, $T_2$ is a 4-8 membered heterocycloalkyl which is bound to $M_2$ via a heteroatom.

For example, $T_2$ is a 4-8 membered heterocycloalkyl which is bound to $M_2$ via a N atom.

For example, $T_2$ is a 4-8 membered heterocycloalkyl which is bound to $M_2$ via a C atom.

The present invention provides the compounds of Formula (IVc) or (IVf):

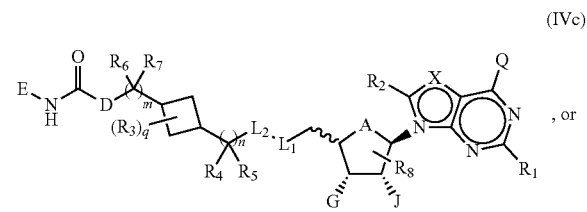

(IVc)

, or (IVf)

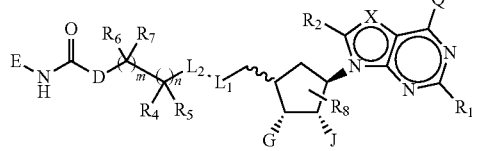

or a pharmaceutically acceptable salt or ester thereof, wherein:
A is O or $CH_2$;
each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;
Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
$L_1$ is N(Y), S, SO, or $SO_2$;
$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;
each of $R_1$, $R_2$, $R_3$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;
$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;
D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring;
E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxy, $C_7$-$C_{14}$ alkylaryl, $C_6$-$C_{10}$ aminoaryloxy, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;
q is 0, 1, 2, 3, or 4;
m is 0, 1, or 2; and
n is 0, 1, or 2.
For example, the sum of m and n is at least 1.
For example, m is 1 or 2 and n is 0.
For example, m is 2 and n is 0
For example, A is $CH_2$.
For example, A is O.
For example, $L_1$ is N(Y).
For example, $L_1$ is SO or $SO_2$.
For example, Y is $R_d$.

For example, $R_d$ is $C_1$-$C_6$ alkyl.

For example, $L_2$ is absent.

For example, each of G and J independently is $OR_a$.

For example, $R_a$ is H.

For example, D is O.

For example, D is $NR_j$.

For example, $R_j$ is H.

For example, D is $CR_jR_k$.

For example, each of $R_j$ and $R_k$ is H.

For example, E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

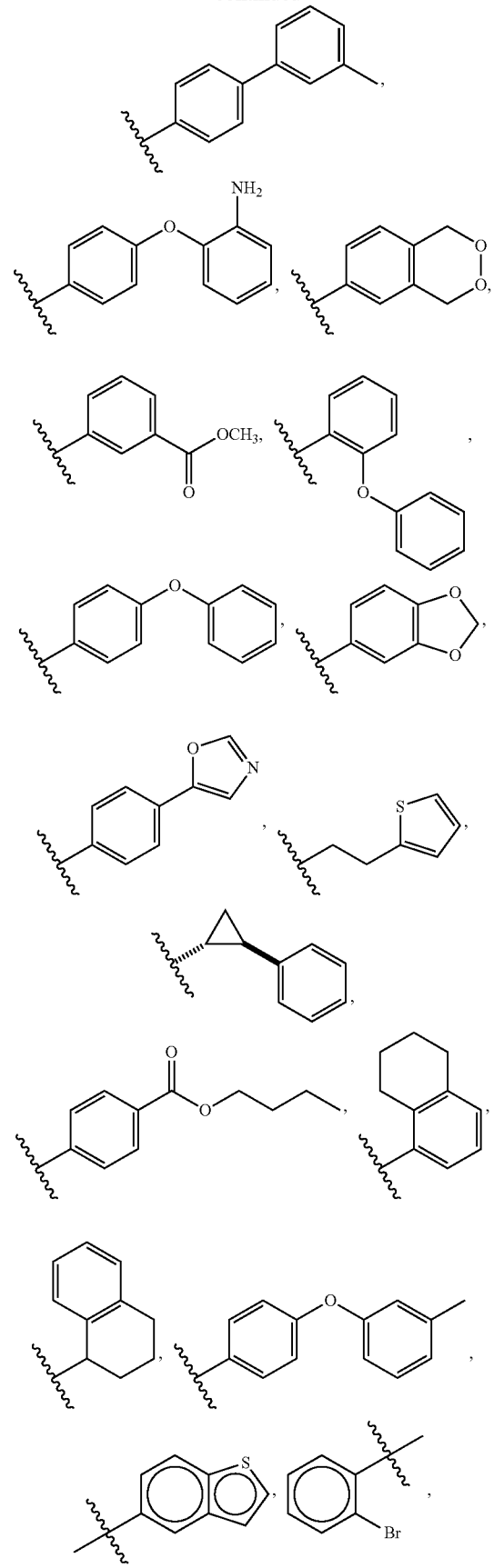

47
-continued

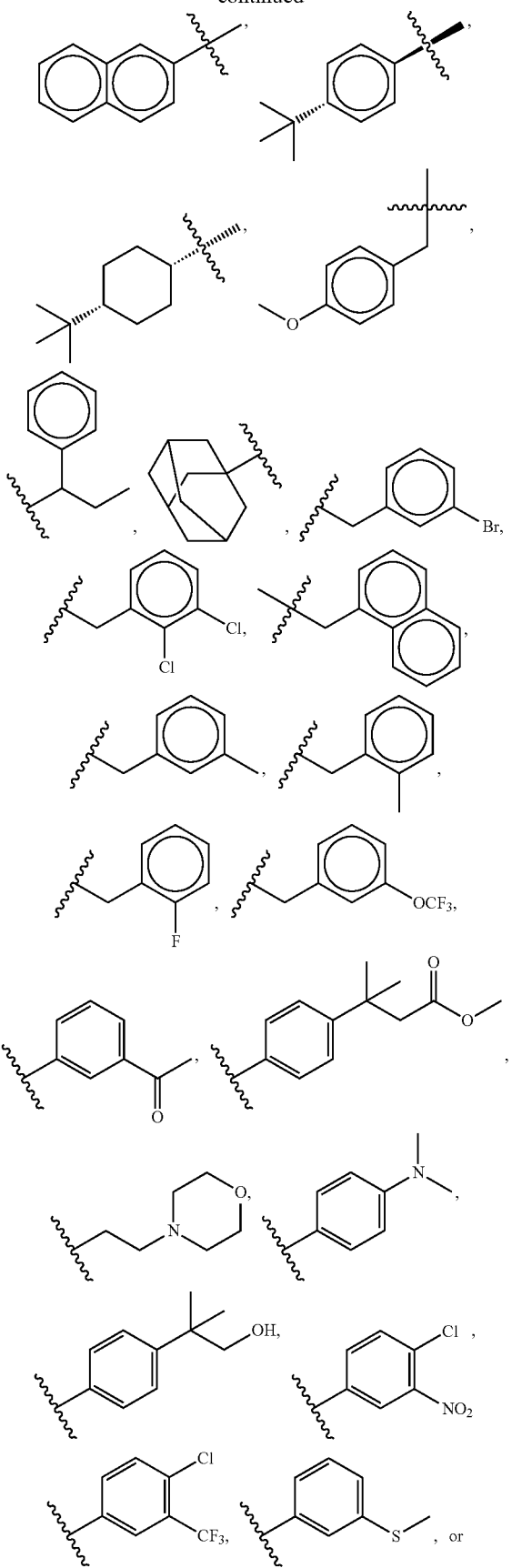

48
-continued

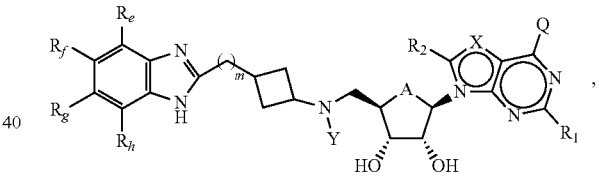

For example, X is N.
For example, X is $CR_x$.
For example, X is CH.
For example, Q is $NH_2$ or $NHR_b$, in which $R_b$ is $-M_1-T_1$, $M_1$ being a bond or $C_1$-$C_6$ alkyl linker and $T_1$ being $C_3$-$C_8$ cycloalkyl.
For example, Q is H.
For example, $R_1$, $R_2$, $R_3$, $R_4$, $R_5$, $R_6$, $R_7$, and $R_8$ are each H.
For example, when Ibis halo and is attached to the same carbon atom as J, then J is not hydroxyl.
For example, when $R_8$ is halo and is attached to the same carbon atom as G, then G is not hydroxyl.
For example, $T_2$ is not halo when $M_2$ is $SO_2$, SO, S, CO or O.
For example, $T_2$ is a 4-8 membered heterocycloalkyl which is bound to $M_2$ via a heteroatom.
For example, $T_2$ is a 4-8 membered heterocycloalkyl which is bound to $M_2$ via a N atom.
For example, $T_2$ is a 4-8 membered heterocycloalkyl which is bound to $M_2$ via a C atom.
The invention also relates to a compound of Formula (IV) or its N-oxide or a pharmaceutically acceptable salt thereof:

(IV)

wherein A is O or $CH_2$;
Q is H, $NH_2$, $NHR_b$, $NR_bR_c$, $R_b$, =O, OH, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or $-M_1-T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

Y is H, $R_d$, $SO_2R_d$, or $COR_d$, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$ and $R_2$ independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, and m is 0, 1, or 2.

For example, A is O. In certain compounds of Formula (IV), A is O and m is 2.

In certain compounds of Formula (IV), X is N.

For example, in certain compounds, Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl For example, in certain compounds of Formula (IV), $R_1$ and $R_2$ are each H.

In certain compounds of Formula (IV), Y is $R_d$. For example, $R_d$ is $C_1$-$C_6$ alkyl optionally substituted with $C_3$-$C_8$ cycloalkyl or halo. For example, $R_d$ is $C_3$-$C_8$ cycloalkyl optionally substituted with $C_1$-$C_6$ alkyl or halo.

The invention also relates to a compound of Formula (IV), wherein at least one of $R_e$, $R_f$, $R_g$, and $R_h$ is halo, $C_1$-$C_6$ alkoxyl optionally substituted with one or more halo; $C_1$-$C_6$ alkylsulfonyl optionally substituted with one or more halo; $C_1$-$C_6$ alkyl optionally substituted with one or more substituents selected from CN, halo, $C_3$-$C_8$ cycloalkyl, hydroxy, and $C_1$-$C_6$ alkoxyl; $C_3$-$C_8$ cycloalkyl optionally substituted with one or more $C_1$-$C_6$ alkyl or CN; or 4 to 8-membered heterocycloalkyl optionally substituted with one or more substituents selected from CN, halo, hydroxy, $C_1$-$C_6$ alkyl and $C_1$-$C_6$ alkoxyl. For example, the compound of Formula (IV) has at least one of $R_e$, $R_f$, $R_g$, and $R_h$ selected from F; Cl; Br; $CF_3$; $OCF_3$; $SO_2CF_3$; oxetanyl optionally substituted with one or more substituents selected from CN, halo, hydroxy, $C_1$-$C_6$ alkyl and $C_1$-$C_6$ alkoxyl; $C_3$-$C_8$ cycloalkyl optionally substituted with one or more substituents selected from $C_1$-$C_4$ alkyl; and $C_1$-$C_4$ alkyl optionally substituted with one or more substituents selected from halo, $C_3$-$C_8$ cycloalkyl, hydroxy and $C_1$-$C_6$ alkoxyl.

For example, the invention relates to compounds of Formula (IV) where at least one of $R_f$ and $R_g$ is alkyl, optionally substituted with hydroxyl. For example, the invention relates to compounds where at least one of $R_f$ and $R_g$ is t-butyl substituted with hydroxyl.

The invention relates to a compound selected from Tables 1-4. The invention also relates to a salt of a compound selected from Tables 1-4. The invention also relates to an N-oxide of compound selected from Tables 1-4. The invention also relates to a salt of an N-oxide of compound selected from Tables 1-4. For example, the invention relates to a compound selected from Compounds A1-A7, A9-A109, and A111-A140.

Other compounds suitable for the methods of the invention, as well as pharmaceutical compositions and uses thereof, are described in WO2012/075381, WO2012/075492, WO2012/082436, and WO2012/75500, the contents of which are hereby incorporated by reference in their entireties.

The invention also relates to a pharmaceutical composition of a therapeutically effective amount of a compound of any of the Formulae disclosed herein and a pharmaceutically acceptable carrier.

The invention also relates to a pharmaceutical composition of a therapeutically effective amount of a salt of a compound of any of the Formulae disclosed herein and a pharmaceutically acceptable carrier.

The invention also relates to a pharmaceutical composition of a therapeutically effective amount of a hydrate of a compound of any of the Formulae disclosed herein and a pharmaceutically acceptable carrier.

The invention also relates to a pharmaceutical composition of a therapeutically effective amount of a compound selected from Tables 1-4 and a pharmaceutically acceptable carrier. The invention also relates to a pharmaceutical composition of a therapeutically effective amount of a salt of a compound selected from Tables 1-4 and a pharmaceutically acceptable carrier. The invention also relates to a pharmaceutical composition of a therapeutically effective amount of an N-oxide of a compound selected from Tables 1-4 and a pharmaceutically acceptable carrier. The invention also relates to a pharmaceutical composition of a therapeutically effective amount of an N-oxide of salt of a compound selected from Tables 1-4 and a pharmaceutically acceptable carrier. The invention also relates to a pharmaceutical composition of a therapeutically effective amount of a hydrate of a compound selected from Tables 1-4 and a pharmaceutically acceptable carrier.

The present invention provides methods of treating or preventing cancer. The present invention provides methods of treating cancer. The present invention also provides methods of preventing cancer. The method includes administering to a subject in need thereof a therapeutically effective amount of the compound of any of the Formulae disclosed herein. The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11q23. The present invention provides methods of treating a disease or disorder mediated by translocation of a gene on chromosome 11q23. The present invention also provides methods of preventing a disease or disorder mediated by translocation of a gene on chromosome 11q23. The method includes administering to a subject in need thereof a therapeutically effective amount of the compound of any of the Formulae disclosed herein.

The present invention provides methods of treating or preventing a disease or disorder in which DOT1-mediated protein methylation plays a part or a disease or disorder mediated by DOT1-mediated protein methylation. The present invention provides methods of treating a disease or disorder in which DOT1-mediated protein methylation plays a part or a disease or disorder mediated by DOT1-mediated protein methylation. The present invention also provides methods of preventing a disease or disorder in which DOT1-mediated protein methylation plays a part or a disease or disorder mediated by DOT1-mediated protein methylation. The method includes administering to a subject in need thereof a therapeutically effective amount of the compound of any of the Formulae disclosed herein.

The present invention provides methods of inhibiting DOT1L activity in a cell. The method includes contacting the cell with an effective amount of one or more of the compound of any of the Formulae disclosed herein.

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

The present invention relates to use of the compounds disclosed herein in preparation of a medicament for treating or preventing cancer. The use includes a compound of any of the Formulae disclosed herein for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound of any of the Formulae disclosed herein for administration to a subject in need thereof in a therapeutically effective amount.

The present invention provides use of the compounds disclosed herein in preparation of a medicament for treating or preventing a disease or disorder in which DOT1-mediated protein methylation plays a part or a disease or disorder mediated by DOT1-mediated protein methylation. The use includes a compound of any of the Formulae disclosed herein for administration to a subject in need thereof in a therapeutically effective amount.

The present invention provides use of the compounds disclosed herein for inhibiting DOT1L activity in a cell. The use includes contacting the cell with an effective amount of one or more of the compound of any of the Formulae disclosed herein.

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1 through H3-K79 methylation.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Representative compounds of the present invention include compounds listed in Tables 1-4.

TABLE 1

| Cmpd No. | Chemical Name |
|---|---|
| A1 | (2R,3S,4R,5R)-2-(((3-(2-(1H-benzo[d]imidazol-2-yl)ethyl)cyclobutyl)amino)methyl)-5-(6-amino-9H-purin-9-yl)tetrahydrofuran-3,4-diol |
| A2 | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol |
| A3 | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(isopropyl)amino)methyl)tetrahydrofuran-3,4-diol |
| A4 | (2R,3R,4S,5R)-2-(6-amino-9H-purin-9-yl)-5-((((1s,3R)-3-(2-(5-chloro-6-(trifluoromethyl)-1H-benzo[d]imidazol-2-yl)ethyl)cyclobutyl)(isopropyl)amino)methyl)tetrahydrofuran-3,4-diol |
| A5 | (2R,3R,4S,5R)-2-(6-amino-9H-purin-9-yl)-5-((((1r,3S)-3-(2-(5-chloro-6-(trifluoromethyl)-1H-benzo[d]imidazol-2-yl)ethyl)cyclobutyl)(isopropyl)amino)methyl)tetrahydrofuran-3,4-diol |
| A6 | (2R,3R,4S,5R)-2-(4-amino-7H-pyrrolo[2,3-d]pyrimidin-7-yl)-5-(((3-((5-(tert-butyl)-1H-benzo[d]imidazol-2-yl)methyl)cyclobutyl)(methyl)amino)methyl)tetrahydrofuran-3,4-diol |
| A7 | (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(methyl)amino)methyl)cyclopentane-1,2-diol |
| A8 | 1-(3-(((((2R,3S,4R,5R)-5-(6-amino-9H-purin-9-yl)-3,4-dihydroxytetrahydrofuran-2-yl)methyl)(methyl)amino)cyclobutyl)-3-(4-tert-butylphenyl)urea |
| A9 | (1R,2S,3R,5R)-3-(4-amino-7H-pyrrolo[2,3-d]pyrimidin-7-yl)-5-((((1r,3S)-3-(2-(6-chloro-5-(trifluoromethyl)-1H-benzo[d]imidazol-2-yl)ethyl)cyclobutyl)(methyl)amino)methyl)cyclopentane-1,2-diol |

TABLE 1-continued

| Cmpd No. | Chemical Name |
|---|---|
| A10 | (1R,2S,3R,5R)-3-(4-amino-7H-pyrrolo[2,3-d]pyrimidin-7-yl)-5-((methyl((1r,3S)-3-(2-(5-(trifluoromethyl)-1H-benzo[d]imidazol-2-yl)ethyl)cyclobutyl)amino)methyl)cyclopentane-1,2-diol |
| A11 | (1R,2S,3R,5R)-3-(4-amino-7H-pyrrolo[2,3-d]pyrimidin-7-yl)-5-((methyl((1s,3R)-3-(2-(5-(trifluoromethyl)-1H-benzo[d]imidazol-2-yl)ethyl)cyclobutyl)amino)methyl)cyclopentane-1,2-diol |
| A12 | (1R,2S,3R,5R)-3-(4-amino-7H-pyrrolo[2,3-d]pyrimidin-7-yl)-5-(((((1s,3R)-3-(2-(6-chloro-5-(trifluoromethyl)-1H-benzo[d]imidazol-2-yl)ethyl)cyclobutyl)(methyl)amino)methyl)cyclopentane-1,2-diol |
| A13 | (1R,2S,3R,5R)-3-(4-amino-7H-pyrrolo[2,3-d]pyrimidin-7-yl)-5-((methyl(3-(2-(5-(trifluoromethyl)-1H-benzo[d]imidazol-2-yl)ethyl)cyclobutyl)amino)methyl)cyclopentane-1,2-diol |
| A14 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(methyl)amino)methyl)cyclopentane-1,2-diol |
| A15 | (1R,2S,3R,5R)-3-(4-amino-7H-pyrrolo[2,3-d]pyrimidin-7-yl)-5-((isopropyl((3-((5-(trifluoromethyl)-1H-benzo[d]imidazol-2-yl)methyl)cyclobutyl)methyl)amino)methyl)cyclopentane-1,2-diol |
| A16 | (1R,2S,3R,5R)-3-(4-amino-7H-pyrrolo[2,3-d]pyrimidin-7-yl)-5-(((3-(5-chloro-6-(trifluoromethyl)-1H-benzo[d]imidazol-2-yl)cyclobutyl)(methyl)amino)methyl)cyclopentane-1,2-diol |
| A17 | (1R,2R,4S)-2-(4-amino-7H-pyrrolo[2,3-d]pyrimidin-7-yl)-4-(((3-(2-(5-chloro-6-(trifluoromethyl)-1H-benzo[d]imidazol-2-yl)ethyl)cyclobutyl)(methyl)amino)methyl)cyclopentanol |
| A18 | (1R,2S,3R,5R)-3-(4-amino-7H-pyrrolo[2,3-d]pyrimidin-7-yl)-5-((methyl(3-((5-(trifluoromethyl)-1H-benzo[d]imidazol-2-yl)methyl)cyclobutyl)methyl)amino)methyl)cyclopentane-1,2-diol |
| A19 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isopropyl)amino)methyl)cyclopentane-1,2-diol |
| A20 | (1R,2S,3R,5R)-3-(4-amino-7H-pyrrolo[2,3-d]pyrimidin-7-yl)-5-(((3-(2-(6-chloro-5-(trifluoromethyl)-1H-benzo[d]imidazol-2-yl)ethyl)cyclobutyl)(isopropyl)amino)methyl)cyclopentane-1,2-diol |
| A21 | (1R,2S,3R,5R)-3-(4-amino-7H-pyrrolo[2,3-d]pyrimidin-7-yl)-5-((((3-((6-chloro-5-(trifluoromethyl)-1H-benzo[d]imidazol-2-yl)methyl)cyclobutyl)methyl)(isopropyl)amino)methyl)cyclopentane-1,2-diol |
| A22 | (1R,2S,3R,5R)-3-(4-amino-7H-pyrrolo[2,3-d]pyrimidin-7-yl)-5-((((3-((5-(tert-butyl)-1H-benzo[d]imidazol-2-yl)methyl)cyclobutyl)methyl)(isopropyl)amino)methyl)cyclopentane-1,2-diol |
| A23 | (1R,2S,3R,5R)-3-(4-amino-7H-pyrrolo[2,3-d]pyrimidin-7-yl)-5-(((3-(2-(5,6-dichloro-1H-benzo[d]imidazol-2-yl)ethyl)cyclobutyl)(methyl)amino)methyl)cyclopentane-1,2-diol |
| A24 | (1R,2S,3R,5R)-3-(4-amino-7H-pyrrolo[2,3-d]pyrimidin-7-yl)-5-((methyl(3-(2-(5-(trifluoromethoxy)-1H-benzo[d]imidazol-2-yl)ethyl)cyclobutyl)amino)methyl)cyclopentane-1,2-diol |
| A25 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(ethyl)amino)methyl)cyclopentane-1,2-diol |
| A26 | (1R,2S,3R,5R)-3-(4-amino-7H-pyrrolo[2,3-d]pyrimidin-7-yl)-5-(((3-(2-(5-bromo-1H-benzo[d]imidazol-2-yl)ethyl)cyclobutyl)(methyl)amino)methyl)cyclopentane-1,2-diol |
| A27 | (2R,3R,4S,5R)-2-(6-amino-9H-purin-9-yl)-5-((isopropyl(3-(2-(5-(1-methylcyclobutyl)-1H-benzo[d]imidazol-2-yl)ethyl)cyclobutyl)amino)methyl)tetrahydrofuran-3,4-diol |
| A28 | (2R,3R,4S,5R)-2-(6-amino-9H-purin-9-yl)-5-((isopropyl((1r,3S)-3-(2-(5-(1-methylcyclobutyl)-1H-benzo[d]imidazol-2-yl)ethyl)cyclobutyl)amino)methyl)tetrahydrofuran-3,4-diol |
| A29 | (1R,2S,3R,5R)-3-(4-amino-7H-pyrrolo[2,3-d]pyrimidin-7-yl)-5-((methyl(3-(2-(5-(1-methylcyclobutyl)-1H-benzo[d]imidazol-2-yl)ethyl)cyclobutyl)amino)methyl)cyclopentane-1,2-diol |
| A30 | (2R,3R,4S,5R)-2-(6-amino-9H-purin-9-yl)-5-((methyl((1r,3S)-3-(2-(5-(1-methylcyclobutyl)-1H-benzo[d]imidazol-2-yl)ethyl)cyclobutyl)amino)methyl)tetrahydrofuran-3,4-diol |
| A31 | (2R,3R,4S,5R)-2-(6-amino-9H-purin-9-yl)-5-((isopropyl((1s,3R)-3-(2-(5-(1-methylcyclobutyl)-1H-benzo[d]imidazol-2-yl)ethyl)cyclobutyl)amino)methyl)tetrahydrofuran-3,4-diol |
| A32 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(methyl)amino)methyl)cyclopentane-1,2-diol |
| A33 | (2R,3R,4S,5R)-2-(6-amino-9H-purin-9-yl)-5-((methyl(3-(2-(5-(1-methylcyclobutyl)-1H-benzo[d]imidazol-2-yl)ethyl)cyclobutyl)amino)methyl)tetrahydrofuran-3,4-diol |
| A34 | (2R,3R,4S,5R)-2-(6-amino-9H-purin-9-yl)-5-((methyl((1s,3R)-3-(2-(5-(1-methylcyclobutyl)-1H-benzo[d]imidazol-2-yl)ethyl)cyclobutyl)amino)methyl)tetrahydrofuran-3,4-diol |
| A35 | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(methyl)amino)methyl)cyclopentane-1,2-diol |
| A36 | (1R,2S,3R,5R)-3-(4-amino-7H-pyrrolo[2,3-d]pyrimidin-7-yl)-5-((methyl((1r,3S)-3-(2-(5-(1-methylcyclobutyl)-1H-benzo[d]imidazol-2-yl)ethyl)cyclobutyl)amino)methyl)cyclopentane-1,2-diol |
| A37 | (1R,2S,3R,5R)-3-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)cyclopentane-1,2-diol |
| A38 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(ethyl)amino)methyl)cyclopentane-1,2-diol |
| A39 | (1R,2S,3R,5R)-3-(4-amino-7H-pyrrolo[2,3-d]pyrimidin-7-yl)-5-((methyl((1s,3R)-3-(2-(5-(1-methylcyclobutyl)-1H-benzo[d]imidazol-2-yl)ethyl)cyclobutyl)amino)methyl)cyclopentane-1,2-diol |
| A40 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(cyclopropylmethyl)amino)methyl)cyclopentane-1,2-diol |
| A41 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(isopropyl)amino)methyl)cyclopentane-1,2-diol |
| A42 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(cyclobutylmethyl)amino)methyl)cyclopentane-1,2-diol |
| A43 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclobutyl)amino)methyl)cyclopentane-1,2-diol |
| A44 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(cyclopropylmethyl)amino)methyl)cyclopentane-1,2-diol |
| A45 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(isobutyl)amino)methyl)cyclopentane-1,2-diol |
| A46 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(cyclobutyl)amino)methyl)cyclopentane-1,2-diol |
| A47 | (1R,2S,3R,5R)-3-(4-amino-7H-pyrrolo[2,3-d]pyrimidin-7-yl)-5-(((((1r,3S)-3-(2-(5-bromo-1H-benzo[d]imidazol-2-yl)ethyl)cyclobutyl)(methyl)amino)methyl)cyclopentane-1,2-diol |
| A48 | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(isobutyl)amino)methyl)cyclopentane-1,2-diol |

TABLE 1-continued

| Cmpd No. | Chemical Name |
|---|---|
| A49 | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(ethyl)amino)methyl)cyclopentane-1,2-diol |
| A50 | (1R,2S,3R,5R)-3-(6-amino-9H-purin-9-yl)-5-(((3-(2-(5-(tert-butyl)-1H-benzo[d]imidazol-2-yl)ethyl)cyclobutyl)(isopropyl)amino)methyl)cyclopentane-1,2-diol |
| A51 | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(cyclobutyl)amino)methyl)cyclopentane-1,2-diol |
| A52 | (1R,2S,3R,5R)-3-(4-amino-7H-pyrrolo[2,3-d]pyrimidin-7-yl)-5-(((((1r,3S)-3-(2-(5,6-dichloro-1H-benzo[d]imidazol-2-yl)ethyl)cyclobutyl)(methyl)amino)methyl)cyclopentane-1,2-diol |
| A53 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(isobutyl)amino)methyl)cyclopentane-1,2-diol |
| A54 | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(cyclopropylmethyl)amino)methyl)cyclopentane-1,2-diol |
| A55 | (1R,2S,3R,5R)-3-(4-amino-7H-pyrrolo[2,3-d]pyrimidin-7-yl)-5-(((((1s,3R)-3-(2-(5-bromo-1H-benzo[d]imidazol-2-yl)ethyl)cyclobutyl)(methyl)amino)methyl)cyclopentane-1,2-diol |
| A56 | (1R,2S,3R,5R)-3-(4-amino-7H-pyrrolo[2,3-d]pyrimidin-7-yl)-5-((isopropyl(3-(2-(5-(trifluoromethoxy)-1H-benzo[d]imidazol-2-yl)ethyl)cyclobutyl)amino)methyl)cyclopentane-1,2-diol |
| A57 | (1R,2S,3R,5R)-3-(4-amino-7H-pyrrolo[2,3-d]pyrimidin-7-yl)-5-((methyl((1s,3R)-3-(2-(5-(trifluoromethoxy)-1H-benzo[d]imidazol-2-yl)ethyl)cyclobutyl)amino)methyl)cyclopentane-1,2-diol |
| A58 | (1R,2S,3R,5R)-3-(4-amino-7H-pyrrolo[2,3-d]pyrimidin-7-yl)-5-(((((1s,3R)-3-(2-(5,6-dichloro-1H-benzo[d]imidazol-2-yl)ethyl)cyclobutyl)(methyl)amino)methyl)cyclopentane-1,2-diol |
| A59 | (1R,2S,3R,5R)-3-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(cyclobutylmethyl)amino)methyl)cyclopentane-1,2-diol |
| A60 | (1R,2S,3R,5R)-3-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)cyclopentane-1,2-diol |
| A61 | (1R,2S,3R,5R)-3-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)cyclopentane-1,2-diol |
| A62 | (1R,2S,3R,5R)-3-(4-amino-7H-pyrrolo[2,3-d]pyrimidin-7-yl)-5-((methyl(3-(2-(5-(oxetan-3-yl)-1H-benzo[d]imidazol-2-yl)ethyl)cyclobutyl)amino)methyl)cyclopentane-1,2-diol |
| A63 | (2R,3R,4S,5R)-2-(6-amino-9H-purin-9-yl)-5-((methyl((1r,3S)-3-(2-(5-(oxetan-3-yl)-1H-benzo[d]imidazol-2-yl)ethyl)cyclobutyl)amino)methyl)tetrahydrofuran-3,4-diol |
| A64 | (2R,3R,4S,5R)-2-(6-amino-9H-purin-9-yl)-5-((methyl(3-(2-(5-(oxetan-3-yl)-1H-benzo[d]imidazol-2-yl)ethyl)cyclobutyl)amino)methyl)tetrahydrofuran-3,4-diol |
| A65 | (2R,3R,4S,5R)-2-(6-amino-9H-purin-9-yl)-5-((methyl((1s,3R)-3-(2-(5-(oxetan-3-yl)-1H-benzo[d]imidazol-2-yl)ethyl)cyclobutyl)amino)methyl)tetrahydrofuran-3,4-diol |
| A66 | (1R,2S,3R,5R)-3-(4-amino-7H-pyrrolo[2,3-d]pyrimidin-7-yl)-5-(((3-(2-(5-(tert-butyl)-1H-benzo[d]imidazol-2-yl)ethyl)cyclobutyl)(2,2,2-trifluoroethyl)amino)methyl)cyclopentane-1,2-diol |
| A67 | (2R,3R,4S,5R)-2-(6-amino-9H-purin-9-yl)-5-(((3-(2-(5-cyclobutyl-1H-benzo[d]imidazol-2-yl)ethyl)cyclobutyl)(isopropyl)amino)methyl)tetrahydrofuran-3,4-diol |
| A68 | (2R,3R,4S,5R)-2-(6-amino-9H-purin-9-yl)-5-(((3-(2-(5-(1-methoxy-2-methylpropan-2-yl)-1H-benzo[d]imidazol-2-yl)ethyl)cyclobutyl)(methyl)amino)methyl)tetrahydrofuran-3,4-diol |
| A69 | (1R,2S,3R,5R)-3-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(methyl)amino)methyl)cyclopentane-1,2-diol |
| A70 | (1R,2S,3R,5R)-3-(4-amino-7H-pyrrolo[2,3-d]pyrimidin-7-yl)-5-(((((1s,3R)-3-(2-(6-(tert-butyl)-1H-benzo[d]imidazol-2-yl)ethyl)cyclobutyl)(methyl)amino)methyl)cyclopentane-1,2-diol |
| A71 | (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(methyl)amino)methyl)tetrahydrofuran-3,4-diol |
| A72 | (2R,3R,4S,5R)-2-(6-amino-9H-purin-9-yl)-5-(((((1s,3R)-3-(2-(5-(tert-butyl)-1H-benzo[d]imidazol-2-yl)ethyl)cyclobutyl)(methyl)amino)methyl)tetrahydrofuran-3,4-diol |
| A73 | (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(ethyl)amino)methyl)tetrahydrofuran-3,4-diol |
| A74 | (2R,3R,4S,5R)-2-(6-amino-9H-purin-9-yl)-5-(((((1s,3R)-3-(2-(5-(tert-butyl)-1H-benzo[d]imidazol-2-yl)ethyl)cyclobutyl)(ethyl)amino)methyl)tetrahydrofuran-3,4-diol |
| A75 | (2R,3R,4S,5R)-2-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(isopropyl)amino)methyl)tetrahydrofuran-3,4-diol |
| A76 | (2R,3R,4S,5R)-2-(4-amino-7H-pyrrolo[2,3-d]pyrimidin-7-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol |
| A77 | (2R,3R,4S,5R)-2-(4-amino-7H-pyrrolo[2,3-d]pyrimidin-7-yl)-5-(((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol |
| A78 | (2R,3R,4S,5R)-2-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol |
| A79 | (2R,3R,4S,5R)-2-(6-amino-9H-purin-9-yl)-5-(((3-(2-(5-(tert-butyl)-1H-benzo[d]imidazol-2-yl)ethyl)cyclobutyl)(ethyl)amino)methyl)tetrahydrofuran-3,4-diol |
| A80 | (2R,3R,4S,5R)-2-(6-amino-9H-purin-9-yl)-5-(((((1s,3R)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol |
| A81 | (1R,2R,4S)-2-(4-amino-7H-pyrrolo[2,3-d]pyrimidin-7-yl)-4-(((((1r,3R)-3-(2-(5-chloro-6-(trifluoromethyl)-1H-benzo[d]imidazol-2-yl)ethyl)cyclobutyl)(methyl)amino)methyl)cyclopentanol |
| A82 | (2R,3R,4S,5R)-2-(6-amino-9H-purin-9-yl)-5-(((3-(2-(5-(tert-butyl)-1H-benzo[d]imidazol-2-yl)ethyl)cyclobutyl)(2,2,2-trifluoroethyl)amino)methyl)tetrahydrofuran-3,4-diol |
| A83 | (1R,2R,4S)-2-(4-amino-7H-pyrrolo[2,3-d]pyrimidin-7-yl)-4-(((3-(2-(5-(tert-butyl)-1H-benzo[d]imidazol-2-yl)ethyl)cyclobutyl)(isopropyl)amino)methyl)cyclopentanol |
| A84 | (1R,2R,4S)-2-(4-amino-7H-pyrrolo[2,3-d]pyrimidin-7-yl)-4-(((3-(2-(5-chloro-6-(trifluoromethyl)-1H-benzo[d]imidazol-2-yl)ethyl)cyclobutyl)(isopropyl)amino)methyl)cyclopentanol |
| A85 | (1R,2R,4S)-2-(4-amino-7H-pyrrolo[2,3-d]pyrimidin-7-yl)-4-(((((1s,3S)-3-(2-(5-chloro-6-(trifluoromethyl)-1H-benzo[d]imidazol-2-yl)ethyl)cyclobutyl)(methyl)amino)methyl)cyclopentanol |
| A86 | (2R,3R,4S,5R)-2-(4-amino-7H-pyrrolo[2,3-d]pyrimidin-7-yl)-5-(((((1r,3S)-3-(2-(5-(tert-butyl)-1H-benzo[d]imidazol-2-yl)ethyl)cyclobutyl)(methyl)amino)methyl)tetrahydrofuran-3,4-diol |
| A87 | (2R,3R,4S,5R)-2-(4-amino-7H-pyrrolo[2,3-d]pyrimidin-7-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol |

TABLE 1-continued

| Cmpd No. | Chemical Name |
|---|---|
| A88 | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(ethyl)amino)methyl)tetrahydrofuran-3,4-diol |
| A89 | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(ethyl)amino)methyl)tetrahydrofuran-3,4-diol |
| A90 | (2R,3R,4S,5R)-2-(4-amino-7H-pyrrolo[2,3-d]pyrimidin-7-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol |
| A91 | (2R,3R,4S,5R)-2-(6-amino-9H-purin-9-yl)-5-((isopropyl((1r,3S)-3-(2-(5-(trifluoromethoxy)-1H-benzo[d]imidazol-2-yl)ethyl)cyclobutyl)amino)methyl)tetrahydrofuran-3,4-diol |
| A92 | (2R,3R,4S,5R)-2-(4-amino-7H-pyrrolo[2,3-d]pyrimidin-7-yl)-5-((((1s,3R)-3-(2-(5-(tert-butyl)-1H-benzo[d]imidazol-2-yl)ethyl)cyclobutyl)(methyl)amino)methyl)tetrahydrofuran-3,4-diol |
| A93 | (2R,3R,4S,5R)-2-(6-amino-9H-purin-9-yl)-5-((isopropyl((1s,3R)-3-(2-(5-(trifluoromethoxy)-1H-benzo[d]imidazol-2-yl)ethyl)cyclobutyl)amino)methyl)tetrahydrofuran-3,4-diol |
| A94 | (2R,3R,4S,5R)-2-(4-amino-7H-pyrrolo[2,3-d]pyrimidin-7-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol |
| A95 | (2R,3R,4S,5R)-2-(4-amino-7H-pyrrolo[2,3-d]pyrimidin-7-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol |
| A96 | (2R,3R,4S,5R)-2-(6-amino-9H-purin-9-yl)-5-((methyl((1r,3S)-3-(2-(5-(trifluoromethoxy)-1H-benzo[d]imidazol-2-yl)ethyl)cyclobutyl)amino)methyl)tetrahydrofuran-3,4-diol |
| A97 | (2R,3R,4S,5R)-2-(6-amino-9H-purin-9-yl)-5-((methyl((1s,3R)-3-(2-(5-(trifluoromethoxy)-1H-benzo[d]imidazol-2-yl)ethyl)cyclobutyl)amino)methyl)tetrahydrofuran-3,4-diol |
| A98 | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)amino)methyl)tetrahydrofuran-3,4-diol |
| A99 | (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)amino)methyl)tetrahydrofuran-3,4-diol |
| 1A00 | (2R,3R,4S,5R)-2-(6-amino-9H-purin-9-yl)-5-((isopropyl(3-(2-(5-(trifluoromethoxy)-1H-benzo[d]imidazol-2-yl)ethyl)cyclobutyl)amino)methyl)tetrahydrofuran-3,4-diol |
| A101 | (1R,2R,4S)-2-(4-amino-7H-pyrrolo[2,3-d]pyrimidin-7-yl)-4-((((1r,3R)-3-(2-(5-(tert-butyl)-1H-benzo[d]imidazol-2-yl)ethyl)cyclobutyl)(isopropyl)amino)methyl)cyclopentanol |
| A102 | (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(2,2,2-trifluoroethyl)amino)methyl)tetrahydrofuran-3,4-diol |
| A103 | (1R,2R,4S)-2-(4-amino-7H-pyrrolo[2,3-d]pyrimidin-7-yl)-4-((((1s,3S)-3-(2-(5-chloro-6-(trifluoromethyl)-1H-benzo[d]imidazol-2-yl)ethyl)cyclobutyl)(isopropyl)amino)methyl)cyclopentanol |
| A104 | (1R,2R,4S)-2-(4-amino-7H-pyrrolo[2,3-d]pyrimidin-7-yl)-4-((((1s,3S)-3-(2-(5-(tert-butyl)-1H-benzo[d]imidazol-2-yl)ethyl)cyclobutyl)(isopropyl)amino)methyl)cyclopentanol |
| A105 | (1R,2R,4S)-2-(4-amino-7H-pyrrolo[2,3-d]pyrimidin-7-yl)-4-((((1r,3R)-3-(2-(5-chloro-6-(trifluoromethyl)-1H-benzo[d]imidazol-2-yl)ethyl)cyclobutyl)(isopropyl)amino)methyl)cyclopentanol |
| A106 | (1r,3S)-N-(((2R,3S,4R,5R)-5-(6-amino-9H-purin-9-yl)-3,4-dihydroxytetrahydrofuran-2-yl)methyl)-3-(2-(5-(tert-butyl)-1H-benzo[d]imidazol-2-yl)ethyl)-N-isopropylcyclobutanamine oxide |
| A107 | (R,1s,3R)-N-(((2R,3S,4R,5R)-5-(6-amino-9H-purin-9-yl)-3,4-dihydroxytetrahydrofuran-2-yl)methyl)-3-(2-(5-(tert-butyl)-1H-benzo[d]imidazol-2-yl)ethyl)-N-isopropylcyclobutanamine oxide |
| A108 | (2R,3R,4S,5R)-2-(6-amino-9H-purin-9-yl)-5-((((1r,3S)-3-(2-(5-(1-hydroxy-2-methylpropan-2-yl)-1H-benzo[d]imidazol-2-yl)ethyl)cyclobutyl)(isopropyl)amino)methyl)tetrahydrofuran-3,4-diol |
| A109 | (2R,3R,4S,5R)-2-(6-amino-9H-purin-9-yl)-5-((((1s,3R)-3-(2-(5-(1-hydroxy-2-methylpropan-2-yl)-1H-benzo[d]imidazol-2-yl)ethyl)cyclobutyl)(isopropyl)amino)methyl)tetrahydrofuran-3,4-diol |
| A110 | 1-((3-((((2R,3S,4R,5R)-5-(6-amino-9H-purin-9-yl)-3,4-dihydroxytetrahydrofuran-2-yl)methyl)(methyl)amino)cyclobutyl)methyl)-3-(4-(tert-butyl)phenyl)urea |
| A111 | (2R,3R,4S,5R)-2-(6-amino-9H-purin-9-yl)-5-(((3-(2-(5-cyclobutyl-1H-benzo[d]imidazol-2-yl)ethyl)cyclobutyl)(isopropyl)amino)methyl)tetrahydrofuran-3,4-diol |
| A112 | (2R,3R,4S,5R)-2-(6-amino-9H-purin-9-yl)-5-(((3-(2-(5-cyclopropyl-1H-benzo[d]imidazol-2-yl)ethyl)cyclobutyl)(isopropyl)amino)methyl)tetrahydrofuran-3,4-diol |
| A113 | (2R,3R,4S,5R)-2-(6-amino-9H-purin-9-yl)-5-((isopropyl(3-(2-(5-(2,2,2-trifluoroethyl)-1H-benzo[d]imidazol-2-yl)ethyl)cyclobutyl)amino)methyl)tetrahydrofuran-3,4-diol |
| A114 | (2R,3R,4S,5R)-2-(6-amino-9H-purin-9-yl)-5-((((1s,3R)-3-(2-(5-cyclobutyl-1H-benzo[d]imidazol-2-yl)ethyl)cyclobutyl)(isopropyl)amino)methyl)tetrahydrofuran-3,4-diol |
| A115 | (2R,3R,4S,5R)-2-(6-amino-9H-purin-9-yl)-5-((((1r,3S)-3-(2-(5-cyclobutyl-1H-benzo[d]imidazol-2-yl)ethyl)cyclobutyl)(isopropyl)amino)methyl)tetrahydrofuran-3,4-diol |
| A116 | (2R,3R,4S,5R)-2-(6-amino-9H-purin-9-yl)-5-((((1r,3S)-3-(2-(5-cyclopropyl-1H-benzo[d]imidazol-2-yl)ethyl)cyclobutyl)(isopropyl)amino)methyl)tetrahydrofuran-3,4-diol |
| A117 | 1-(2-(2-(3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclobutanecarbonitrile |
| A118 | (2R,3R,4S,5R)-2-(6-amino-9H-purin-9-yl)-5-((isopropyl(3-(2-(5-(1-methoxy-2-methylpropan-2-yl)-1H-benzo[d]imidazol-2-yl)ethyl)cyclobutyl)amino)methyl)tetrahydrofuran-3,4-diol |
| A119 | (2R,3R,4S,5R)-2-(6-amino-9H-purin-9-yl)-5-((((1s,3R)-3-(2-(5-cyclopropyl-1H-benzo[d]imidazol-2-yl)ethyl)cyclobutyl)(isopropyl)amino)methyl)tetrahydrofuran-3,4-diol |
| A120 | 2-(2-(2-(3-(((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile |
| A121 | (2R,3R,4S,5R)-2-(6-amino-9H-purin-9-yl)-5-((isopropyl((1s,3R)-3-(2-(5-(1-methoxy-2-methylpropan-2-yl)-1H-benzo[d]imidazol-2-yl)ethyl)cyclobutyl)amino)methyl)tetrahydrofuran-3,4-diol |
| A122 | (2R,3R,4S,5R)-2-(6-amino-9H-purin-9-yl)-5-((isopropyl((1r,3S)-3-(2-(5-(1-methoxy-2-methylpropan-2-yl)-1H-benzo[d]imidazol-2-yl)ethyl)cyclobutyl)amino)methyl)tetrahydrofuran-3,4-diol |
| A123 | (2R,3R,4S,5R)-2-(6-amino-9H-purin-9-yl)-5-((isopropyl((1s,3R)-3-(2-(5-(2,2,2-trifluoroethyl)-1H-benzo[d]imidazol-2-yl)ethyl)cyclobutyl)amino)methyl)tetrahydrofuran-3,4-diol |
| A124 | (2R,3R,4S,5R)-2-(6-amino-9H-purin-9-yl)-5-((isopropyl((1r,3S)-3-(2-(5-(2,2,2-trifluoroethyl)-1H-benzo[d]imidazol-2-yl)ethyl)cyclobutyl)amino)methyl)tetrahydrofuran-3,4-diol |
| A125 | (2R,3R,4S,5R)-2-(6-amino-9H-purin-9-yl)-5-(((3-(2-(5-cyclobutyl-1H-benzo[d]imidazol-2-yl)ethyl)cyclobutyl)(methyl)amino)methyl)tetrahydrofuran-3,4-diol |
| A126 | 1-(2-(2-(3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile |

TABLE 1-continued

| Cmpd No. | Chemical Name |
| --- | --- |
| A127 | (2R,3R,4S,5R)-2-(6-amino-9H-purin-9-yl)-5-(((3-(2-(5-cyclopropyl-1H-benzo[d]imidazol-2-yl)ethyl)cyclobutyl)(methyl)amino)methyl)tetrahydrofuran-3,4-diol |
| A128 | 2-(2-(2-((1S,3r)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile |
| A129 | 2-(2-(2-((1R,3s)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)-2-methylpropanenitrile |
| A130 | 1-(2-(2-(3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile |
| A131 | (2R,3R,4S,5R)-2-(6-amino-9H-purin-9-yl)-5-((((1r,3S)-3-(2-(5-cyclobutyl-1H-benzo[d]imidazol-2-yl)ethyl)cyclobutyl)(methyl)amino)methyl)tetrahydrofuran-3,4-diol |
| A132 | (2R,3R,4S,5R)-2-(6-amino-9H-purin-9-yl)-5-((((1s,3R)-3-(2-(5-cyclobutyl-1H-benzo[d]imidazol-2-yl)ethyl)cyclobutyl)(methyl)amino)methyl)tetrahydrofuran-3,4-diol |
| A133 | (2R,3R,4S,5R)-2-(6-amino-9H-purin-9-yl)-5-((((1r,3S)-3-(2-(5-cyclopropyl-1H-benzo[d]imidazol-2-yl)ethyl)cyclobutyl)(methyl)amino)methyl)tetrahydrofuran-3,4-diol |
| A134 | (2R,3R,4S,5R)-2-(6-amino-9H-purin-9-yl)-5-((((1s,3R)-3-(2-(5-cyclopropyl-1H-benzo[d]imidazol-2-yl)ethyl)cyclobutyl)(methyl)amino)methyl)tetrahydrofuran-3,4-diol |
| A135 | 1-(2-(2-((1S,3r)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile |
| A136 | 1-(2-(2-((1R,3s)-3-((((2R,3S,4R,5R)-5-(6-amino-9H-purin-9-yl)-3,4-dihydroxytetrahydrofuran-2-yl)methyl)(isopropyl)amino)cyclobutyl)ethyl)-1H-benzo[d]imidazol-5-yl)cyclopropanecarbonitrile |
| A137 | 1-(2-(2-((1S,3r)-3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile |
| A138 | 1-(2-(2-((1R,3s)-3-((((2R,3S,4R,5R)-5-(6-amino-9H-purin-9-yl)-3,4-dihydroxytetrahydrofuran-2-yl)methyl)(methyl)amino)cyclobutyl)ethyl)-1H-benzo[d]imidazol-5-yl)cyclopropanecarbonitrile |
| A139 | (2R,3R,4S,5R)-2-(6-amino-9H-purin-9-yl)-5-((isopropyl(3-(2-(5-(1-methylcyclopropyl)-1H-benzo[d]imidazol-2-yl)ethyl)cyclobutyl)amino)methyl)tetrahydrofuran-3,4-diol |
| A140 | (2R,3R,4S,5R)-2-(6-amino-9H-purin-9-yl)-5-(((3-(2-(5-(1-methoxy-2-methylpropan-2-yl)-1H-benzo[d]imidazol-2-yl)ethyl)cyclobutyl)(methyl)amino)methyl)tetrahydrofuran-3,4-diol |

TABLE 2

| Cmpd. No. | Chemical Name |
| --- | --- |
| B1 | (1R,2S,3R,5R)-3-(4-amino-7H-pyrrolo[2,3-d]pyrimidin-7-yl)-5-(((4-(5-tert-butyl-1H-benzo[d]imidazol-2-yl)butyl)(isopropyl)amino)methyl)cyclopentane-1,2-diol |
| B2 | (1R,2S,3R,5S)-3-(4-amino-7H-pyrrolo[2,3-d]pyrimidin-7-yl)-5-(((4-(5-tert-butyl-1H-benzo[d]imidazol-2-yl)butyl)(isopropyl)amino)methyl)cyclopentane-1,2-diol |
| B3 | 1-(3-(((((1S,2R,3S,4R)-4-(6-amino-9H-purin-9-yl)-2,3-dihydroxycyclopentyl)methyl)(methyl)amino)propyl)-3-(4-(tert-butyl)phenyl)urea |
| B4 | (1S,2R,3R,5R)-3-(((4-(6-chloro-5-(trifluoromethyl)-1H-benzo[d]imidazol-2-yl)butyl)(isopropyl)amino)methyl)-5-(4-(cyclopropylamino)-7H-pyrrolo[2,3-d]pyrimidin-7-yl)cyclopentane-1,2-diol |
| B5 | (1S,2R,3R,5R)-3-(((4-(6-chloro-5-(trifluoromethyl)-1H-benzo[d]imidazol-2-yl)butyl)(methyl)amino)methyl)-5-(4-(cyclopropylamino)-7H-pyrrolo[2,3-d]pyrimidin-7-yl)cyclopentane-1,2-diol |
| B6 | (1R,2S,3R,5R)-3-(4-(cyclopropylamino)-7H-pyrrolo[2,3-d]pyrimidin-7-yl)-5-((isopropyl(4-(6-(trifluoromethyl)-1H-benzo[d]imidazol-2-yl)butyl)amino)methyl)cyclopentane-1,2-diol |
| B7 | (1R,2S,3R,5R)-3-(4-(cyclopropylamino)-7H-pyrrolo[2,3-d]pyrimidin-7-yl)-5-((methyl(4-(6-(trifluoromethyl)-1H-benzo[d]imidazol-2-yl)butyl)amino)methyl)cyclopentane-1,2-diol |
| B8 | (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(methyl)amino)methyl)cyclopentane-1,2-diol |
| B9 | (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(isopropyl)amino)methyl)cyclopentane-1,2-diol trihydrochloride |
| B10 | 1-(3-(((((1R,2R,3S,4R)-4-(6-amino-9H-purin-9-yl)-2,3-dihydroxycyclopentyl)methyl)(methyl)amino)propyl)-3-(4-(tert-butyl)phenyl)urea |
| B11 | N-(4-(5-(tert-butyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide |
| B12 | N-(4-(6-chloro-5-(trifluoromethyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide |
| B13 | (1R,2S,3R,5R)-3-(4-amino-7H-pyrrolo[2,3-d]pyrimidin-7-yl)-5-(((4-(6-chloro-5-(trifluoromethyl)-1H-benzo[d]imidazol-2-yl)butyl)(methyl)amino)methyl)cyclopentane-1,2-diol |
| B14 | (1R,2S,3R,5R)-3-(4-amino-7H-pyrrolo[2,3-d]pyrimidin-7-yl)-5-(((4-(6-chloro-5-(trifluoromethyl)-1H-benzo[d]imidazol-2-yl)butyl)(isopropyl)amino)methyl)cyclopentane-1,2-diol |
| B15 | N-(((1R,2R,3S,4R)-4-(4-amino-7H-pyrrolo[2,3-d]pyrimidin-7-yl)-2,3-dihydroxycyclopentyl)methyl)-N-(4-(6-chloro-5-(trifluoromethyl)-1H-benzo[d]imidazol-2-yl)butyl)methanesulfonamide |
| B16 | N-(((1R,2R,3S,4R)-4-(4-(cyclopropylamino)-7H-pyrrolo[2,3-d]pyrimidin-7-yl)-2,3-dihydroxycyclopentyl)methyl)-N-(4-(5,6-dichloro-1H-benzo[d]imidazol-2-yl)butyl)methanesulfonamide |
| B17 | N-(((1R,2R,3S,4R)-4-(4-(cyclopropylamino)-7H-pyrrolo[2,3-d]pyrimidin-7-yl)-2,3-dihydroxycyclopentyl)methyl)-N-(4-(5-(trifluoromethyl)-1H-benzo[d]imidazol-2-yl)butyl)methanesulfonamide |

Exhibit A
TABLE 3
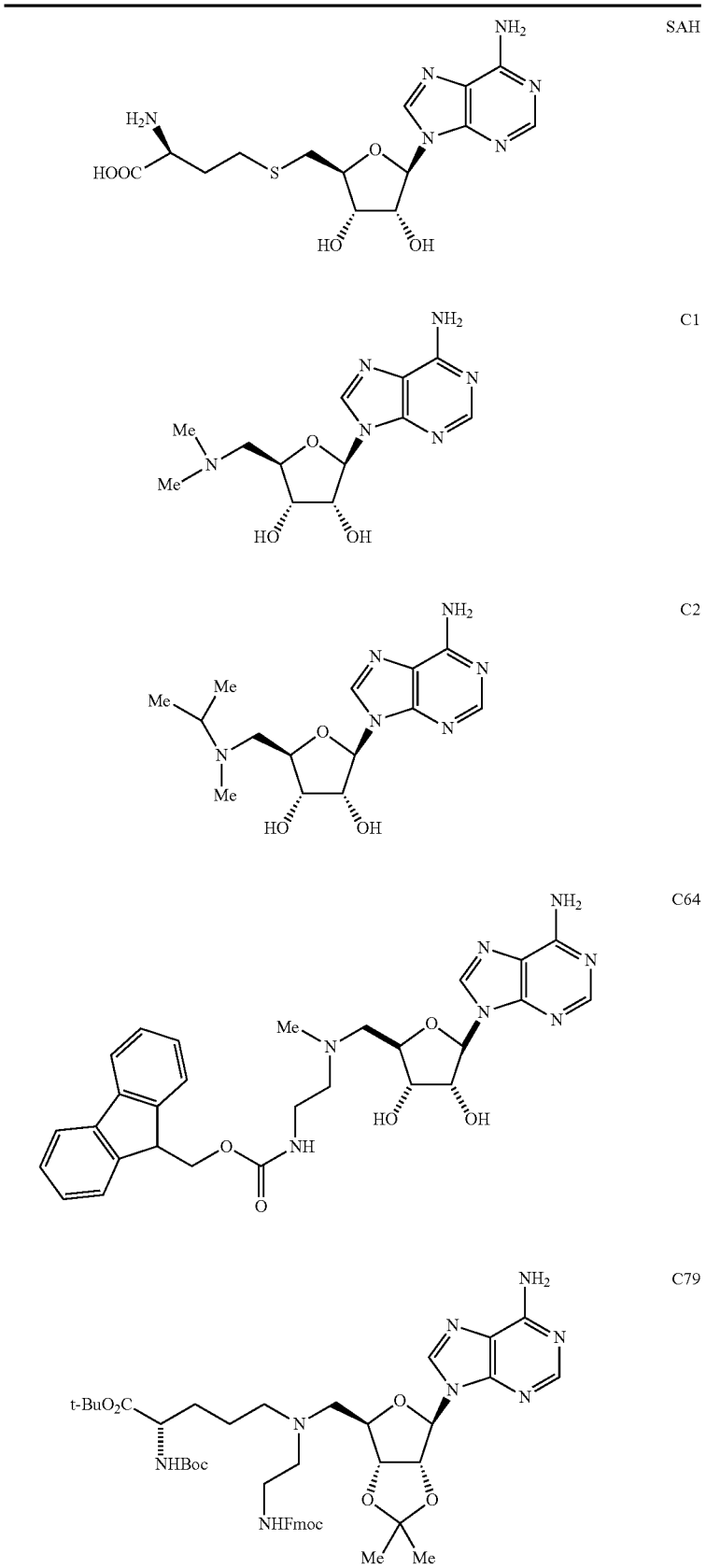

TABLE 3-continued
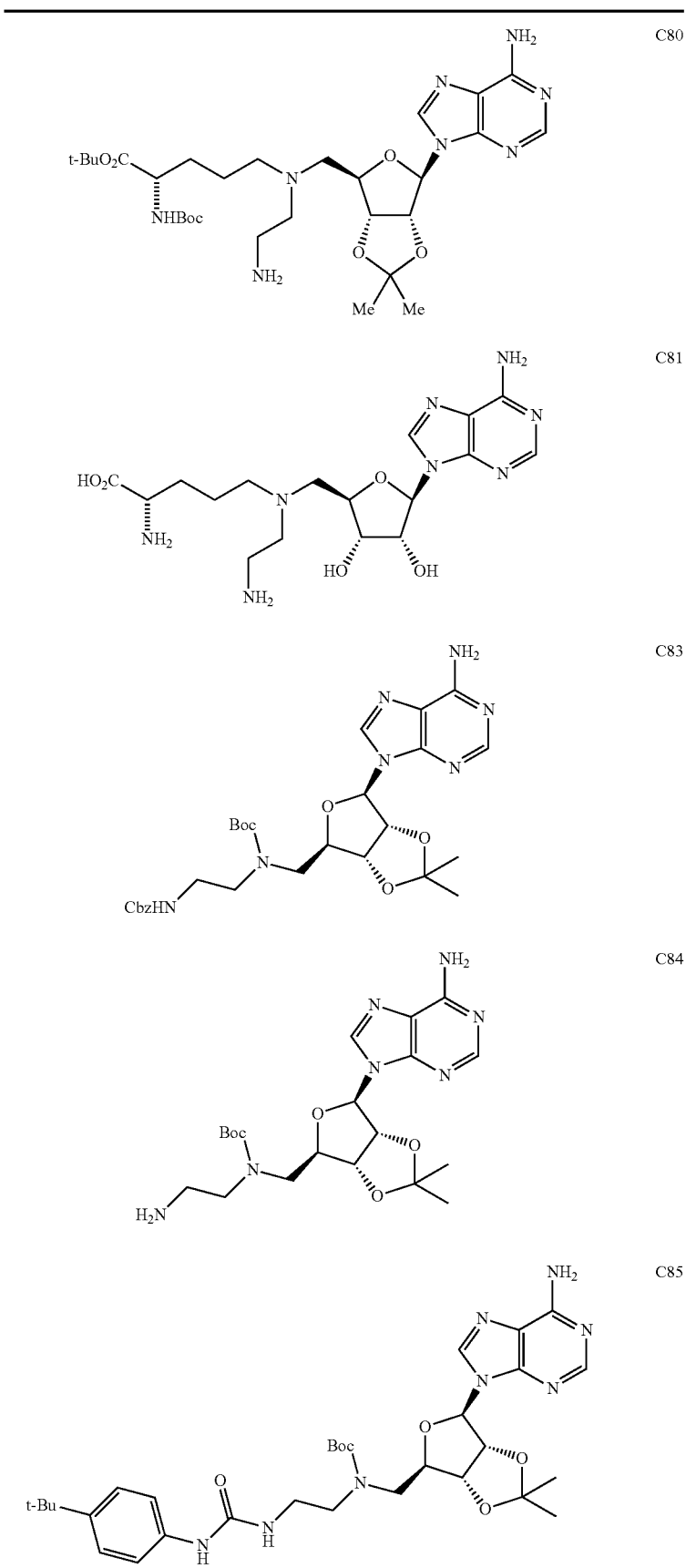

TABLE 3-continued
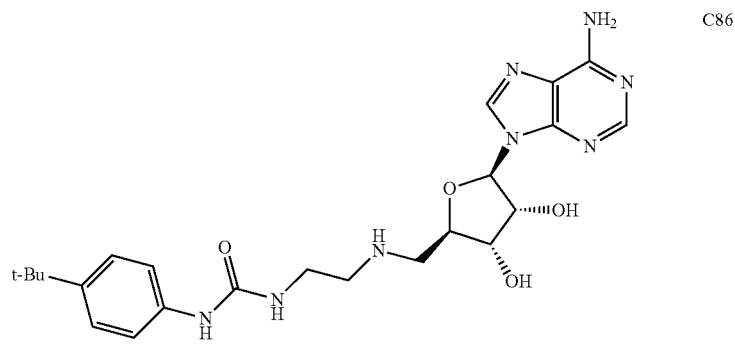
C86
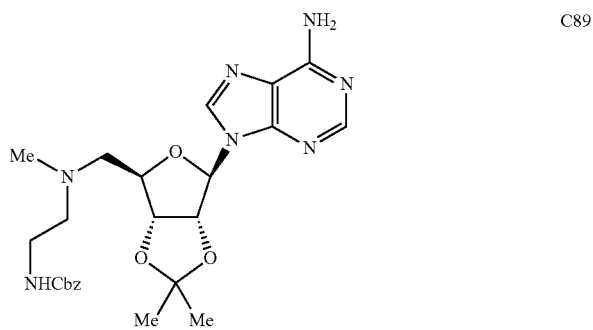
C89
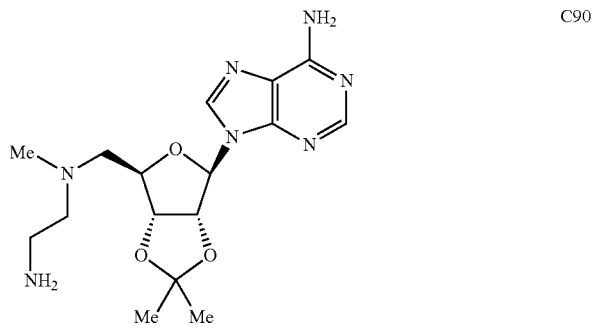
C90
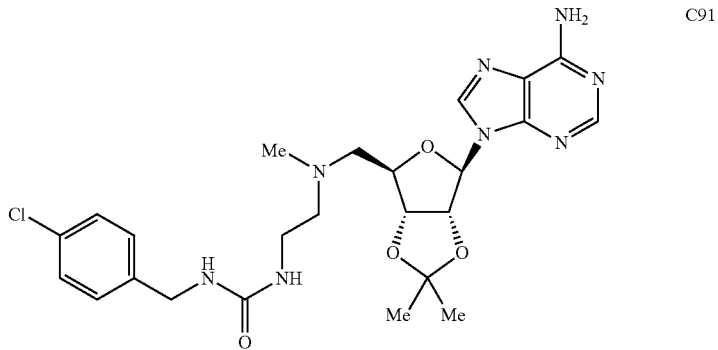
C91

TABLE 3-continued
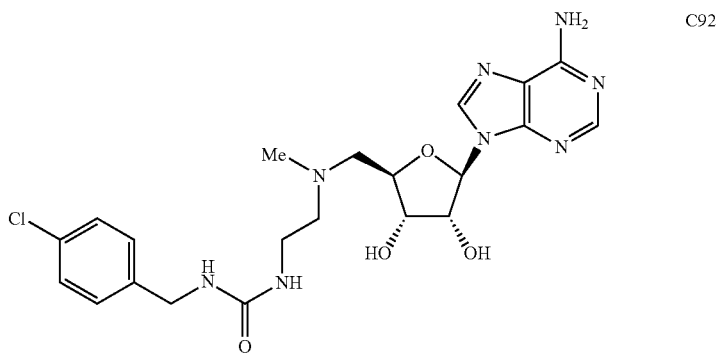
C92
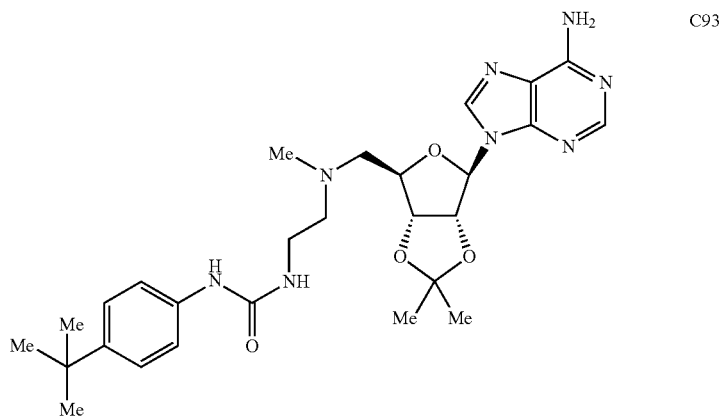
C93
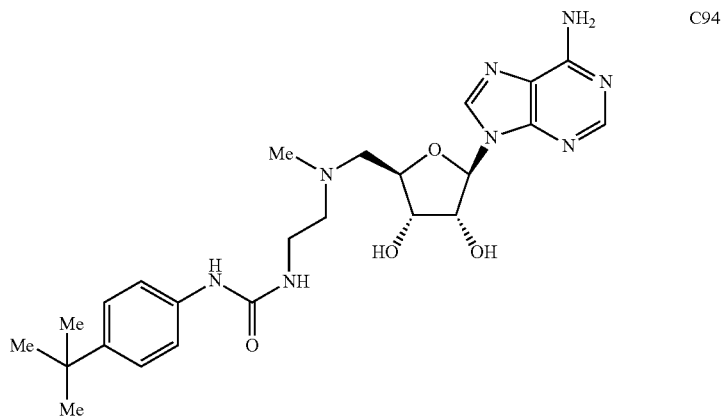
C94
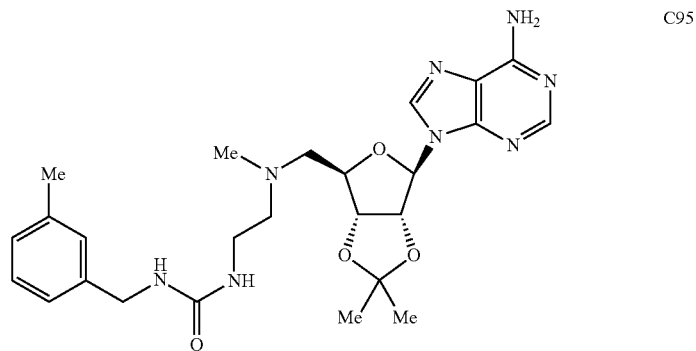
C95

TABLE 3-continued
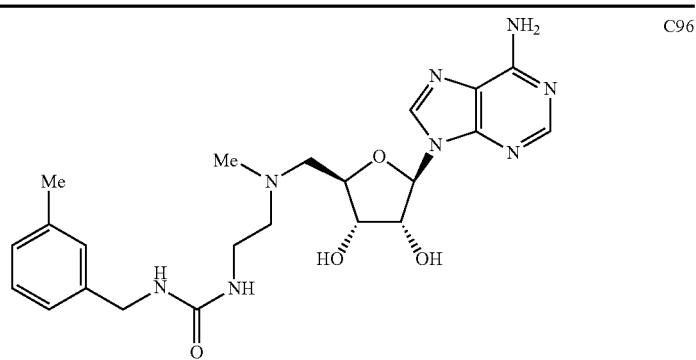
C96
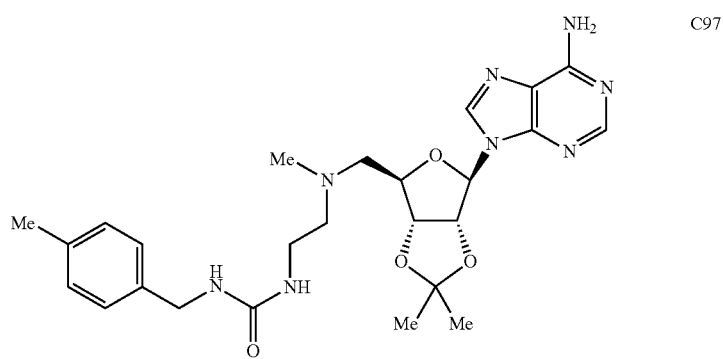
C97
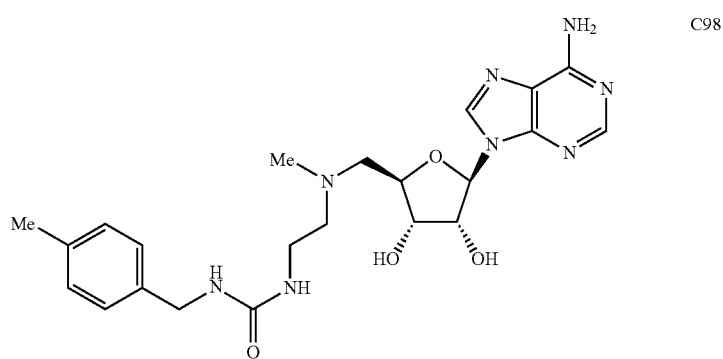
C98
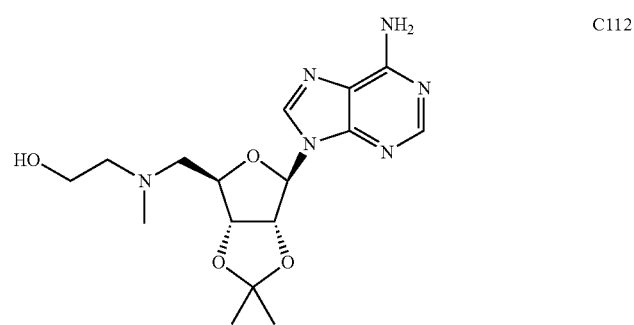
C112

TABLE 3-continued
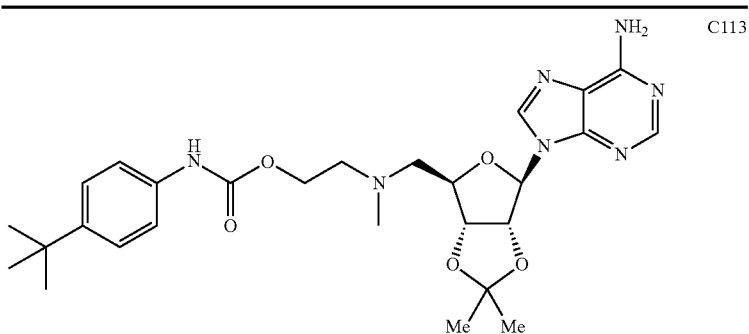
C113
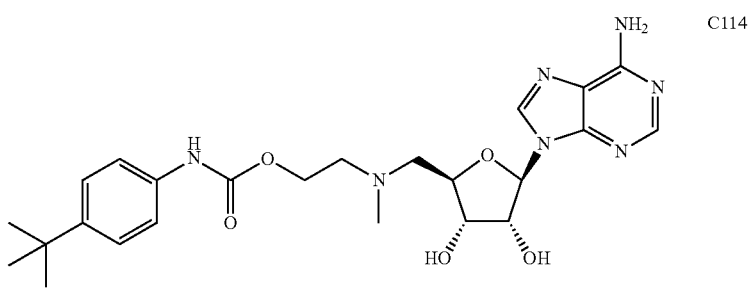
C114
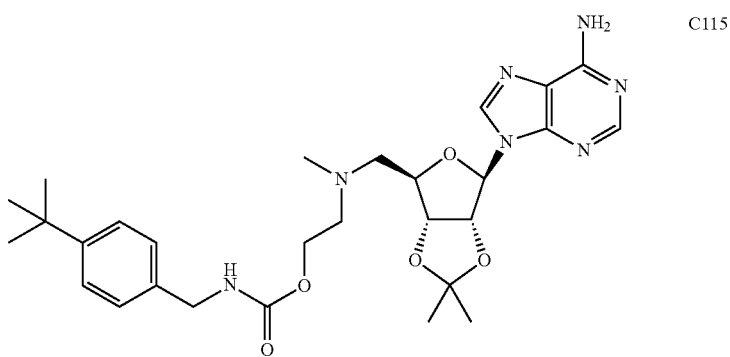
C115
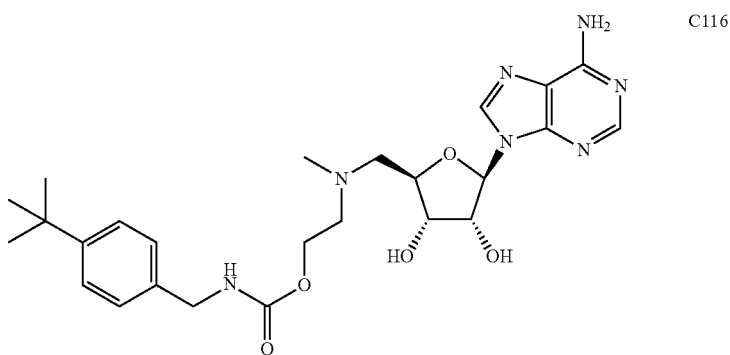
C116
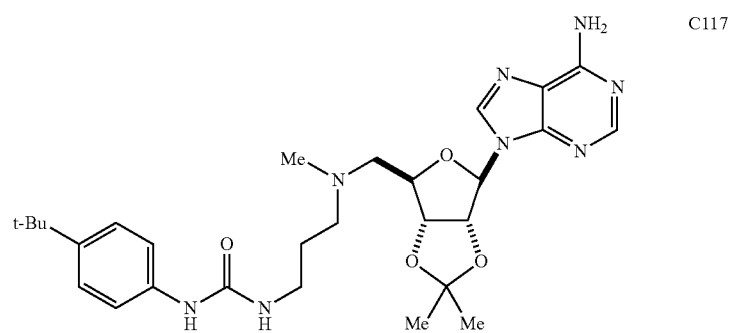
C117

TABLE 3-continued
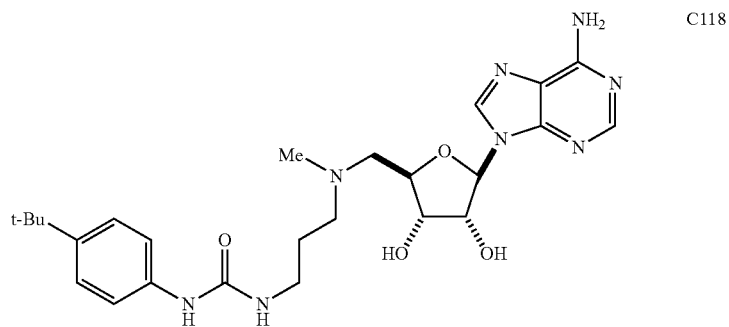
C118
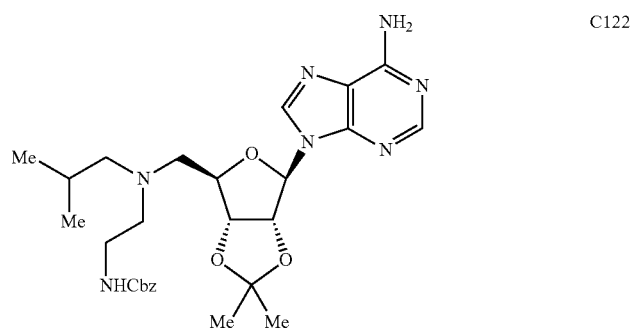
C122
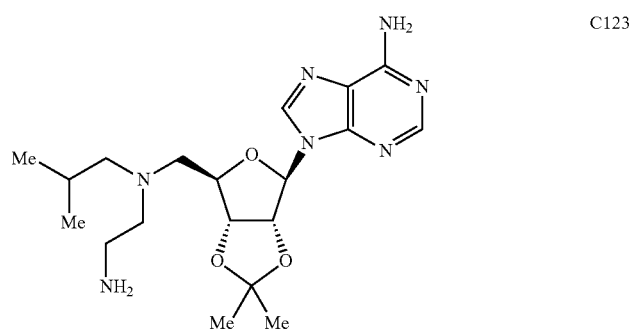
C123
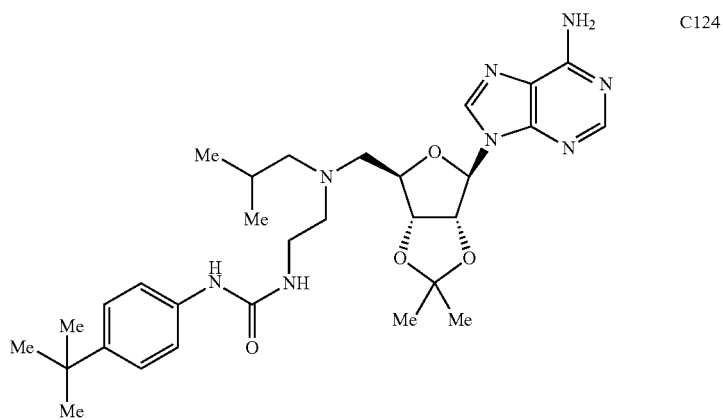
C124

TABLE 3-continued
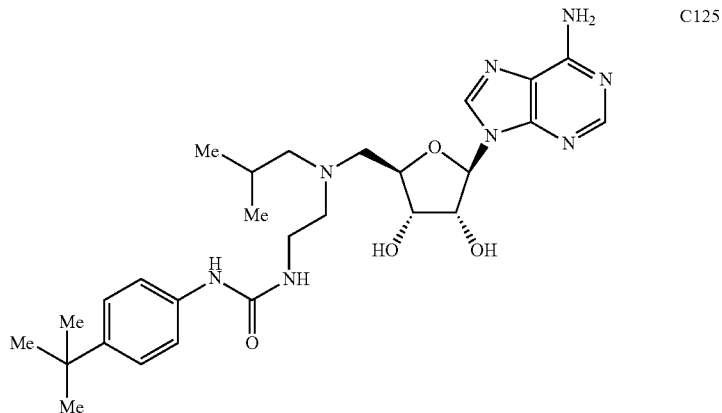
C125
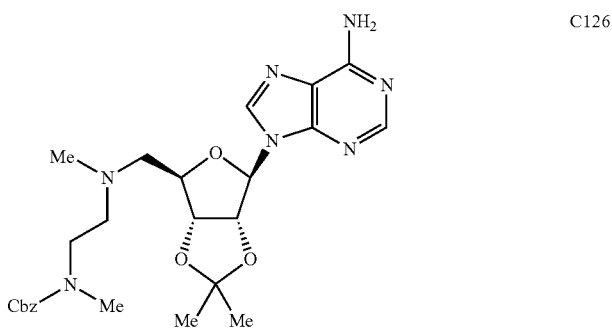
C126
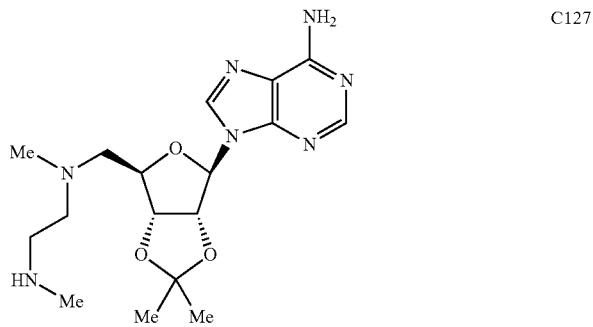
C127
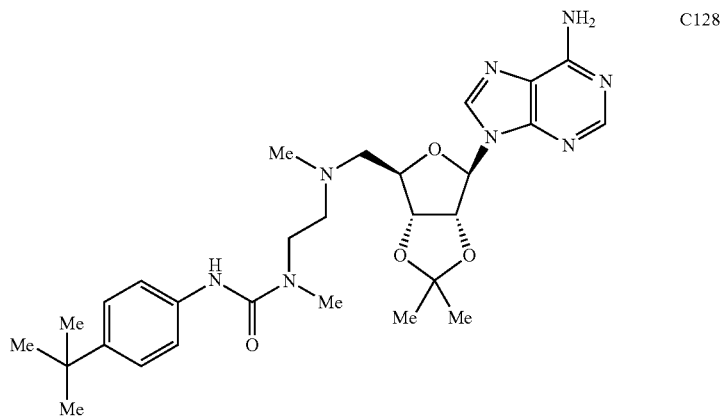
C128

TABLE 3-continued
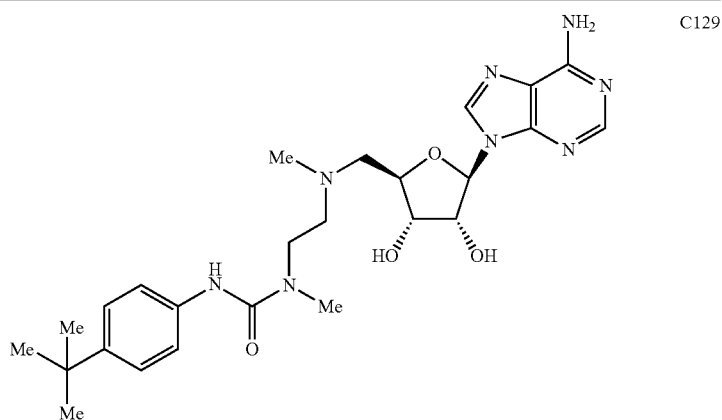
C129
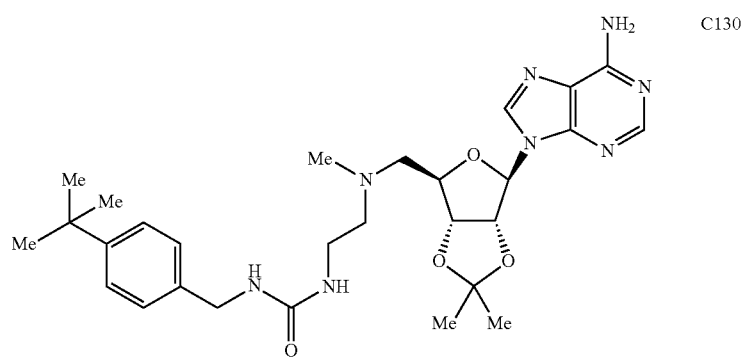
C130
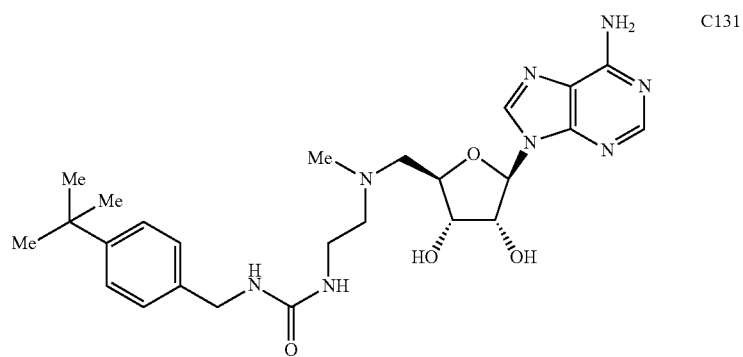
C131
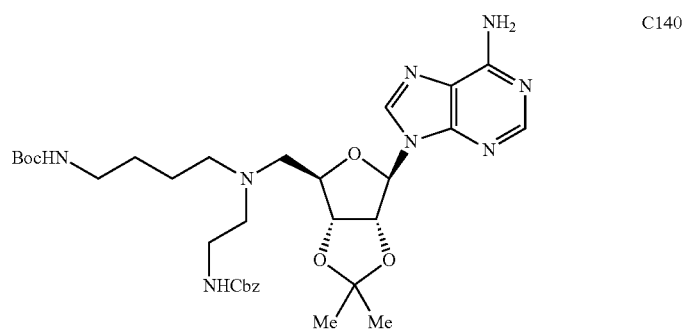
C140

TABLE 3-continued
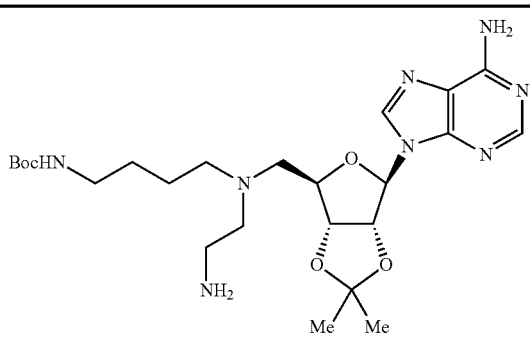
C141
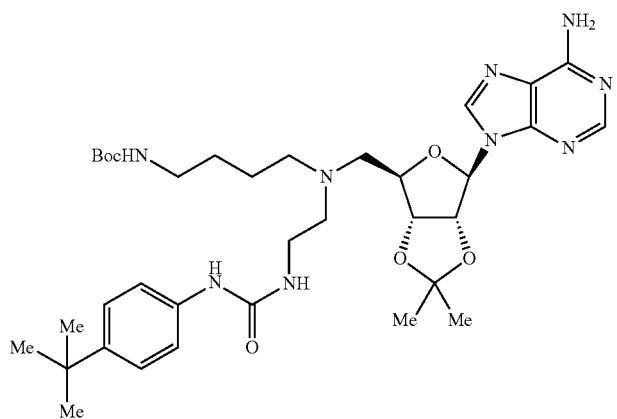 [SMILES: CC(C)(C)OC(=O)NCCCCN(CCNC(=O)Nc1ccc(C(C)(C)C)cc1)C[C@H]1O[C@@H](n2cnc3c(N)ncnc32)[C@@H]2OC(C)(C)O[C@@H]21]
C142
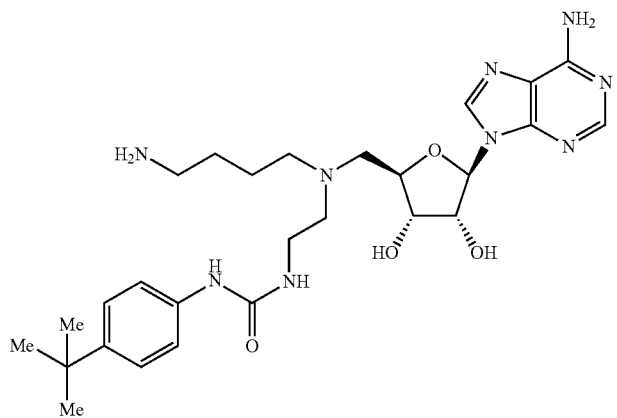 [SMILES: CC(C)(C)c1ccc(NC(=O)NCCN(CCCCN)C[C@H]2O[C@@H](n3cnc4c(N)ncnc43)[C@H](O)[C@@H]2O)cc1]
C143
Exhibit A
TABLE 4
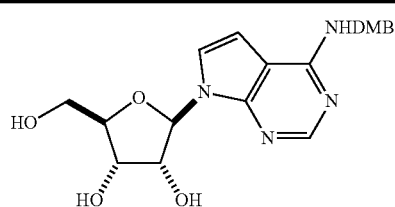
D1

TABLE 4-continued
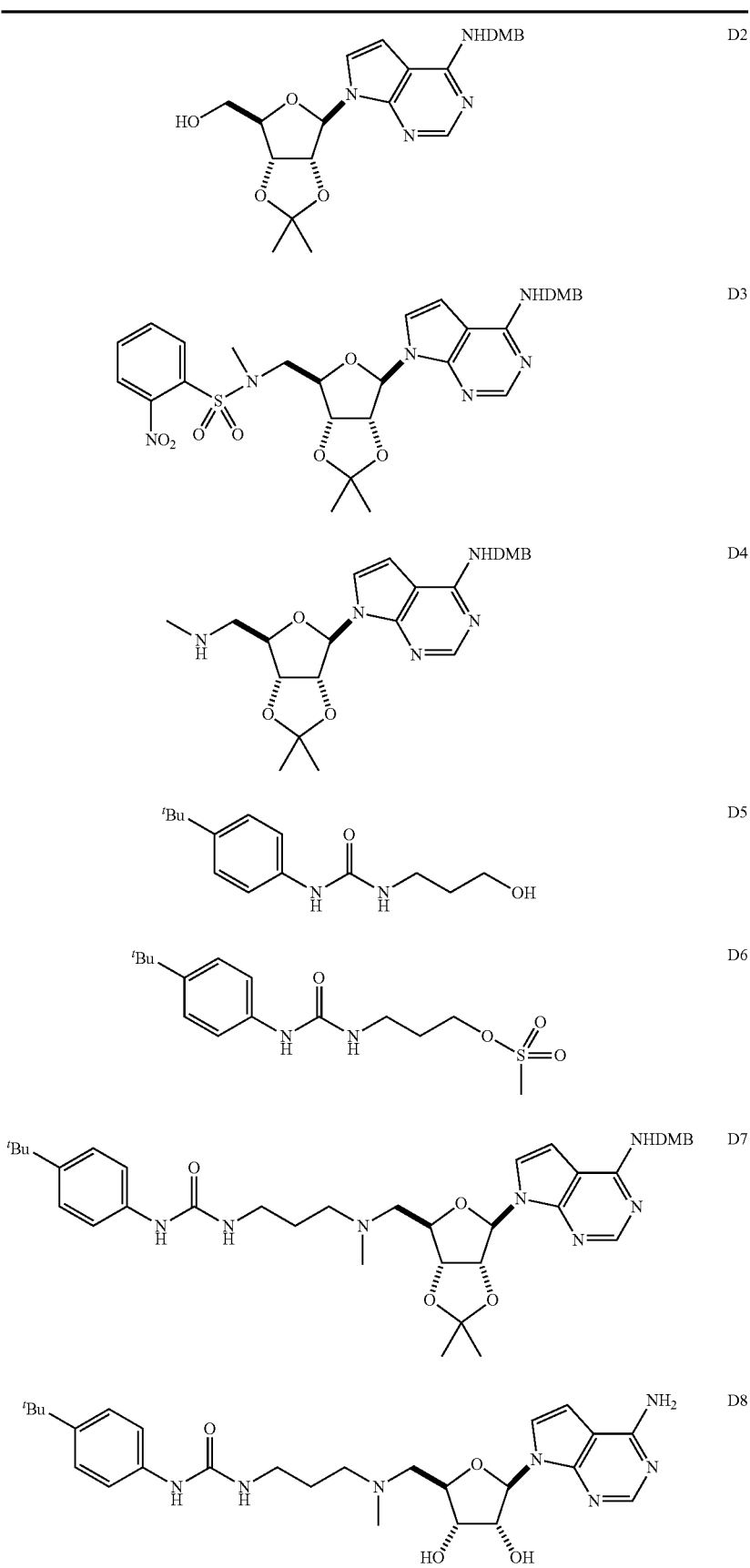

TABLE 4-continued
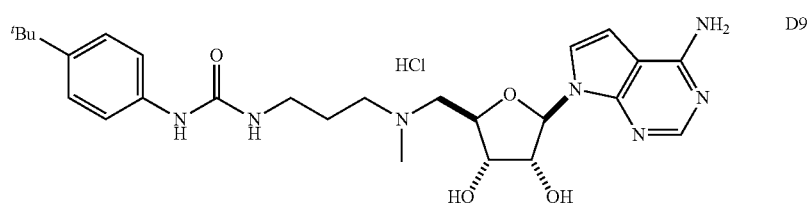
D9
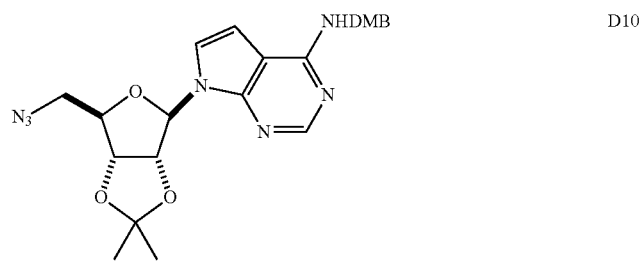
D10
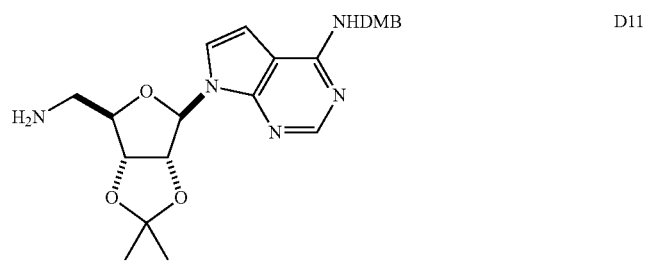
D11
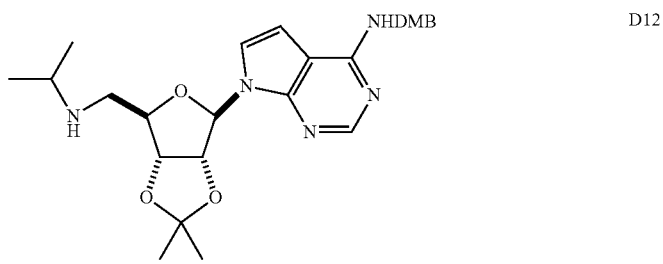
D12
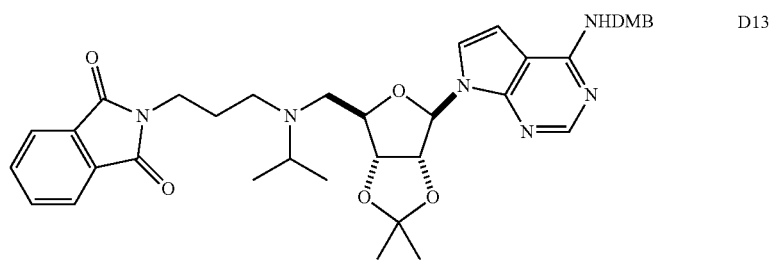
D13
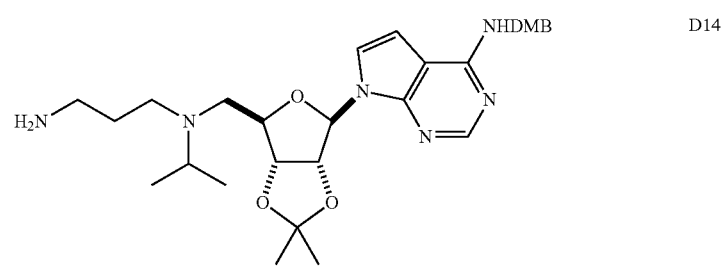
D14

TABLE 4-continued

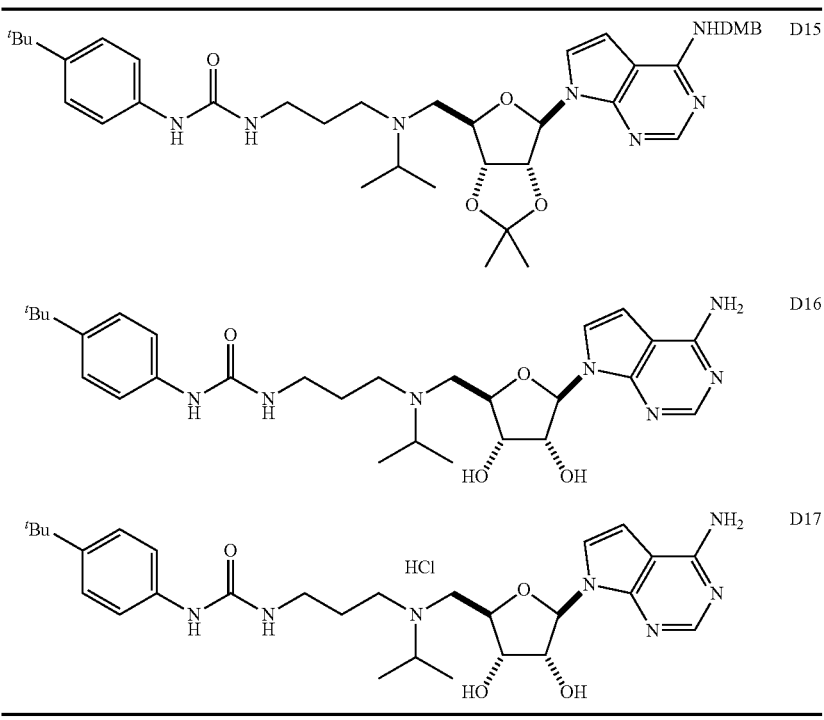

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups.

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups.

"Alkenyl" includes unsaturated aliphatic groups analogous in length and possible substitution to the alkyls described above, but that contain at least one double bond.

"Alkynyl" includes unsaturated aliphatic groups analogous in length and possible substitution to the alkyls described above, but which contain at least one triple bond.

Other optionally substituted moieties (such as optionally substituted alkenyl, alkynyl, cycloalkyl, heterocycloalkyl, aryl, or heteroaryl) include both the unsubstituted moieties and the moieties having one or more of the designated substituents.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5- or 6-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

For example, compounds of Formula (II) include those of the following chiral isomers and geometric isomers.

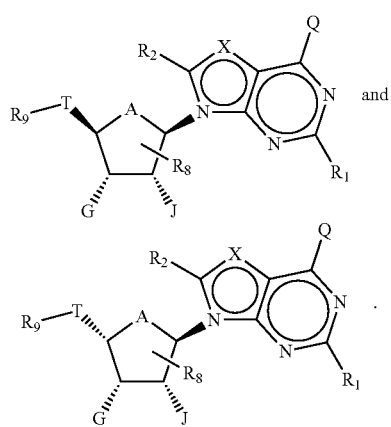

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

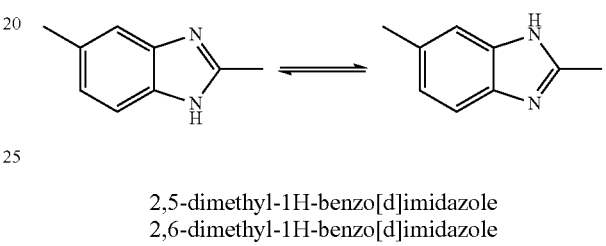

2,5-dimethyl-1H-benzo[d]imidazole
2,6-dimethyl-1H-benzo[d]imidazole

Another example of tautomerism is shown below.

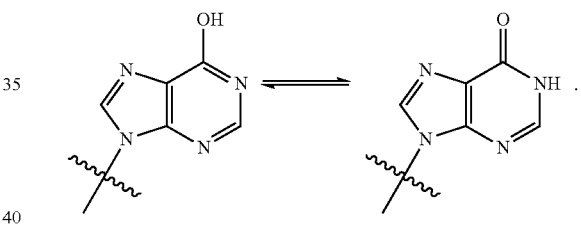

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of any of the Formulae disclosed herein or the DOT1L inhibitors identified by the methods of the invention include the compounds themselves, as well as their N-oxides, salts, their solvates, and their prodrugs, if applicable. A salt, for example, can be formed between an anion and a positively charged group (e.g., amino) on the compound or inhibitor (e.g., a substituted nucleoside compound such as a substituted purine or 7-deazapurine compound). Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on the compound or inhibitor (e.g., a substituted nucleoside compound such as a substituted purine or 7-deazapurine compound). Suitable cations include sodium ion, potassium ion, magnesium ion, calcium ion, and an ammonium cation such as tetramethylammonium ion. The compound or inhibitor (e.g., a substituted nucleoside compound such as a substituted purine or 7-deazapurine compound) also include those salts containing quaternary nitrogen atoms. Examples of prodrugs include esters and other pharmaceutically acceptable derivatives, which, upon administration to a subject, are capable of providing active substituted nucleoside compound such as a substituted purine or 7-deazapurine.

Additionally, the compounds of the present invention, for example, the salts of the compounds, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any of the Formulae disclosed herein. The present invention also provides detailed methods for the synthesis of various disclosed compounds of the present invention according to the schemes and the Examples described in WO2012/075381, WO2012/075492, WO2012/082436, and WO2012/75500, the contents of which are hereby incorporated by reference in their entireties.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below. $IC_{50}$ values are presented as A=<0.1 µM; B=>0.1 µM and <1 µM; C=>1 µM and <10 µM; and D=>10 µM and <50 µM.

| Compound | DOT1L $IC_{50}$ (µM) |
|---|---|
| A2 | 0.00074 |
| A3 | 0.00073 |
| A5 | 0.00059 |
| A69 | 0.00251 |
| A75 | 0.00059 |
| A86 | 0.00062 |
| A87 | 0.0008 |
| A91 | 0.00218 |
| A93 | 0.00292 |

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Assays of Enzymatic Activity

Unless otherwise indicated, assays of DOT1L enzymatic activity were performed under balanced conditions (all substrates present at concentrations equal to their respective $K_M$ values) using a radiometric assay of S-[methyl-$^3$H] adenosyl-L-methionine transfer from SAM to chicken erythrocyte nucleosomes as previously described. Reactions were initiated by addition of S-[methyl-$^3$H] adenosyl-L-methionine and allowed to run at room temperature for 120 minutes before being quenched by the addition of 800 µM cold SAM.

Compound $IC_{50}$ values were determined from assays of enzymatic activity in which compound was titrated into reaction mixtures by 3-fold serial dilution from DMSO stocks. For each titration, 10 concentrations of inhibitor were used along with 100% inhibition (2.5 µM SAH) and 0% inhibition (1 µL of neat DMSO per well) controls. Plots of residual enzyme velocity as a function of inhibitor concentration were fit to a standard Langmuir isotherm equation (12) to derive estimates of the $IC_{50}$ value of the compound. As described herein, the inhibition modality of key compounds within the aminonucleoside series were tested and always found to be competitive with SAM and noncompetitive with respect to nucleosome substrate. For most compounds, the $K_i$ value was calculated from the $IC_{50}$ value using the appropriate equation for competitive inhibition with respect to SAM.

For selected compounds, the inhibition modality with respect to the two substrates (SAM and nucleosomes) were determined by dual titration of compound and varied substrate concentration while holding the other substrate fixed at its $K_M$ value. Plots of velocity as a function of varied substrate at multiple inhibitor concentrations were globally fit to a general equation for enzyme inhibition using Graphpad Prism. Selection of the modality for each data set was done by evaluating the value of a, a term related to the degree of cooperative or anticooperative interaction between substrate and inhibitor binding, as previously described. A value of $\alpha \geq 10$ was taken as consistent with competitive inhibition, while a value of $\alpha \leq 0.1$ was taken as consistent with uncompetitive inhibition. Values of $\alpha$ between 10 and 0.1 were considered to be consistent with noncompetitive inhibition.

Compounds that displayed an $IC_{50}$ value within 50-fold of the enzyme concentration used in initial assays ([E]=0.25 nM) were treated as tight binding inhibitors. In this case, the $K_i$ value was determined by measuring the $IC_{50}$ value of the compound (vide supra) at varying concentrations of enzyme from 5 nM to 0.25 nM. A plot of $IC_{50}$ as a function of enzyme concentration was fit to a linear equation and the y-intercept value was equivalent to $K_i(1+[S]/K_M)$ where [S] and $K_M$ refer to SAM, the substrate with which these inhibitors compete. Knowing the values of [S] and $K_M$ used in the assay, the $K_i$ value was then calculated from the y-intercept value.

Determination of Ligand Association and Dissociation Rate Constants

Ligand association and dissociation rate constants were determined by surface plasmon resonance (SPR). DOT1L was stored in 20 mM Tris-HCl, 200 mM NaCl, 1 mM EDTA, 1 mM DTT, pH 7.8 and immobilized by direct amine coupling, diluting enzyme into coupling buffer containing 10 mM Hepes pH 7.4, 1 mM TCEP. Immobilization run buffer contained 10 mM Hepes pH 7.4, 150 mM NaCl, 500 µM TCEP, and approximately 10,000 RUs (response units) of DOT1L was captured. A reference channel of a surface that was activated in parallel and blocked was created in a second flow cell was also created. Data was captured on either a Biacore 4000 (chip CM5) or a Biorad ProteOn (chip GLM).

$K_d$ determinations were determined using run buffer containing 20 mM Tris pH 8.0, 10 mM NaCl, 100 mM KCl, 0.002% Tween-20, 500 µM TCEP, 2% DMSO, with the following injection parameters: 30 µl/min flow rate, with a 30 second association phase followed by monitoring dissociation for 30 seconds. Experiments were carried out at 25° C.

Cell Proliferation Assay

The human leukemia cell line MV4-11 harboring the MLL-AF4 translocation was obtained from ATCC (CRL-9591). Cells were grown in Iscove's Modified Dulbecco's Medium (IMDM) with 10% Fetal Bovine Serum (FBS). All cell culture reagents were purchased from Invitrogen Life Technologies and cells were maintained in a humidified incubator set to 37° C., 5% $CO_2$.

Cell proliferation was assessed by plating, in triplicate, exponentially growing MV4-11 cells in a 96 well plate at a density of $3 \times 10^4$ cells/well in a final volume of 150 µL. Cells were incubated in the presence of compound at increasing concentrations up to 50 µM. Viable cell numbers were determined every 3-4 days for a total of 14 days using the Guava Viacount assay (Millipore #4000-0040). Analysis was performed on a Guava EasyCyte Plus instrument (Millipore) according to the manufacturer's protocol. On days of cell counts, growth media and compound were replaced and cells split back to a density of $5 \times 10^4$ cells/well. Total cell number is expressed as split-adjusted viable cells per well. $IC_{50}$ values were determined from concentration dependent curves at day 14 using the Graphpad Prism software.

H3K79me2 Quantitative ELISA

Exponentially growing MV4-11 cells were seeded in a 12-well plate at $2 \times 10^5$ cells/well in a final volume of 2 mls. Cells were incubated in the presence of increasing concentrations of Compound C94, C118, or D16 up to 50 µM. Control cells were treated with 0.2% DMSO control. Cells ($1-2 \times 10^6$) were harvested after 96 hours of compound incubation and histones were extracted. An indirect enzyme-linked immunosorbent assay (ELISA) using acid extracted histones was run using matching microtiter plates (Immulon 4HBX #3855, Thermo Labsystems). Plates were coated for total H3 and H3K79me2 detection with either 75 ng or 1500 ng/well of histones respectively. The coating antigen was diluted in coating buffer (PBS+0.05% BSA) for a final volume of 100 µl and allowed to incubate overnight. The plates were blocked with 300 µl blocking buffer (PBST+2% BSA) for 2 hours at RT, followed by a 2 hour incubation with 100 µl primary antibody (1:750 H3K79me2, CST 5472; or 1:5000 total H3, Abcam ab1791) diluted in blocking buffer at RT. 100 µl of HRP tagged goat-anti-rabbit antibody (1:4000, CST 7074) in blocking buffer was added and allowed to incubate for 2 hours at RT. The reaction was visualized with 100 µl 3,3',5,5' tetramethylbenzidine substrate (TMBS, BioFx Laboratories) and stopped with an equivalent volume of 1 N sulfuric acid. Plates were read at 450 nm on an M5e plate spectrophotometer. Following each step, plates were washed 3 times with wash buffer (PBST), with an additional wash included following secondary antibody.

Quantitative Real-Time PCR Analysis

Exponentially growing MV4-11 cells were plated in a 12 well plate at $2\times10^5$ cells/well in a final volume of 2 mL. Cells were incubated with increasing concentration of test compounds (e.g., Compounds C94, C118, and D16 up to 50 µM for 6 days. Compound and media were refreshed on day 4 and cells split back to $5\times10^5$ cells/well. Cells were pelleted and processed as previously described.

Example 1: Structure Determination of DOT1L with Compound

The production of His-DOT1L-1-416 (SEQ ID NO: 1) and crystallization with SAM have been reported previously. Compound C1 was pre-incubated with DOT1L-1-416 (SEQ ID NO: 1) in 10 fold molar excess and then co-crystallization was set up with the hanging drop method using solution containing 100 mM sodium acetate, 1.8-2.0 M ammonium sulfate, 5 mM Tris(2-carboxyethyl)phosphine (TCEP), pH 5.5, at 20° C. In order to observe the protein at a physiological pH, crystals were transferred using nylon loops into a pH 7.5 Tris buffer (100 mM Tris-HCl (pH 7.5), 2.0 M ammonium sulfate, 5 mM TCEP). This transfer was done stepwise by soaking the crystals over the course of one hour in successive mixtures of acetate and Tris buffers. The crystals were equilibrated in the final Tris buffer at pH 7.5 overnight at 20° C. The crystal were next transferred stepwise into cryoprotectant (25 mM Tris-HCl, 2.0 M ammonium sulfate, 30% glycerol, pH 7.5), and flash-frozen in liquid nitrogen. Data collection was done at beamline X12B at the National Synchrotron Light Source at Brookhaven National Labs, Upton, N.Y.

Figure 10A:
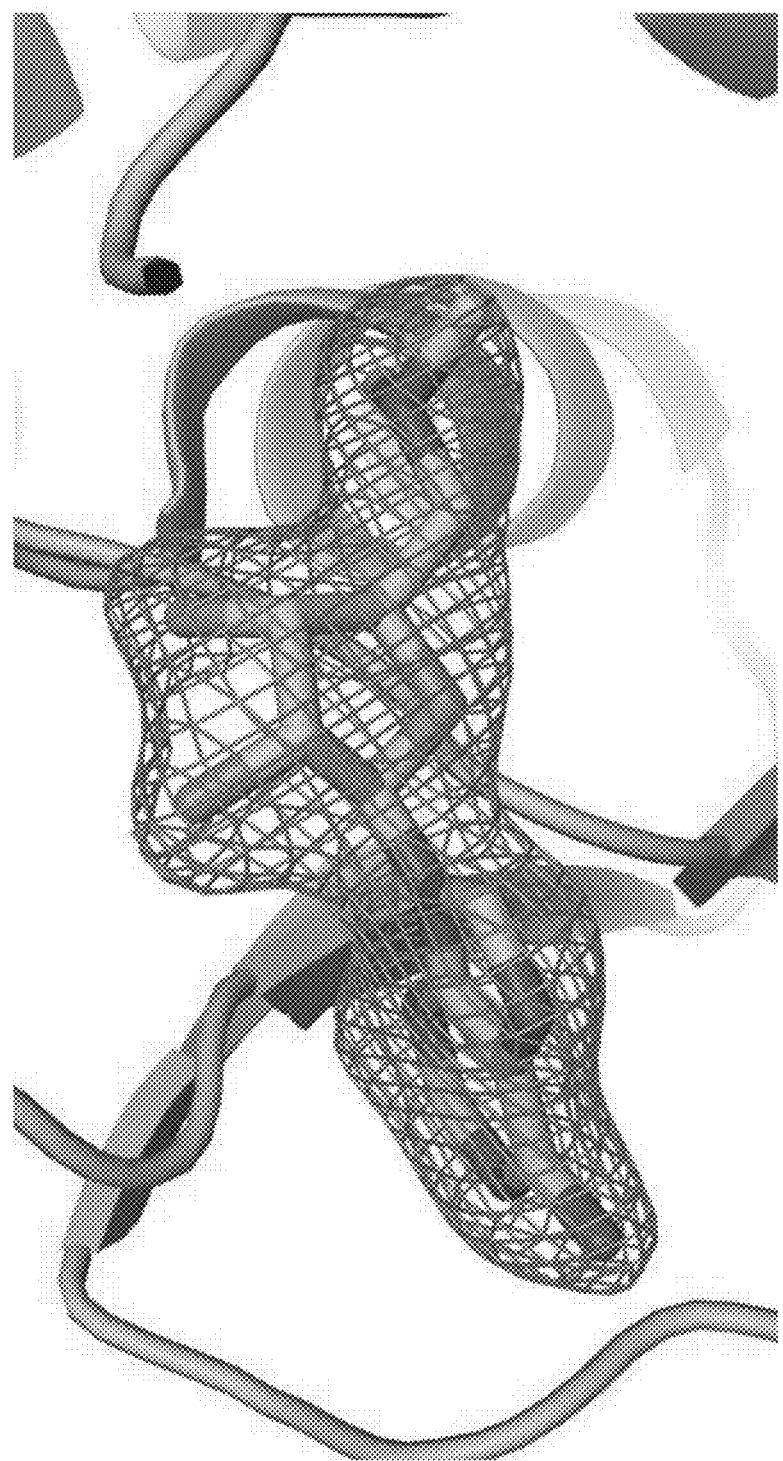
FIG. 10A shows a 2Fo-Fc map for Compound C1. This map was contoured at 1 σ.
Figure 10C:
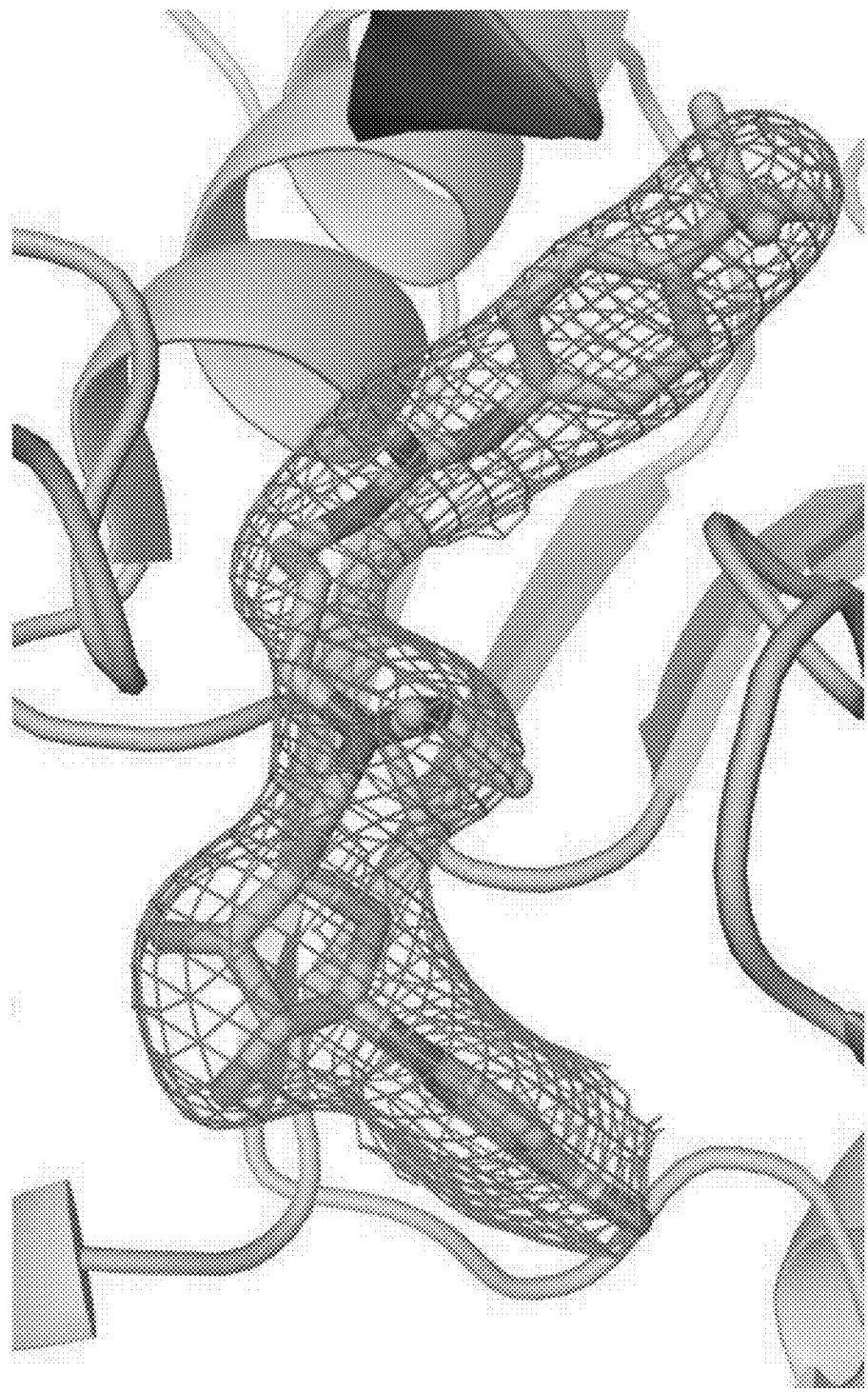
FIG. 10C shows a 2Fo-Fc map for Compound D16. This map was contoured at 1 σ.

For Compounds C118 and D16, DOT1L bound structures were obtained by the soaking method. The DOT1L-SAM crystals were cross-linked by exposing the crystal containing hanging drop over the vapor of 1 µl of 25% glutaraldehyde, pH 3.0, for 1 hr (13, 14) and then soaked with mother liquor containing 1 mM compound overnight. The crystals were cryo-protected with 35% glucose in mother liquor and flash-frozen in liquid nitrogen. The diffraction data sets were collected at beamline 17U at the Shanghai Synchrotron Radiation Facility. All data were processed by HKL2000. Structures were solved by molecular replacement (Phaser) using the DOT1L-SAM structure (PDB code:3QOW) with the SAM molecule removed as a search model. Refinement was carried out by Refmac5 and the model building was carried out by COOT. Detailed information of the diffraction data, refinement, and structure statistics are provided in Table 7 below. The 2fo-fc maps for the three ligands are shown in FIG. 10A-C. The coordinates for the crystal structures have been deposited with PDB code of 4EK9 (DOT1L-Compound C1), 4EKG (DOT1L-Compound C118) and 4EKI (DOT1L-Compound D16). Structural coordinates for DOTDOT1L-Compound D16 and DOT1L-Compound A2 are respectively provided in Tables S1 and S2 in the Appendix.

Example 2: Designing DOT1L Inhibitors

Mechanism-Guided Design Tenets

In the case of DOT1L, methyl transfer from the thiomethyl moiety of SAM to the ε-N of the bound side chain of lysine 79 of histone H3 (H3K79) proceeds through a simple $S_N2$ mechanism, requiring stringent alignment of the molecular orbitals of the methyl donor and acceptor atoms. The crystal structures of DOT1L bound to SAM and to the reaction product SAH illustrate a highly ordered active site with superimposable SAM and SAH configurations in the bound structure. The thiomethyl group of SAM is directed into a contiguous channel that forms the lysine binding pocket of the enzyme, thus facilitating facile group transfer once the ternary enzyme-SAM-histone complex has formed. Steady state kinetic analysis suggests that DOT1L functions by a distributive mechanism, requiring dissociation of the enzyme from the histone substrate after each round of lysine 79 methylation. The product SAH binds to DOT1L with relatively high affinity ($K_i$=320 nM), suggesting that product dissociation may be at least partially rate-limiting to enzyme turnover.

In one aspect of the invention, the above biochemical data provided a starting point for inhibitor design. The drug design started based on the structure of the reaction product SAH, with the following key objectives. First objective was to reduce the polar surface area of the ligand by replacement of charged and/or polar functionalities. Second objective was to engage recognition elements within both the SAM/SAH binding pocket and the adjacent lysine binding pocket to gain the affinity advantages of bisubstrate inhibitors. Lastly, these two goals should be accomplished while reasonable ligand efficiency is maintained and/or the pharmacological tractability of the compound series is improved.

The initial approach towards the above stated objectives was to replace the highly polarizable sulfur atom, eliminate the charged groups on the amino acid portion of SAH, and minimize the molecular mass contributed to by the amino acid side chain. To this end, the homocysteine moiety of SAH was replaced with a simple dimethyl amine to create a minimal pharmacophore, as represented by Compound C1. Despite these significant changes, Compound C1 retained a reasonable degree of binding affinity for DOT1L ($K_i$=38 µM); the binding free energy change ($\Delta\Delta G_{binding}$) for this compound, relative to SAH, was only 2.9 kcal/mol (at 25° C.). Additionally, crystallographic analysis of the binary complex of DOT1L and Compound C1 confirmed that, despite the S to N substitution, the compound binds within the active site of the enzyme in the same configuration as SAM. These data establish the utility of Compound C1 as a founder molecule for SAR (structure-activity relationship) elaboration.

Structure-Activity Relationships for SAH Mimetic DOT1L Inhibitors

The modification of Compound C1 by independent alterations to the alkyl side chains appended to the nitrogen atom of the 5' amine. Fixing one substituent as methyl, the second substituent was systematically varied with low molecular weight substituents with more effectively engaging recognition elements near the juxtaposition of the SAM and lysine binding pockets. To this end, a library of 25 compounds were prepared and tested for DOT1L inhibition. From this library the Compound C2 was identified, which demonstrated a DOT1L $K_i$ of 12 µM.

The isopropyl group of Compound C2 was speculated to reach into the lysine binding pocket. Based on this assumption, this functionality was further developed to further engage elements within this channel and simultaneously engage recognition elements within the amino acid binding pocket by varying the substituent. In the course of library building for these purposes, key intermediate species along the synthetic route were tested. The FMoc-protected intermediate Compound C64 displayed potency for inhibition of DOT1L, with a $K_i$ of 20 µM. The instability of this compound precluded detailed structural characterization by crystallography. This finding did, however, lead to replacing the functionality with a short tether, linked to a large hydrophobic group. Replacing the FMoc group with a tert-butyl phenyl urea resulted in Compound C94, which showed a marked improvement in potency ($K_i$=845 nM). Combining this replacement with an extension of the tether group by one methylene (from ethyl to propyl) led to even greater target engagement, as exemplified by Compound C118, a compound with a $K_i$ of 13 nM.

In one aspect of the invention, tolerance of DOT1L inhibitors for substitutions within the nucleoside portion of the pharmacophore was determined. In general, substitutions on the nucleoside were not well tolerated. However, the ring nitrogen at position 7 could be substituted by carbon; the resulting deazapurine compounds demonstrated potent inhibition of DOT1L as exemplified by compound D8, an inhibitor displaying a $K_i$ of 4 nM.

Combining the 7 deazapurine moiety with the tert-butyl phenyl urea and 5'-amino isopropyl groups (vide supra) yielded compound D16. As previously described, D16 is a potent ($K_i$=300 pM), selective inhibitor of DOT1L that demonstrates activity in inhibiting intracellular methylation of H3K79 and selective killing of MLL-rearranged leukemia cell lines. This compound also demonstrated a statistically significant survival advantage in an aggressive, disseminated mouse model of MLL-rearranged leukemia.

Conformational Adaptation Drives Inhibitor Potency and Long Residence Time

Conformational adaptation appears to play a critical role in driving inhibitor potency among the aminonucleoside inhibitors of DOT1L.

Table 5 below summarizes the kinetics of inhibitor association and dissociation with DOT1L for the enzymatic product SAH and for three key compounds (Compounds C94, C118 and D16), as measured by surface plasmon resonance.

tional gating of compound access to the SAM/SAH binding site. The upper limit of the association rate constant for diffusion-limited small molecule binding to a protein has been estimated to be on the order of $10^9$ $M^{-1}$ $s^{-1}$. More typically values of the association rate constant for small molecule substrates binding to enzymes are about $10^7$ $M^{-1}$ $s^{-1}$ and typical values for the residence time of enzyme substrates and products are in the millisecond to second range(23). Thus, even for the natural product of the enzyme, SAH, the rates of association and dissociation are slow relative to other natural ligands of enzymes. The crystal structures of SAM and SAH bound to DOT1L revealed an occluded active site with no clear, unobstructed pathway from bulk solvent to the active site for compound association or dissociation; thus some conformational adaptation must attend enzyme turnover in order for substrate to access the binding pocket and for product to be released.

These data also imply conformational adaptation of the enzyme in response to more potent (e.g., Compounds C118 and D16) inhibitor binding. Two possible conformational mechanisms are consistent with the data presented in Table 5. The first is referred to as a conformational selection mechanism in which the free enzyme exists in two conformational states that are in (slow) equilibrium with one another: a state that binds inhibitor and one that does not. Binding of the inhibitor shifts the equilibrium in favor of the inhibitor-binding conformation. The second mechanism is referred to as the induced-fit mechanism. In this model the inhibitor binds to the enzyme in a non-optimal conformational state and then induces a conformational adjustment of the enzyme to create a more complementary, tighter binding state of the binary enzyme-inhibitor complex. A third mechanism of slow association and slow dissociation results from situations in which the conformation of the enzyme

TABLE 5

| Compound | $K_i$ (nM) | $K_d$ (nM) [a] | $k_{on}$ ($M^{-1}s^{-1}$) | $k_{off}$ ($s^{-1}$) | τ (s.) |
| --- | --- | --- | --- | --- | --- |
| SAH | 320 ± 104 [b] | 71 ± 40 | 1.4 ± 0.5 (×$10^6$) | 0.1 ± 0.04 | 10 ± 1 |
| C94 | 845 ± 472 [b] | 167 ± 100 | 1.2 ± 0.8 (×$10^6$) | 0.2 ± 0.09 | 5 ± 3 |
| C118 | 13 ± 7 [b] | 1.7 ± 0.2 | 1.20 ± 0.1 (×$10^7$) | 0.02 ± 0.001 | 50 ± 3 |
| D16 | 0.30 ± 0.02 [c] | 0.10 ± 0.02 | 3.0 ± 0.4 (×$10^6$) | 3 ± 0.3 (×$10^{-4}$) | 3333 ± 300 |

[a] $K_d$ calculated as $k_{off}/k_{on}$.
[b] Errors represented as standard deviation (SD)
[c] $K_i$ determined from concentration-dependent effects of compound on enzyme activity as described in Materials and Methods; error represented as standard error of measurement (SEM)

First, as noted above, there was a significant jump in target potency between C94 and C118 ($\Delta\Delta G_{binding}$=2.3-2.5 kcal/mol at 25° C.) and again between C118 and D16 ($\Delta\Delta G_{binding}$=2.4-2.9 kcal/mol at 25° C.). The enhancement in target potency seen across this series appears to be driven by a reduction in the dissociation rate of the inhibitors from the binary enzyme-inhibitor complex ($k_{off}$) which results in a dramatic change in the residence time (τ) of the binary complex from 5 seconds to 1 hour in going from C94 to D16; while the dissociation rate constants and residence times change by over three orders of magnitude among these compounds, the association rate constant ($k_{on}$) is virtually invariant across the pharmacophore series and is several orders of magnitude slower than the calculated diffusion limit. More advanced inhibitors within the aminonucleoside series continue this trend, displaying residence times greater than 24 hours with no attendant change in association rate constant (such as Compound A2).

The relatively slow association rate constants seen for SAH and the aminonucleosides also suggest a conformadoes not change, but other factors limit the rate of ligand binding and dissociation. In this third situation, binding is often gated by the need for slow displacement of structured water molecules within the active site, displacement of metal binding ligands, and similar slow processes that are distinct from conformational adjustments of the protein per se.

The induced-fit mechanism is predominant among enzyme-inhibitor interactions. However the current data do not allow one to definitively distinguish between the two conformational adaptation models described above. In either case, the low-affinity conformational state appears to be kinetically (and thermodynamically) insignificant in terms of inhibitor interactions. This is evident from the excellent agreement between the $K_i$ values for the inhibitor series, determined from the concentration dependent effects of compounds on enzyme activity, and the $K_d$ values determined from the SPR binding experiments (Table 5). The $K_d$ values in Table 5 are calculated simply as the ratio of $k_{off}$ over $k_{on}$, thus assuming a single step binding and dissociation mechanism. If an intervening conformational state were kinetically significant in the inhibitor binding pathway, one would expect to see biphasic association curves in the enzymatic assay or the SPR binding or both. The good agreement between the $K_i$ and simply calculated $K_d$ values here argues against a significant kinetic role for an intervening conformational state. A similar situation is encountered in other enzyme-inhibitor systems that work through an induced-fit mechanism for which the initial encounter complex is kinetically insignificant and rapidly isomerizes to the final conformational state of the tight-binding enzyme-inhibitor complex.

Structural Changes Attending Inhibitor Binding

Figure 2A:
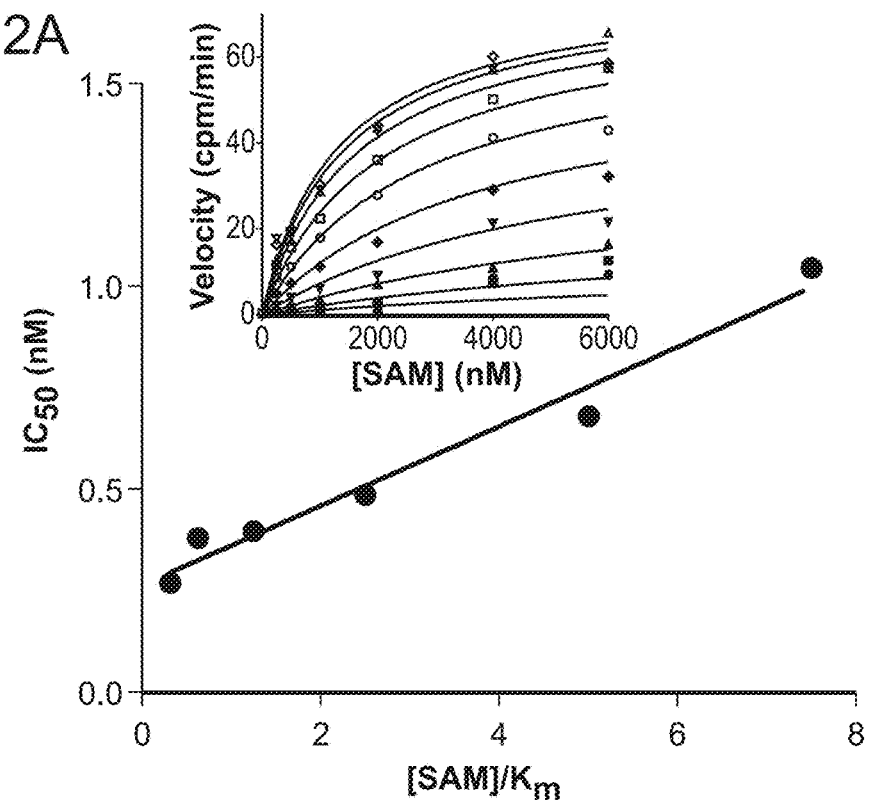
FIG. 2A is a plot showing biochemical characterization of Compound D16 inhibition of DOT1L. Compound D16 is a competitive inhibitor with respect to SAM. The $IC_{50}$ of Compound D16 was determined as a function of SAM concentration relative to the $K_m$ of SAM ($[SAM]/K_m$) and found to display a linear relationship as expected for competitive inhibition. Inset: Michaelis-Menten plot of product formation as a function of SAM concentration at various concentrations of Compound D16. The data were fit globally to a general equation for enzyme inhibition (Copeland R A, *Evaluation of enzyme inhibitors in drug discovery. A guide for medicinal chemists and pharmacologists.* New York: Wiley; 2005) and yield values of alpha of 10±6 and $K_i$ of 0.3±0.03 nM.
Figure 2B:
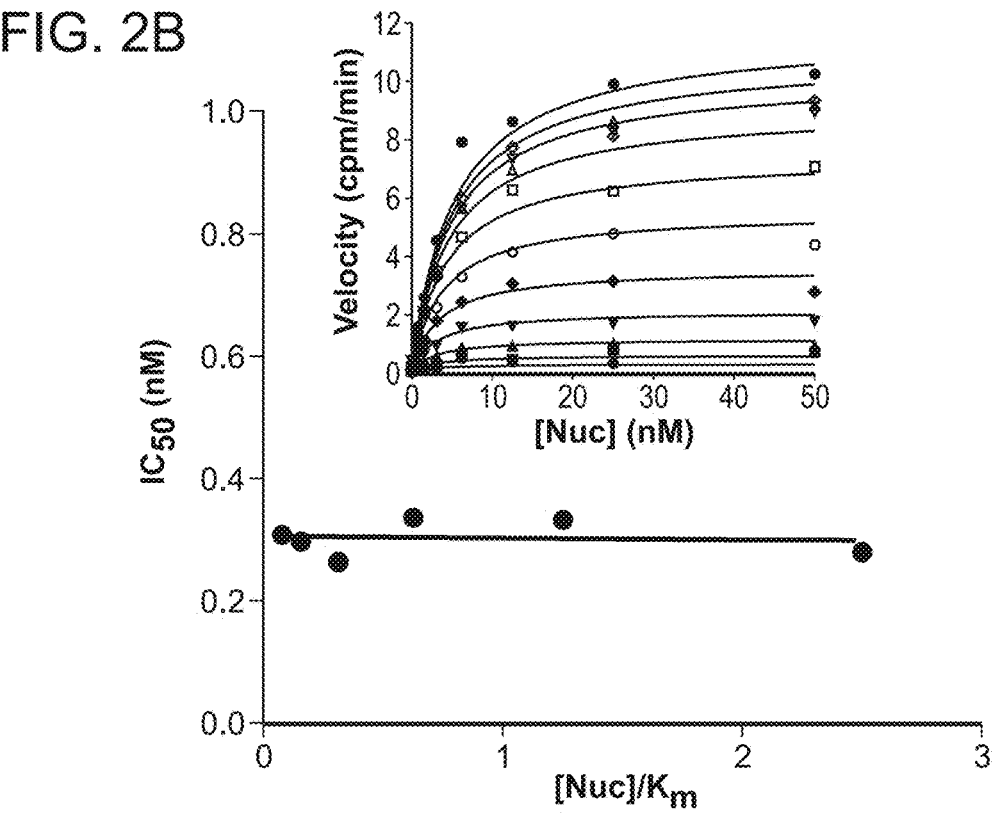
FIG. 2B is a plot showing biochemical characterization of Compound D16 inhibition of DOT1L. Compound D16 is a noncompetitive inhibitor with respect to oligonucleosome (Nucl). The $IC_{50}$ of Compound D16 was determined as a function of Nuc concentration relative to the $K_m$ of Nucl ($[Nucl]/K_m$) and found to be independent of $[Nucl]/K_m$, as expected for noncompetitive inhibition. Inset: Michaelis-Menten plot of product formation as a function of Nuc concentration at various concentrations of Compound D16. The data were fit globally to a general equation for enzyme inhibition (Copeland, 2005) and yield values of alpha of 0.5±0.2 and $K_i$ of 0.3±0.02 nM.
Figure 3:
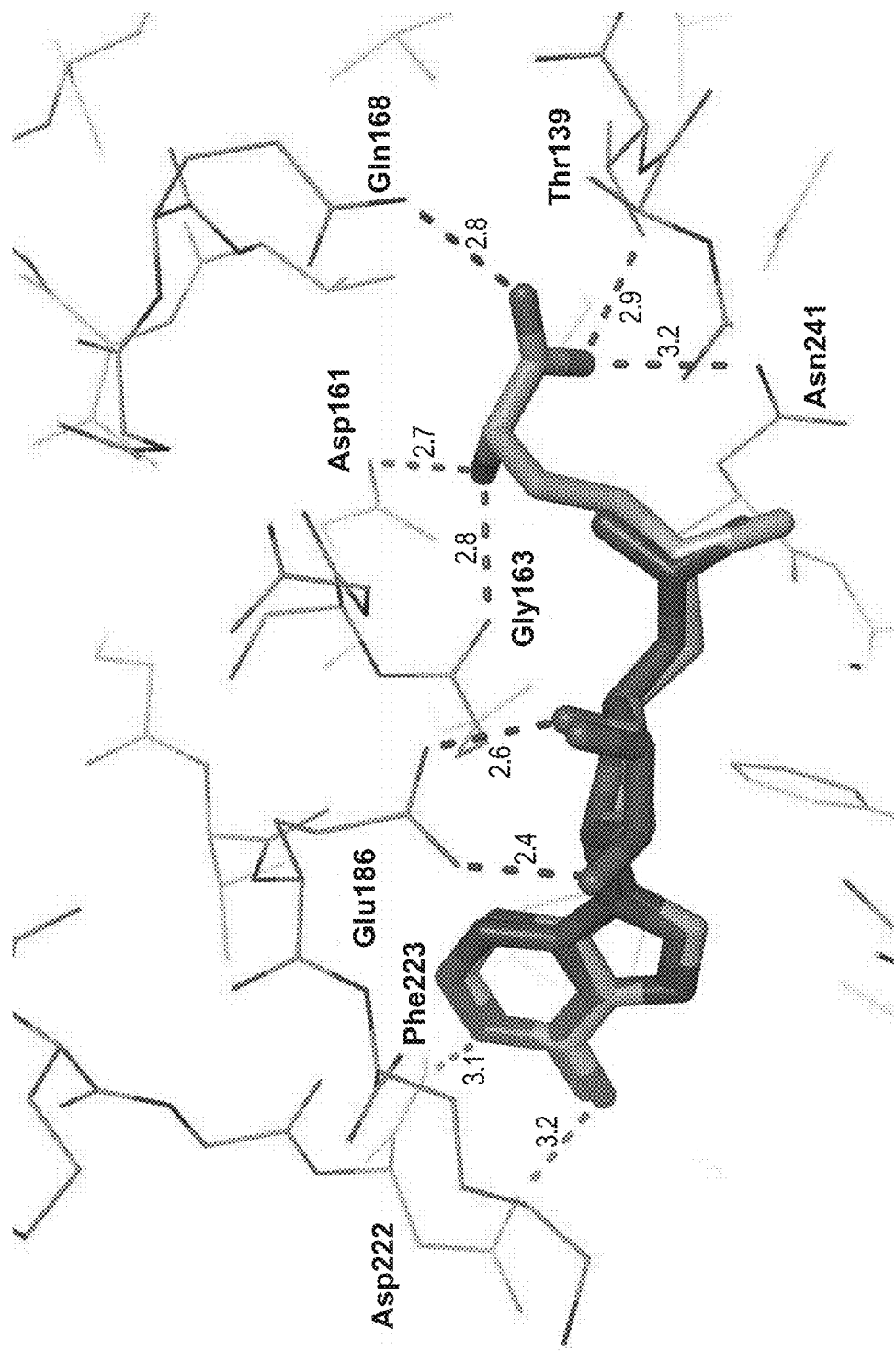
FIG. 3 is a plot showing superposition of SAM and Compound C1 within the active site of DOT1L, demonstrating conservation of binding motif. DOT1L-SAM co-crystal structure (PDB code: 3QOW): in line presentation (carbon atoms: light blue; oxygen: red; nitrogen: dark blue). SAM: stick presentation (carbon atoms: light blue; oxygen: red; nitrogen: dark blue, sulfur: yellow). Compound C1: stick presentation (carbon atoms: maroon; oxygen: red; nitrogen: dark blue). Hydrogen bonds between SAM and DOT1L are labeled by dashed lines.

The inference drawn from the binding kinetics of conformational adaptation in DOT1L-inhibitor interactions is supported by crystallographic analysis of the structures of DOT1L-inhibitor binary complexes. Steady state kinetic analysis of DOT1L inhibition by the aminonucleosides consistently demonstrated competitive inhibition with respect to SAM and noncompetitive inhibition with respect to nucleosome (as exemplified for Compound D16 in FIG. 2). This kinetic characterization is consistent with the crystallographic data that demonstrates compound binding within the SAM/SAH binding pocket for all tested compounds. As described above, the structures of the founder Compound C1 and SAH are virtually superimposable (FIG. 3). The more potent Compounds C118 and D16 both contain an extended (i.e., propyl) tether and terminal hydrophobic groups appended to the 5' amino nitrogen. It was initially expected that these extended structures would reach into the proximal lysine binding channel of the enzyme, creating a bisubstrate-like mode of inhibitor interaction. However, the crystal structure of DOT1L-Compound C118 reveals an unanticipated mode of interaction with the enzyme.

Figure 4A:
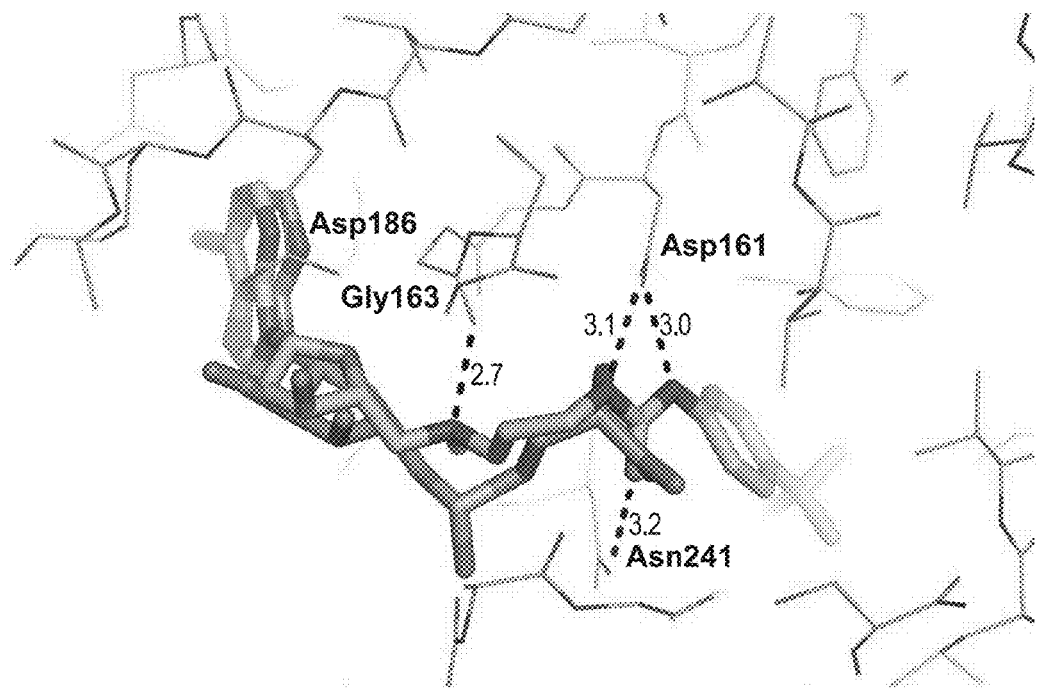
FIG. 4A shows key contacts between DOT1L protein and the urea moiety of Compound C118 in the DOT1L-Compound C118 co-crystal structure. SAM is superimposed on to Compound C118. The interactions for 5'-amino and urea of Compound C118 are labeled by dashed lines. DOT1L protein of the DOT1L-Compound C118 co-crystal structure: in line presentation (carbon atoms: green; oxygen: red; nitrogen: dark blue). Compound C118: stick presentation (carbon atoms: green). SAM: stick presentation (carbon atoms: light blue)
Figure 4B:
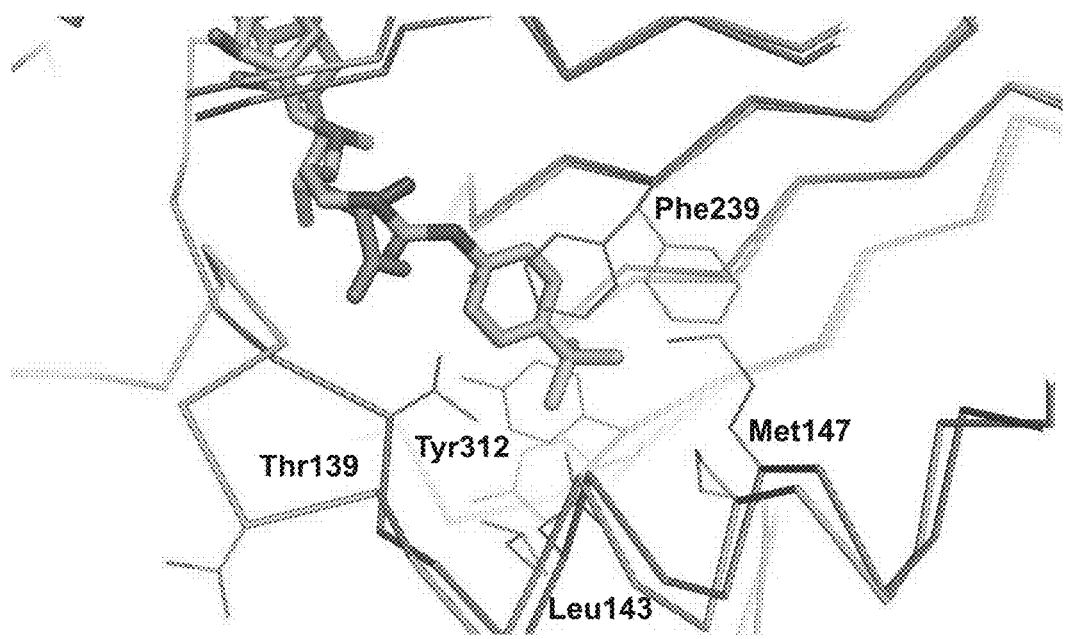
FIG. 4B shows opening of the hydrophobic pocket within the DOT1L-Compound C118 co-crystal structure. Superimposition of DOT1L-SAM and DOT1L-Compound C118 demonstrates the opening of the hydrophobic pocket by the tert-butyl phenyl group on Compound C118. DOT1L structures are presented in Cα trace. The key residue side chains which open the pocket are displayed as in line presentation. Comparison of these residues in the DOT1L-SAM and DOT1L-Compound C118 structures shows the conformational change and resultant opening of the hydrophobic pocket upon the binding of Compound C118. DOT1L protein: in line presentation (carbon atoms: green for the DOT1L-Compound C118 structure and light blue for the DOT1L-SAM structure; oxygen: red; nitrogen: dark blue). Compound C118: stick presentation (carbon atoms: green). SAM: stick presentation (carbon atoms: light blue)

The DOT1L-Compound C118 structure reveals that the inhibitor reaches into a heretofore-unrecognized pocket immediately adjacent to the amino acid binding subsite of the SAM/SAH binding pocket of the enzyme (FIG. 4). This pocket—which does not exist in the structures of the enzyme with SAM, SAH or Compound C1—is opened up by the tert-butyl phenyl urea functionality of Compound C118. More specifically, the crystal structure of C118 reveals a number of novel interactions with DOT1L. For example, the charged 5'-amino group of the compound forms a hydrogen bond with the carbonyl oxygen of Gly163. The urea region occupies the binding site of the amino acid region of SAM. The terminal propyl nitrogen of the urea interacts with the side chain oxygen atom of Asp161 in the same binding mode as the carboxylate nitrogen atom in SAM. The urea carbonyl oxygen interacts with the nitrogen atom of Asn 241, similar to the interaction of one of the carboxylate oxygen atoms of SAM. In addition, the proximal nitrogen atom of the urea (attached to the aromatic ring) coordinates with Asp161 (FIG. 4A). The steric bulk of the tert-butyl phenyl opens up the novel hydrophobic pocket by changing the side chain conformation of Phe239, Tyr312, Met147 and Leu143, inducing a significant conformational change in the 130s' loop to flip Thr 139 (a residue that otherwise interacts with the carboxylate terminus of SAM) away from the SAM binding pocket (FIG. 4B). The movement of Tyr312 causes a change in a loop consisting of residues 302-312 (300s' loop). These changes result in both the 130s' and 300s' loops of DOT1L becoming disordered (FIG. 4C).

Figure 5:
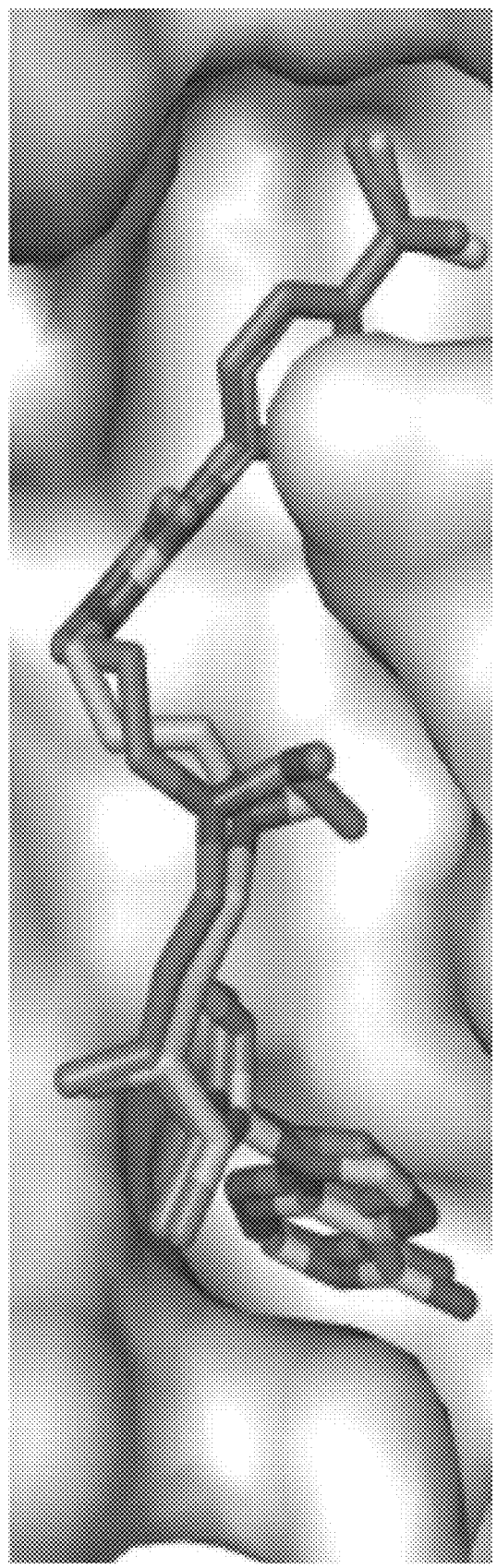
FIG. 5 is superimposition of Compound D16 and Compound C118 structures. The DOT1L protein of DOT1L-Compound D16 is in surface presentation in grey. Compound D16 (carbon atoms: magenta) is superimposed with Compound C118 (carbon atoms: green).

The crystal structure of the DOT1L-D16 complex reveals D16 binds to DOT1L in a similar manner as C118, with the 5'-amino isopropyl group occupying a region near that occupied by the methyl group of the thiomethyl on SAM (FIG. 5). Thus, the high potency, longer residence time compounds C118 and D16 are associated with a novel conformation of the enzyme that expands the contiguous active site cavity to include a new pocket; the crystal structures of these compounds suggest that these inhibitors "punch through" a protein wall to create this new pocket and to thus engage recognition elements both within the SAM/SAH binding pocket and the newly formed hydrophobic pocket. Because this conformational change is unique to DOT1L, these compounds show excellent selectivity against other PMTs(9).

In addition to the protein structural changes that attend potent inhibitor binding, it is often the case that inhibitor-induced displacement of key structural water molecules within enzyme active sites is a critical component of high-affinity ligand interactions. This may be a contributing factor in the tight-binding interactions between DOT1L and the aminonucleoside inhibitors presented here. However, the resolution of the various enzyme-inhibitor co-crystal structures is not sufficient for us to make any definitive statements with regard to the role of structural water molecule displacement in the binding of these compounds to DOT1L.

Correlation of Enzyme-Inhibitor Affinity with Cellular Activity

Inhibition of DOT1L is expected to lead to a concentration-dependent diminution of H3K79 methylation levels in treated cells. For cells bearing the chromosomal translocation of the MLL gene, the diminution of H3K79 methylation is expected to translated into reduced transcription of leukemogenic genes such as HOXA9(27) and thus to a concomitant inhibition of cell proliferation. It was demonstrated that the potent, selective DOT1L inhibitor D16 indeed leads to concentration-dependent inhibition of intracellular H3K79 dimethylation (H3K79me2), of HOXA9 gene transcription and antiproliferative effects selectively for MLL-rearranged leukemia cells. Hence, there appears to be a correlative relationship between DOT1L target engagement, reduction in intracellular formation of the enzyme product (H3K79me2) and downstream transcriptional events leading to antiproliferative efficacy for D16. In this study, these observations were extended to other members of the aminonucleoside series to establish more firmly the relationship between target engagement and phenotypic effects of DOT1L inhibitors.

Compounds C94, C118 and D16 provide a structurally related series of DOT1L inhibitors, spanning almost 4 orders of magnitude in target affinity, with which to test the relationship between enzyme inhibition and cellular efficacy. Various concentrations of each of these compounds were applied to MV4-11 cells bearing a chromosomal rearrangement of the MLL gene and the impact on H3K79me2 level, HOXA9 message and cell proliferation were assessed at appropriate time points, taking into account the distinct kinetics of compound impact on each of these cellular parameters. Table 6 below summarizes the results of these studies.

TABLE 6

| Compound | $K_i$ (nM) | Cellular IC$_{50}$ µM | | |
|---|---|---|---|---|
| | | H3K79 Methylation | HOXA9 mRNA | Proliferation |
| C94 | 845 ± 472 | 28 ± 25 | >50 | >50 |
| C118 | 13 ± 7 | 0.272 ± 0.014 | 6.9 ± 0.5 | 4.9 ± 3.9 |
| D16 | 0.30 ± 0.02 | 0.005 ± 0.003 | 0.83 ± 0.17 | 0.146 ± 0.072 |

Errors represented as standard deviation (SD)

Consistent with our mechanistic hypothesis, the data in Table 6 illustrate a clear relationship between enzyme engagement, inhibition of intracellular histone methylation, selective effects on gene transcription and antiproliferative efficacy. As was previously reported for D16, each of these DOT1L inhibitors showed selective inhibition of intracellular H3K79 methylation without effect on other histone methyl marks. Further, the antiproliferative effects of each of these DOT1L inhibitors were specific to MLL-rearranged leukemia cell lines; other leukemia cell lines without the chromosomal rearrangement of the MLL gene were essentially unaffected (antiproliferative $IC_{50}$>50 µM) by this series of DOT1L inhibitors. These data provide compelling evidence for a causal relationship between DOT1L inhibition and selective cell killing of MLL-rearranged leukemia cells by the aminonucleoside compound series.

The potent and selective inhibition of DOT1L by the aminonucleoside series translates into potent and selective inhibition of intracellular H3K79 methylation and to selective cell killing for leukemic cells bearing the MLL chromosomal translocation. The quantitative correlation between target engagement, intracellular inhibition of H3K79 methylation, and antiproliferative effects is striking, and leaves little doubt that the selective phenotypic effects of these compounds are driven directly by ablation of DOT1L enzymatic activity. These data provide a solid foundation upon which further optimization of DOT1L inhibitors may be conducted. The data provide compelling proof of concept for the application of DOT1L inhibitors for selective killing of MLL-rearranged leukemias and thus portent the utility of DOT1L inhibitors for therapeutic intervention in this disease.

Example 3: Tumor Anti-Proliferation Assays

The enzymatic activity of the protein methyltransferase (PMT) DOT1L has been shown to be a driver of cell proliferation in MLL-rearranged leukemia. Structure-guided design, together with robust biochemical and biological assays, was used to optimize the potency, selectivity and pharmacological features of the aminonucleosides, resulting in the Compound A2.

Figure 6:
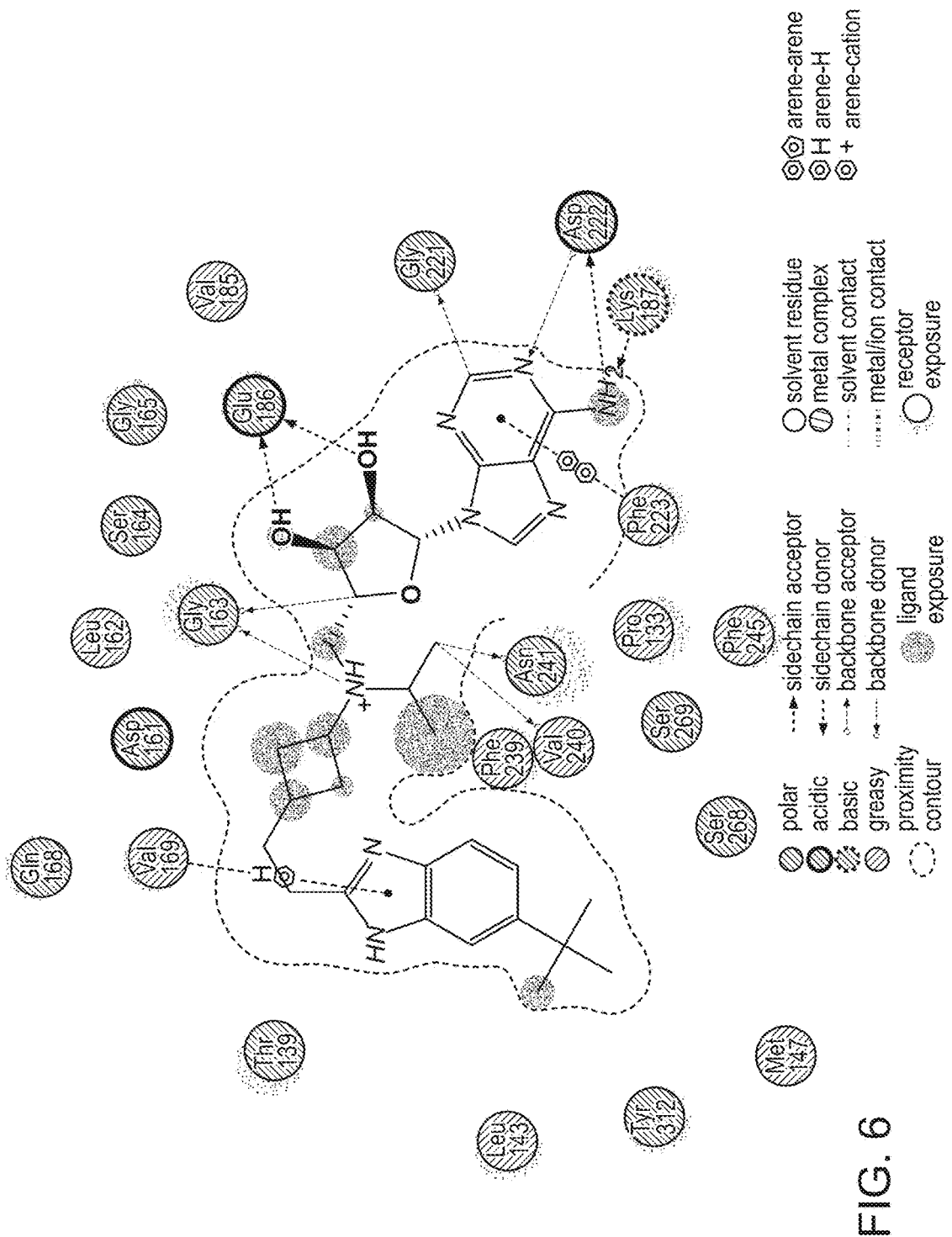
FIG. 6 is a ligand plot to show the binding pockets of DOT1L in complex with Compound A2.
Figure 7:
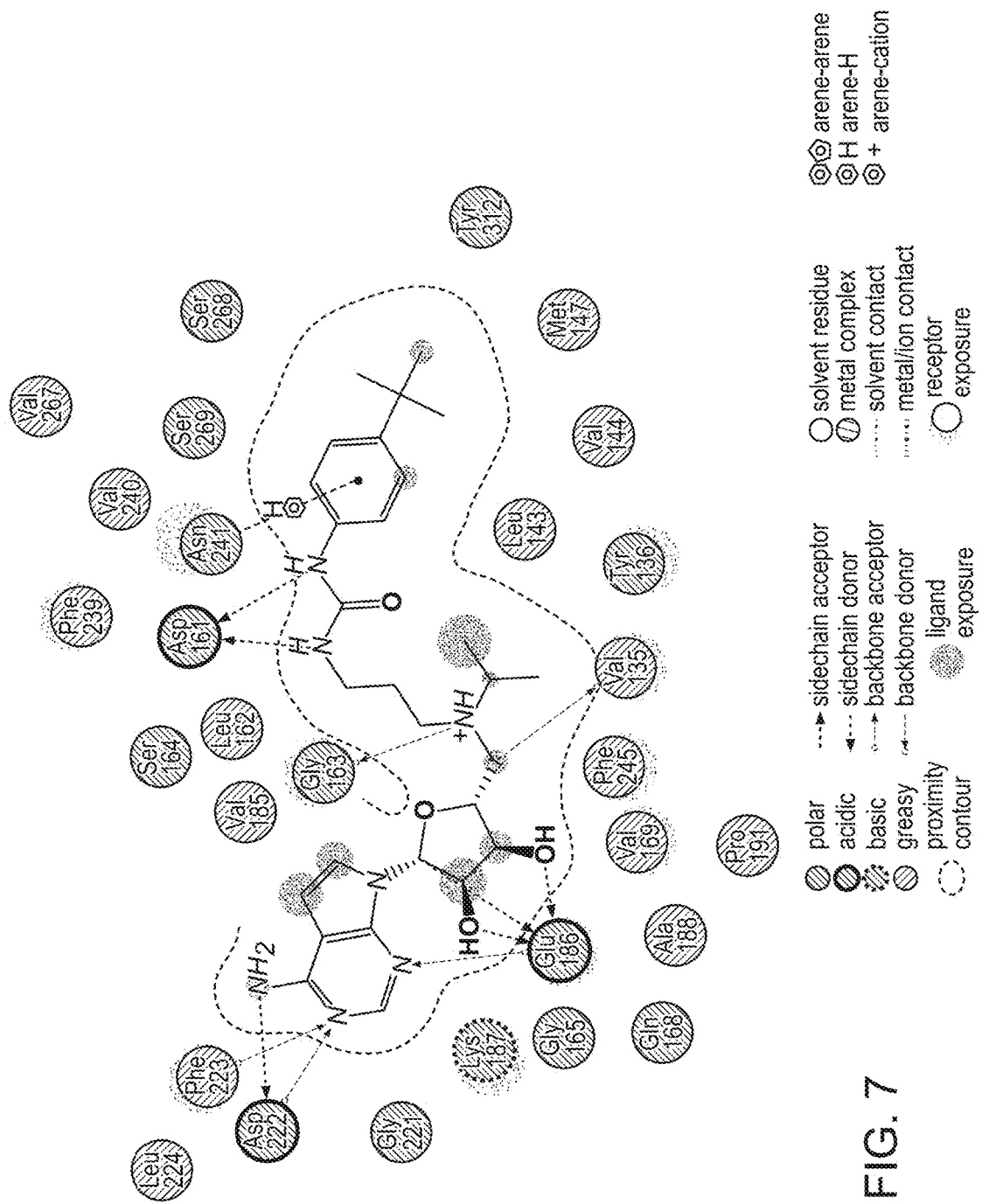
FIG. 7 is a ligand plot to show the binding pockets of DOT1L in complex with Compound D16.
Figure 8:
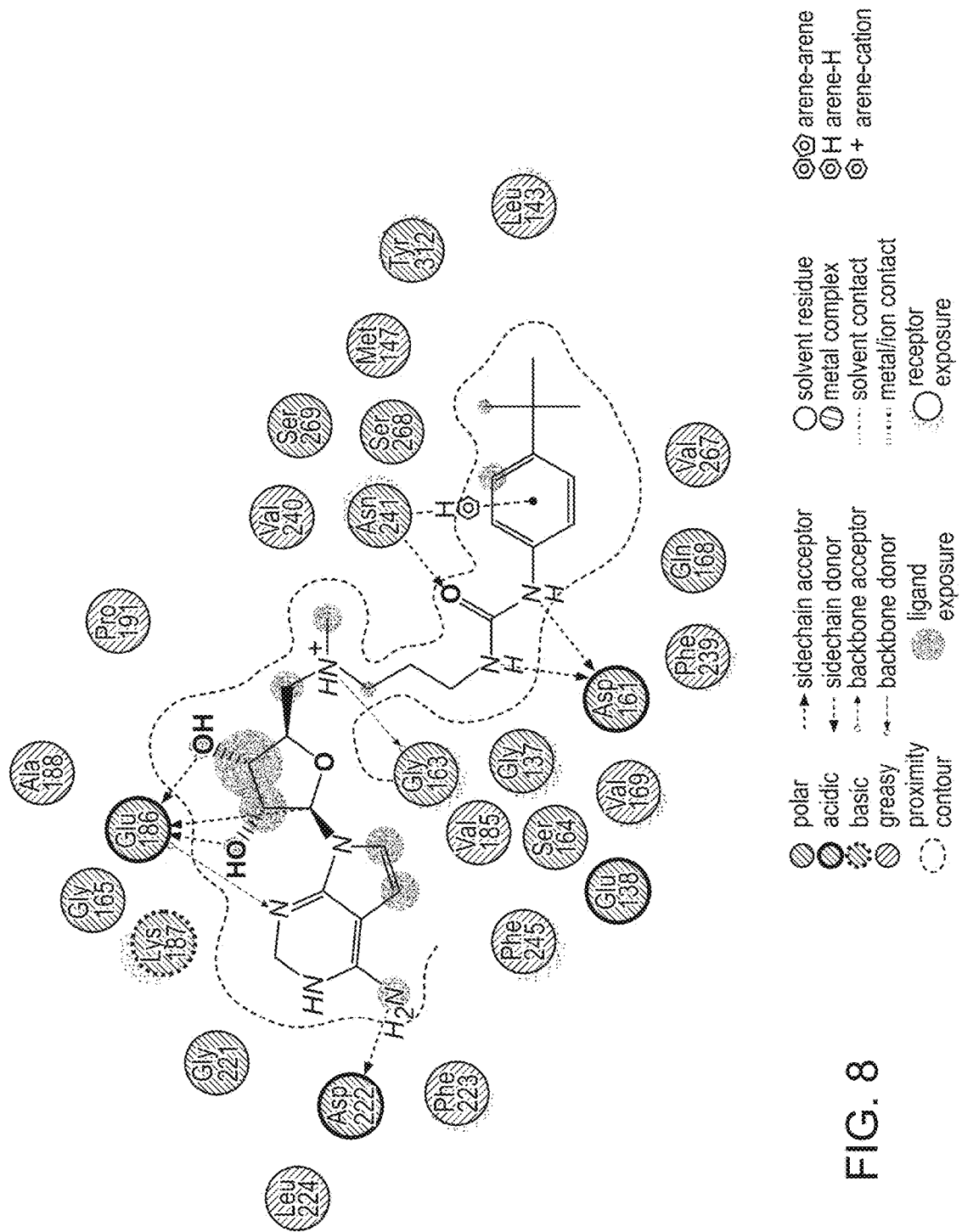
FIG. 8 is a ligand plot to show the binding pockets of DOT1L in complex with Compound D8.
Figure 9:
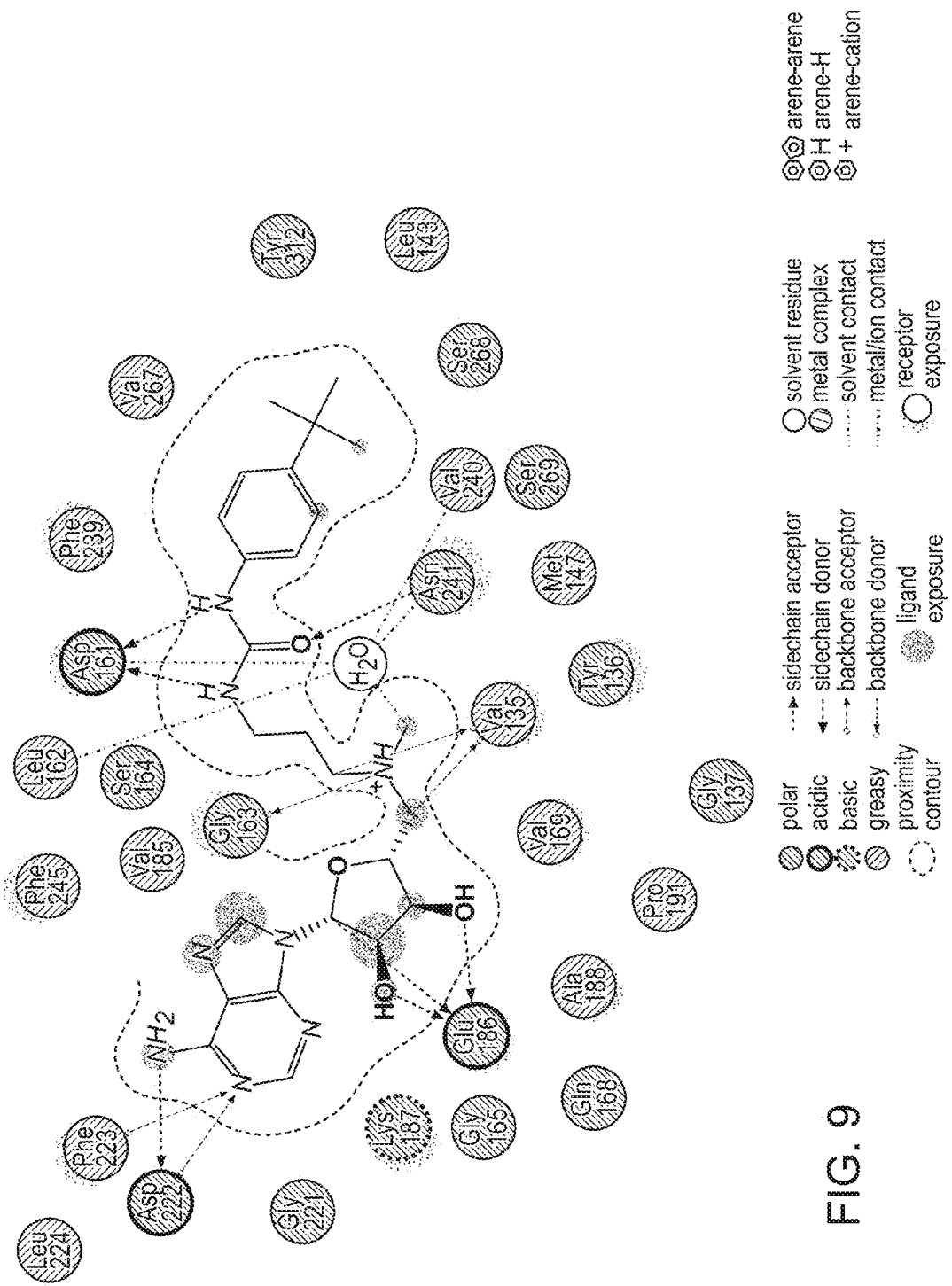
FIG. 9 is a ligand plot to show the binding pockets of DOT1L in complex with Compound C118.

Compound A2 is a S-adenosyl methionine (SAM) competitive inhibitor of DOT11L that displays a $K_i$ value of 80 pM and a drug-target residence time of >24 hours. The compound is highly selective for DOT1L, demonstrating >37,000-fold selectivity against all other PMTs tested. Crystallographic studies reveal that the high affinity, durable inhibition of DOT1L by Compound A2 has its origin in a conformational adaptation of the protein that attends inhibitor binding, extending the compound binding pocket to include novel recognition elements beyond the SAM binding active site, as illustrated in FIG. 6. Treatment of leukemia cells with Compound A2 results in concentration- and time-dependent diminution of H3K79 methylation without effect on the methylation status of other histone sites. The diminution of H3K79 methylation leads to inhibition of key MLL target genes and selective, apoptotic cell killing in MLL-rearranged leukemia cells, but has minimal impact on non-rearranged cells. Compound A2 is highly soluble in aqueous solution and can thus be formulated for intravenous administration. The effective pharmacokinetic half-life of Compound A2 in systemic circulation has been measured to be 0.25 and 1.5 h in rats and dogs, respectively. A nude rat subcutaneous xenograft model of MLL-rearranged leukemia has been established.

Four groups of 10 (Groups 1, 2, 3, and 4 female RH nu/nu rats (7 weeks old, weighing 120-160 g) bearing MV4-11 xenograft tumors of sizes ranging from 300-600 mm$^3$ were implanted with a catheter in the femoral vein). The infusion flow rate was set at 1,500 µL/hour/kg and was adjusted to the most recent mean body weight of each treatment group (as an example, the infusion flow rate was 300 µL/hour for a group of rats having a mean body weight of 200 g). Group 1 received vehicle via a 21-day continuous IV infusion. Group 2 received 21-day continuous IV infusion of the test substance at 35 mg/kg/day. Group 3 received a daily 8-hour continuous IV infusion of the test substance at 67 mg/kg/day for 21 consecutive days. Between two IV infusions of the test substance, the rats were kept under IV infusion with NaCl 0.9% solution. Group 4 received a 21-day continuous IV infusion of the test substance at 70 mg/kg/day. Syringes used for the IV infusion were replaced every day.

Blood samples were taken from all animals in Groups 1, 2, and 4 on designated days and assayed for plasma levels of Compound A2. Tumor size was measured on the designated days as shown in FIG. 1. The rats were terminated when the subcutaneous tumor reached a maximum volume of 9,000 mm$^3$ or at a maximum of 55 days after tumor cells injection.

As shown in FIG. 1, continuous intravenous infusion of Compound A2 for 21 days in this model leads to dose-dependent anti-tumor activity. At the highest dose, complete tumor regressions are achieved with no regrowth for up to 32 days after the cessation of treatment. In FIG. 1, Dose 1=35 mg/kg/day, and Dose 2=70 mg/kg/day.

No significant weight loss or obvious toxicity was observed in rats treated with Compound A2 during this efficacy study. Compound A2 is thus a potent, selective inhibitor of DOT1L that demonstrates strong efficacy in a rat xenograft model of MLL-rearranged leukemia.

TABLE 7

Summary of the Diffraction Data, Refinement, and Structure Statistics for Crystal Structures

|  | Compound C1 | Compound C118 | Compound D16 |
|---|---|---|---|
| Diffraction Data |  |  |  |
| Resolution (Å)* | 25.00-2.50 (2.59-2.50) | 41.70-2.80 (2.95-2.80) | 50.00-2.85 (2.95-2.85) |
| Space group | P65 | P65 | P65 |
| Unit-cell parameters |  |  |  |
| a (Å) | 152.81 | 157.60 | 155.05 |
| b (Å) | 152.81 | 157.60 | 155.05 |
| c (Å) | 51.37 | 49.15 | 48.45 |
| α (°) | 90.00 | 90.00 | 90 |
| β (°) | 90.00 | 90.00 | 90 |
| γ (°) | 120.00 | 120.00 | 90 |
| Completeness (%)* | 96.7 (81.3) | 100.0 (99.9) | 99.8 (100.0) |
| Redundancy* | 11.5 (3.1) | 6.1 (5.9) | 5.6 (5.6) |

TABLE 7-continued

Summary of the Diffraction Data, Refinement, and Structure Statistics for Crystal Structures

| | Compound C1 | Compound C118 | Compound D16 |
|---|---|---|---|
| Average I/σI* | 20.5 (2.41) | 11.8 (3.5) | 23.1 (4.0) |
| $R_{merge}$ (%)* | 9.5 (39.0) | 9.4 (42.1) | 8.0 (53.9) |
| Refinement Statistics | | | |
| Data (no cutoff) (Å)* | 23.94-2.50 (2.56-2.50) | 50.00-2.80 (2.87-2.80) | 41.09-2.85 (2.92-2.85) |
| $R_{working}$ (%)/No. of reflections* | 20.8/20874 (40.0/1274) | 21.0/15726 (30.0/1149) | 20.9/14244 (27.0/974) |
| $R_{free}$ (%)/No. of reflections* | 26.3/1189 (37.8/58) | 26.1/886 (40.2/54) | 26.2/785 (40.6/61) |
| R.m.s.d in bond lengths (Å) | 0.01 | 0.009 | 0.009 |
| R.m.s.d in bond angles (°) | 1.334 | 1.291 | 1.46 |
| Mean B factors (Å²) | 58.98 | 74.06 | 90.38 |
| Mean B factors for ligand (Å²) | 44.47 | 61.82 | 75.23 |
| Ramachandran plot | | | |
| Favored (%) | 90.3 | 87.2 | 87.5 |
| Additionally allowed (%) | 9.7 | 12.8 | 12.5 |
| Generously allowed (%) | 0 | 0 | 0 |

*Values in parentheses are for the highest-resolution shell

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (IIa) or a pharmaceutically acceptable salt or ester thereof:

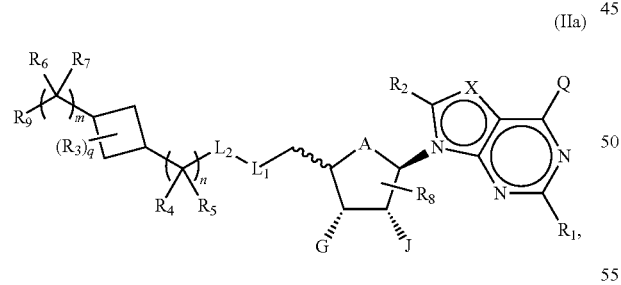

(IIa)

wherein,

A is O or $CH_2$;

each of G and J, independently, is H, halo, C(O)OH, C(O)O—$C_1$-$C_6$ alkyl or $OR_a$, $R_a$ being H, $C_1$-$C_6$ alkyl, C(O)—$C_1$-$C_6$ alkyl, or silyl, wherein C(O)O—$C_2$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

each X independently is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)

OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl;

each of R$_1$, R$_2$, R$_3$, R$_4$, R$_5$, R$_6$, and R$_7$, independently, is H, halo, hydroxyl, carboxyl, cyano, R$_{S2}$, R$_{S2}$ being amino, C$_1$-C$_6$ alkoxyl, C$_1$-C$_6$ alkyl, C$_2$-C$_6$ alkenyl, or C$_2$-C$_6$ alkynyl, and each R$_{S2}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$_8$ is H, halo or R$_{S3}$, R$_{S3}$ being C$_1$-C$_6$ alkyl, C$_2$-C$_6$ alkenyl, or C$_2$-C$_6$ alkynyl, and R$_{S3}$ being optionally substituted with one or more substituents selected from the group consisting of halo, hydroxyl, carboxyl, cyano amino, C$_1$-C$_6$ alkoxyl, mono-C$_1$-C$_6$ alkylamino, di-C$_1$-C$_6$ alkylamino, and C$_3$-C$_8$ cycloalkyl; and Q is H, NH$_2$, NHR$_b$, NR$_b$R$_c$, R$_b$, =O, OH, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$_9$ is

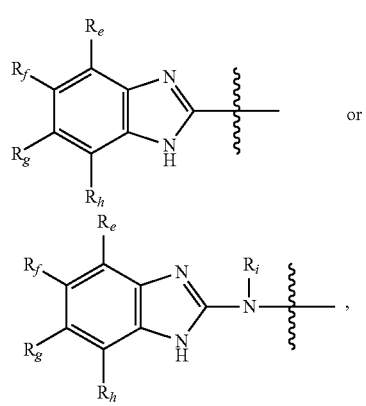

in which:

each of R$_e$, R$_f$, R$_g$, and R$_h$, independently is -M$_2$-T$_2$, in which M$_2$ is a bond, SO$_2$, SO, S, CO, CO$_2$, O, O—C$_1$-C$_4$ alkyl linker, C$_1$-C$_4$ alkyl linker, NH, or N(R$_t$), R$_t$ being C$_1$-C$_6$ alkyl, and T$_2$ is H, halo, or R$_{S4}$, R$_{S4}$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 8-membered heterocycloalkyl, or 5 to 10-membered heteroaryl, and each of O—C$_1$-C$_4$ alkyl linker, C$_1$-C$_4$ alkyl linker, R$_t$, and R$_{S4}$ being optionally substituted with one or more substituents selected from the group consisting of halo, hydroxyl, carboxyl, cyano, C$_1$-C$_6$ alkyl, C$_2$-C$_6$ alkenyl, C$_2$-C$_6$ alkynyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl, R$_i$ is H or C$_1$-C$_6$ alkyl optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

q is 0, 1, 2, 3, or 4;

m is 0, 1, or 2; and n is 0, 1, or 2.

2. The compound of claim 1, wherein R$_9$ induces a residence time of the compound greater than 20 seconds in a complex formed of the compound and human DOT1L.

3. The compound of claim 2, wherein the SAM binding pocket of human DOT1L is characterized by the crystallography coordinates of one or more human DOT1L amino acids Val135, Thr139, Asp161, Gly163, Gln168, Glu 186, Asp222, Phe223, and Asn241, according to Table S1 or S2.

4. The compound of claim 2, wherein the hydrophobic pocket domain of human DOT1L is characterized by the crystallography coordinates of human DOT1L amino acids Leu143, Met147, Phe239, and Tyr 312, according to Table S1 or S2.

5. The compound of claim 2, wherein the binding affinity (K$_i$) of the compound to human DOT1L is not greater than 50 μM.

6. The compound of claim 1, wherein one or more of R$_e$, R$_f$, R$_g$, and R$_h$ are selected from the group consisting of unsubstituted or substituted t-butyl, CF$_3$, cyclohexyl, C$_6$-C$_{10}$ aryl, and 5 to 10-membered heteroaryl.

7. The compound of claim 6, wherein the one or more of R$_e$, R$_f$, R$_g$, and R$_h$ are t-butyl.

8. The compound of claim 6, wherein R$_9$ is selected from the group consisting of

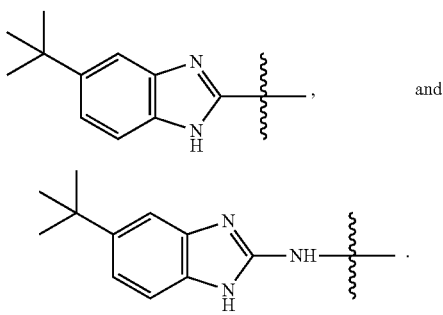

9. The compound of claim 1, being of Formula (IIc) or a pharmaceutically acceptable salt or ester thereof:

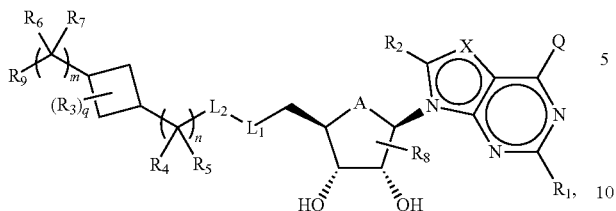

(IIc)

10. The compound of claim 9, being of Formula (IIIb) or a pharmaceutically acceptable salt or ester thereof:

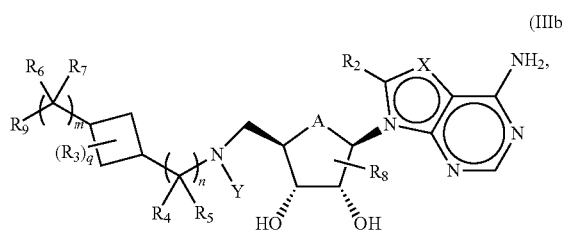

(IIIb)

wherein $R_3$ is H, halo, hydroxyl, carboxyl, cyano, or $R_{S2}$, and q is 0, 1, 2, 3, or 4.

11. The compound of claim 10, wherein $R_9$ is

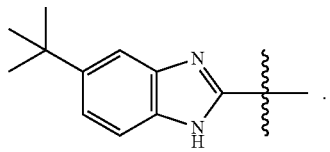 [SMILES: *c1nc2cc(C(C)(C)C)ccc2[nH]1]

.

12. The compound of claim 1, having molecular dimensions compatible with the shape of a hydrophobic pocket domain of DOT1L characterized by the crystallography coordinates of human DOT1L amino acids Leu143, Met147, Phe239, and Tyr 312, according to Table S1 or S2, wherein the compound has a biochemical $IC_{50}$ for DOT1L of less than 100 nM.

13. A pharmaceutical composition comprising a compound of claim 1 and a pharmaceutically acceptable carrier.

14. A method for treating cancer comprising administrating a therapeutically effective amount of a compound of claim 1 to a subject in need thereof.

* * * * *

UNITED STATES PATENT AND TRADEMARK OFFICE
CERTIFICATE OF CORRECTION

PATENT NO. : 10,112,968 B2
APPLICATION NO. : 15/176052
DATED : October 30, 2018
INVENTOR(S) : Edward J. Olhava et al.

It is certified that error appears in the above-identified patent and that said Letters Patent is hereby corrected as shown below:

In the Claims

At Column 105, Line 60, in Claim 1:
"$C(O)-C_1-C_6$ alkyl, or silyl, wherein $C(O)O-C_2-C_6$"
Should read:
--$C(O)-C_1-C_6$ alkyl, or silyl, wherein $C(O)O-C_1-C_6$--

At Column 107, Line 18, in Claim 1:
"consisting of halo, hydroxyl, carboxyl, cyano amino,"
Should read:
--consisting of halo, hydroxyl, carboxyl, cyano, amino,--

Signed and Sealed this
Eighth Day of January, 2019

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 416
<212> TYPE: PRT
<213> ORGANISM: Homo sapiens

<400> SEQUENCE: 1

Met Gly Glu Lys Leu Glu Leu Arg Leu Lys Ser Pro Val Gly Ala Glu
1               5                   10                  15

Pro Ala Val Tyr Pro Trp Pro Leu Pro Val Tyr Asp Lys His His Asp
                20                  25                  30

Ala Ala His Glu Ile Ile Glu Thr Ile Arg Trp Val Cys Glu Glu Ile
            35                  40                  45

Pro Asp Leu Lys Leu Ala Met Glu Asn Tyr Val Leu Ile Asp Tyr Asp
    50                  55                  60

Thr Lys Ser Phe Glu Ser Met Gln Arg Leu Cys Asp Lys Tyr Asn Arg
65                  70                  75                  80

Ala Ile Asp Ser Ile His Gln Leu Trp Lys Gly Thr Thr Gln Pro Met
                85                  90                  95

Lys Leu Asn Thr Arg Pro Ser Thr Gly Leu Leu Arg His Ile Leu Gln
                100                 105                 110

Gln Val Tyr Asn His Ser Val Thr Asp Pro Glu Lys Leu Asn Asn Tyr
            115                 120                 125

Glu Pro Phe Ser Pro Glu Val Tyr Gly Glu Thr Ser Phe Asp Leu Val
    130                 135                 140

Ala Gln Met Ile Asp Glu Ile Lys Met Thr Asp Asp Asp Leu Phe Val
145                 150                 155                 160

Asp Leu Gly Ser Gly Val Gly Gln Val Val Leu Gln Val Ala Ala Ala
                165                 170                 175
```

| | | | | | | | | | | | | |
|---|---|---|---|---|---|---|---|---|---|---|---|---|
|Thr|Asn|Cys|Lys 180|His|His|Tyr|Gly|Val 185|Glu|Lys|Ala|Asp|Ile 190|Pro|Ala|
|Lys|Tyr|Ala 195|Glu|Thr|Met|Asp|Arg 200|Glu|Phe|Arg|Lys|Trp 205|Met|Lys|Trp|
|Tyr|Gly|Lys 210|Lys|His|Ala|Glu|Tyr 215|Thr|Leu|Glu|Arg 220|Gly|Asp|Phe|Leu|
|Ser 225|Glu|Glu|Trp|Arg|Glu 230|Arg|Ile|Ala|Asn|Thr 235|Ser|Val|Ile|Phe|Val 240|
|Asn|Asn|Phe|Ala|Phe 245|Gly|Pro|Glu|Val|Asp 250|His|Gln|Leu|Lys|Glu 255|Arg|
|Phe|Ala|Asn|Met 260|Lys|Glu|Gly|Gly|Arg 265|Ile|Val|Ser|Ser|Lys 270|Pro|Phe|
|Ala|Pro|Leu 275|Asn|Phe|Arg|Ile|Asn 280|Ser|Arg|Asn|Leu|Ser 285|Asp|Ile|Gly|
|Thr|Ile 290|Met|Arg|Val|Val|Glu 295|Leu|Ser|Pro|Leu|Lys 300|Gly|Ser|Val|Ser|
|Trp 305|Thr|Gly|Lys|Pro|Val 310|Ser|Tyr|Tyr|Leu|His 315|Thr|Ile|Asp|Arg|Thr 320|
|Ile|Leu|Glu|Asn|Tyr 325|Phe|Ser|Ser|Leu|Lys 330|Asn|Pro|Lys|Leu|Arg 335|Glu|
|Glu|Gln|Glu|Ala 340|Ala|Arg|Arg|Arg|Gln 345|Gln|Arg|Glu|Ser|Lys 350|Ser|Asn|
|Ala|Ala|Thr|Pro 355|Thr|Lys|Gly|Pro 360|Glu|Gly|Lys|Val|Ala 365|Gly|Pro|Ala|
|Asp|Ala|Pro|Met 370|Asp|Ser|Gly|Ala 375|Glu|Glu|Glu|Lys|Ala 380|Gly|Ala|Ala|
|Thr 385|Val|Lys|Lys|Pro|Ser 390|Pro|Ser|Lys|Ala|Arg 395|Lys|Lys|Lys|Leu|Asn 400|
|Lys|Lys|Gly|Arg|Lys 405|Met|Ala|Gly|Arg|Lys 410|Arg|Gly|Arg|Pro|Lys 415|Lys|